US009050378B2

(12) United States Patent
Yang et al.

(10) Patent No.: US 9,050,378 B2
(45) Date of Patent: *Jun. 9, 2015

(54) N₂S₂ CHELATE-TARGETING LIGAND CONJUGATES

(75) Inventors: David J. Yang, Sugar Land, TX (US);
Dong-Fang Yu, Houston, TX (US);
Chang-Sok Oh, Houston, TX (US);
Jerry L. Bryant, Jr., Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 2062 days.

This patent is subject to a terminal disclaimer.

(21) Appl. No.: 10/732,919

(22) Filed: Dec. 10, 2003

(65) Prior Publication Data

US 2005/0129619 A1      Jun. 16, 2005

(51) Int. Cl.
*A61K 51/10*      (2006.01)
*A61K 51/04*      (2006.01)
*A61K 51/08*      (2006.01)

(52) U.S. Cl.
CPC ......... *A61K 51/1093* (2013.01); *A61K 51/0497* (2013.01); *A61K 51/088* (2013.01)

(58) Field of Classification Search
CPC ............ A61K 51/1093; A61K 51/088; A61K 51/0497
USPC ............. 424/9.1, 1.11, 1.41, 1.45, 1.53, 1.57, 424/9.36
See application file for complete search history.

(56) References Cited

U.S. PATENT DOCUMENTS

| | | | |
|---|---|---|---|
| 4,141,654 A | 2/1979 | Wardlaw et al. | 356/243.1 |
| 4,181,654 A | 1/1980 | Weitl et al. | 260/239 |
| 4,279,992 A | 7/1981 | Boguslaski et al. | 435/7 |
| 4,418,068 A | 11/1983 | Jones | 424/267 |
| 4,507,466 A | 3/1985 | Tomalia et al. | 528/332 |
| 4,558,120 A | 12/1985 | Tomalia et al. | 528/363 |
| 4,568,737 A | 2/1986 | Tomalia et al. | 528/332 |
| 4,587,329 A | 5/1986 | Tomalia et al. | 528/363 |
| 4,631,337 A | 12/1986 | Tomalia et al. | 528/391 |
| 4,694,064 A | 9/1987 | Tomalia et al. | 528/332 |
| 4,713,975 A | 12/1987 | Tomalia et al. | 73/864.8 |
| 4,730,968 A | 3/1988 | Diperstein et al. | 411/178 |
| 4,732,863 A | 3/1988 | Tomasi et al. | 436/547 |
| 4,737,550 A | 4/1988 | Tomalia | 525/419 |
| 4,789,542 A | 12/1988 | Goodman et al. | 424/1.1 |
| 4,824,659 A | 4/1989 | Hawthorne | 424/1.1 |
| 4,832,940 A | 5/1989 | Ege | 424/1.41 |
| 4,857,599 A | 8/1989 | Tomalia et al. | 525/259 |
| 4,861,869 A | 8/1989 | Nicolotti et al. | 424/1.53 |
| 4,871,779 A | 10/1989 | Killat et al. | 521/28 |
| 4,925,650 A | 5/1990 | Nosco et al. | 424/1.65 |
| 4,965,392 A | 10/1990 | Fritzberg et al. | 558/254 |
| 4,988,496 A | 1/1991 | Srinivasan et al. | 424/1.53 |
| 5,013,556 A | 5/1991 | Woodle et al. | 424/450 |
| 5,071,965 A | 12/1991 | Dunn et al. | 534/14 |
| 5,087,616 A | 2/1992 | Myers et al. | 514/21 |
| 5,108,921 A | 4/1992 | Low et al. | 435/240.1 |
| 5,164,294 A | 11/1992 | Skold et al. | 435/7.5 |
| 5,242,679 A | 9/1993 | Fritzberg et al. | 424/1.53 |
| 5,268,163 A | 12/1993 | Verbruggen | 424/1.1 |
| 5,279,811 A | 1/1994 | Bergstein et al. | 424/1.65 |
| 5,310,536 A * | 5/1994 | Srinivasan | 424/1.65 |
| 5,338,532 A * | 8/1994 | Tomalia et al. | 424/1.49 |
| 5,356,793 A | 10/1994 | Koezuka et al. | 435/32 |
| 5,412,072 A | 5/1995 | Sakurai et al. | 530/322 |
| 5,416,016 A | 5/1995 | Low et al. | 435/240.1 |
| 5,474,756 A | 12/1995 | Tweedle et al. | 424/9.363 |
| 5,517,993 A | 5/1996 | Unger et al. | 128/653.4 |
| 5,534,241 A | 7/1996 | Torchilin et al. | 424/9.321 |
| 5,541,287 A | 7/1996 | Yau et al. | 530/317 |
| 5,601,800 A | 2/1997 | Katti et al. | 424/1.77 |
| 5,605,671 A | 2/1997 | Lyle et al. | 424/1.41 |
| 5,605,672 A | 2/1997 | Bogdanov et al. | 424/1.65 |
| 5,608,060 A | 3/1997 | Axworthy et al. | 540/474 |
| 5,609,847 A * | 3/1997 | Belinka et al. | 424/1.69 |

(Continued)

FOREIGN PATENT DOCUMENTS

| | | |
|---|---|---|
| EP | 1156091 | 11/2001 |
| JP | 2002-516823 | 6/2002 |
| JP | 2002-522382 | 7/2002 |
| JP | 2002-241307 | 8/2002 |
| WO | WO 91/16076 | 10/1991 |
| WO | WO 95/28966 | 11/1995 |
| WO | WO 97/33552 | 9/1997 |
| WO | WO 98/08859 | 3/1998 |
| WO | WO 99/39748 | 8/1999 |
| WO | WO 99/49901 | 10/1999 |

(Continued)

OTHER PUBLICATIONS

Yang et al., Ann. Nucl. Med. Sci., 2000, 13, p. 19-36.*
Sumita, Radioisotopes, 1988, 37(9), p. 502-8 (abstract).*
Co-Pending U.S. Appl. No. 09/599,152, filed Jun. 21, 2000.
Co-Pending U.S. Appl. No. 10/672,763, filed Sep. 26, 2003.
Co-Pending U.S. Appl. No. 10/672,142, filed Sep. 26, 2003.

(Continued)

*Primary Examiner* — Michael G Hartley
*Assistant Examiner* — Leah Schlientz
(74) *Attorney, Agent, or Firm* — Parker Highlander PLLC

(57) ABSTRACT

The invention provides, in a general sense, a new labeling strategy employing compounds that are N₂S₂ chelates conjugated to a targeting ligand, wherein the targeting ligand is a disease cell cycle targeting compound, a tumor angiogenesis targeting ligand, a tumor apoptosis targeting ligand, a disease receptor targeting ligand, amifostine, angiostatin, monoclonal antibody C225, monoclonal antibody CD31, monoclonal antibody CD40, capecitabine, a COX-2 inhibitor, deoxycytidine, fullerene, herceptin, human serum albumin, lactose, leuteinizing hormone, pyridoxal, quinazoline, thalidomide, transferrin, or trimethyl lysine. The present invention also pertains to kits employing the compounds of interest, and methods of assessing the pharmacology of an agent of interest using the present compounds.

22 Claims, 45 Drawing Sheets

(56) References Cited

U.S. PATENT DOCUMENTS

| | | | |
|---|---|---|---|
| 5,620,675 A | 4/1997 | McBride et al. | 424/1.69 |
| 5,635,382 A | 6/1997 | Low et al. | 435/172.3 |
| 5,635,603 A | 6/1997 | Hansen et al. | 530/391.5 |
| 5,643,883 A | 7/1997 | Marchase et al. | 514/23 |
| 5,648,063 A | 7/1997 | Gries et al. | 424/9.363 |
| 5,670,132 A | 9/1997 | Griffiths et al. | 424/1.11 |
| 5,674,470 A | 10/1997 | Tweedle et al. | 424/9.363 |
| 5,688,487 A | 11/1997 | Linder et al. | 424/1.65 |
| 5,688,488 A | 11/1997 | Low et al. | 424/1.69 |
| 5,716,596 A | 2/1998 | Dean et al. | 424/1.69 |
| 5,730,968 A | 3/1998 | Butterfield et al. | 424/78.37 |
| 5,820,847 A | 10/1998 | Low et al. | 424/9.1 |
| 5,830,431 A | 11/1998 | Srinivasan et al. | 424/1.69 |
| 5,834,266 A | 11/1998 | Crabtree et al. | 435/172.3 |
| 5,846,519 A | 12/1998 | Tweedle et al. | 424/9.363 |
| 5,847,121 A | 12/1998 | Yau et al. | 540/474 |
| 5,877,289 A | 3/1999 | Thorpe et al. | 530/387.1 |
| 5,880,281 A | 3/1999 | Argese et al. | 540/474 |
| 5,891,468 A | 4/1999 | Martin et al. | 424/450 |
| 5,908,777 A | 6/1999 | Lee et al. | 435/320.1 |
| 5,951,964 A | 9/1999 | Dean et al. | 424/1.69 |
| 5,955,053 A | 9/1999 | Marzilli et al. | 424/1.65 |
| 5,955,605 A | 9/1999 | Axworthy et al. | 540/474 |
| 5,958,374 A | 9/1999 | Meares et al. | 424/1.65 |
| 5,977,163 A | 11/1999 | Li et al. | 514/449 |
| 5,986,074 A | 11/1999 | Marzilli et al. | 534/14 |
| 6,033,884 A | 3/2000 | Woo et al. | 435/172.3 |
| 6,054,436 A | 4/2000 | Crabtree et al. | 514/31 |
| 6,071,490 A | 6/2000 | Griffiths et al. | 424/1.49 |
| 6,071,533 A | 6/2000 | Papahadjopoulos et al. | 424/450 |
| 6,080,734 A * | 6/2000 | Zilch et al. | 514/81 |
| 6,083,741 A | 7/2000 | Hart et al. | 435/320.1 |
| 6,113,946 A | 9/2000 | Szoka, Jr. et al. | 424/486 |
| 6,143,274 A | 11/2000 | Tweedle et al. | 424/1.65 |
| 6,177,551 B1 | 1/2001 | Kasina | 534/10 |
| 6,187,286 B1 | 2/2001 | Elmaleh et al. | 424/1.73 |
| 6,197,278 B1 | 3/2001 | Blankenberg et al. | 424/1.69 |
| 6,232,295 B1 | 5/2001 | Kayyem et al. | 514/44 |
| 6,251,866 B1 | 6/2001 | Prakash et al. | 514/17 |
| 6,262,107 B1 | 7/2001 | Li et al. | 514/449 |
| 6,440,389 B1 | 8/2002 | Rabito | 424/9.6 |
| 6,521,209 B1 | 2/2003 | Meade et al. | 424/9.3 |
| 6,610,269 B1 * | 8/2003 | Klaveness et al. | 424/9.1 |
| 6,613,305 B1 | 9/2003 | Collins et al. | 424/1.73 |
| 6,656,450 B2 | 12/2003 | Hubin et al. | 424/9.363 |
| 6,692,724 B1 | 2/2004 | Yang et al. | 424/1.49 |
| 6,713,046 B1 | 3/2004 | Meade | 424/9.363 |
| 6,737,247 B2 | 5/2004 | Bogdanov et al. | 435/25 |
| 7,067,111 B1 | 6/2006 | Yang et al. | 424/9.1 |
| 7,121,926 B2 | 10/2006 | Sabde | 451/41 |
| 7,223,380 B2 | 5/2007 | Yang et al. | 424/9.4 |
| 7,229,604 B2 | 6/2007 | Yang et al. | 424/9.1 |
| 7,261,875 B2 | 8/2007 | Li et al. | 424/1.69 |
| 2001/0034363 A1 | 10/2001 | Li et al. | 514/449 |
| 2001/0041189 A1 | 11/2001 | Xu | 424/488 |
| 2003/0013772 A1 | 1/2003 | Murphy et al. | 514/674 |
| 2003/0152512 A1 | 8/2003 | Rajopadhye et al. | 424/1.49 |
| 2003/0206865 A1 | 11/2003 | Platzek et al. | 424/9.363 |
| 2004/0005641 A1 * | 1/2004 | Burnet et al. | 435/7.21 |
| 2004/0047917 A1 * | 3/2004 | Wilson et al. | 424/649 |
| 2006/0182687 A1 | 8/2006 | Yang et al. | 424/9.364 |

FOREIGN PATENT DOCUMENTS

| | | |
|---|---|---|
| WO | WO 99/56792 | 11/1999 |
| WO | WO 99/61512 | 12/1999 |
| WO | WO 00/45857 | 8/2000 |
| WO | WO 00/53233 | 9/2000 |
| WO | WO 00/61788 | 10/2000 |
| WO | WO 01/49324 | 7/2001 |
| WO | WO 01/72279 | 10/2001 |
| WO | WO 01/79258 | 10/2001 |
| WO | WO 01/80906 | 11/2001 |
| WO | WO 01/88106 | 11/2001 |
| WO | WO 01/91807 | 12/2001 |
| WO | WO 01/97843 | 12/2001 |
| WO | WO 02/06209 | 1/2002 |
| WO | WO 02/11677 | 2/2002 |
| WO | WO 02/39995 | 5/2002 |
| WO | WO 02/43775 | 6/2002 |
| WO | WO 02/056692 | 7/2002 |
| WO | WO 03/009874 | 2/2003 |
| WO | WO 03/051403 | 6/2003 |
| WO | WO 2006/016784 | 5/2006 |

OTHER PUBLICATIONS

Co-Pending U.S. Appl. No. 10/703,405, filed Nov. 7, 2003.

Boersma et al., "Quantification of apoptotic cells with fluorescein isothiocyanate-labeled annexin V in Chinese hamster ovary cell cultures treated with cisplatin," *Cytometry*, 24:123-130, 1996.

Cafaggi et al., "Synthesis and antitumor activity of a new cis-diammineplatinum (III) complex containing procaine hydrochloride," *Anticancer Research*, 12:2285-2292, 1992.

Cammisuli et al., "SDZ 281-977: a modified partial structure of lavendustin A that exerts potent and selective antiproliferative activities in vitro and in vivo," *Int J Cancer*, 65:351-359, 1996.

Chakrabarti et al., "Interaction of the antitumor antibiotic chromomycin A3 with glutathione, a sulfhydryl agent, and the effect upon its DNA binding properties," *Biochemical Pharmacology*, 56:1471-1479, 1998.

Connors, "Anticancer drug development: the way forward," *The Oncologist*, 1:180-181, 1996.

Guo and Gallo, "Selective protection of 2', 2'-difluorodeoxycytidine (Gemcitabine)," *J Org Chem*, 64:8319-8322, 1999.

Hirsch et al., "PK 11195, a ligand of the mitochondrial benzodiazepine receptor, facilitates the induction of apoptosis and reverses Bcl-2-mediated cytoprotection," *Experimental Cell Research*, 241:426-434, 1998.

Hjarnaa et al., "CHS 828, a novel pyridyl cyanoguanidine with potent antitumor activity in vitro and in vivo," *Cancer Res.*, 59:5751-5757, 1999.

Inoue et al., "Evaluation of In-111 DTPA-paclitaxel scintigraphy to predict response on murine tumors to paclitaxel," *Annals of Nuclear Medicine*, 13(3):169-174, 1999.

Jiang et al., "Antitumor activity of didemnin B in the human tumor stem cell assay," *Cancer Chemother Pharmacol*, 11:1-4, 1983.

Jiang et al., "3-(Iodoacetamido)-benzoylurea: a novel cancericidal tubulin ligand that inhibits microtubule polymerization, phosphorylates bcl-2, and induces apoptosis in tumor cells," *Cancer Res.*, 58:5389-5395, 1998.

LeClerc and Cedergren, "Modeling RNA-ligand interactions: the rev-binding element RNA-aminoglycoside complex," *J Med Chem*, 41:175-182, 1998.

Lundberg et al., "Conjugation of an anti-B-cell lymphoma monoclonal antibody, LL2, to long-circulating drug-carrier lipid emulsions," *J Pharm Pharmacol*, 51:1099-1105, 1999.

McGahon et al., "Chemotherapeutic drug-induced apoptosis in human leukaemic cells is intependent of the Fas (APO-1/CD95) receptor/ligand system," *British Journal of Haematology*, 101:539-547, 1998.

Meyer et al., "Tryptophan hydrolase antibodies used in the diagnosis of carcinoid," *Hepato-Gastroenterology*, 45:1522-1526, 1998.

Murray et al., "Matrix metalloproteinase-1 is associated with poor prognosis in oesophageal cancer," *Journal of Pathology*, 185:256-261, 1998.

Palyi et al., "Effects of methylacetylenic putrescine, and ornithine decarboxylase inhibitor and potential novel anticancer agent, on human and mouse cancer cell lines," *Anti-Cancer Drugs*, 10:103-111, 1999.

Pavicevic et al., "Serum tumor marker CYFRA 21-1 in the diagnostics of NSCLC lung cancer," *Coll Antropol*, 22(2):629-635, 1998.

Pavlik et al., "Properties of anticancer agents relevant to in vitro determinations of human tumor cell sensitivity," *Cancer Chemother Pharmacol*, 11:8-15, 1983.

Rasey et al., "Radiolabeled fluoromisonidazole as an imaging agent for tumor hypoxia," *Int J Radiation Oncology Biol Phys*, 17:985-991, 1989.

(56) References Cited

OTHER PUBLICATIONS

Rasey et al., "Characteristics of the binding of labeled fluoromisonidazole in cells in vitro," *Radiation Research*, 122:301-308, 1990.
Reutelingsperger and van Heerde, "Annexin V, the regulator of phosphatidylserine-catalyzed inflammation and coagulation during apoptosis," *Cell Mol Life Sci*, 53:527-532, 1997.
Thompson, "Apoptosis in the pathogenesis and treatment of disease," *Science*, 267:1456-1462, 1995.
Tolomeo et al., "The CD95/CD95 ligand system is not the major effector in anticancer drug-mediated apoptosis," *Cell Death and Differentiation*, 5:735-742, 1998.
Van den Eijnde et al., "In situ detection of apoptosis during embryogenesis with annexin V: from whole mount to ultrastructure," *Cytometry*, 29:313-320, 1997.
Wright et al., "Aminoglycoside antibiotics: structures, functions, and resistance," In: *Resolving the Antibiotic Paradox*, Rosen and Mobashery eds, Kluwer Academic/Plenum Pub NY, 1998.
Yoshinari et al., "Mode of action of a new indolocarbazole anticancer agent, J-107088, targeting topoisomerase I," *Cancer Res.*, 59:4271-4275, 1999.
Abrams et al., "Technetium-*99m*-human polyclonal IgG radiolabeled via the hydrazino nicotinamide derivative for imaging focal sites of infection in rats," *J. Nucl. Med.*, 31:2022-2028, 1990.
Alauddin and Conti, "Synthesis and preliminary evaluationo f 9-(4-{18F}-Fluoro-3-Hydroxymethylbutyl)guanine ([18F]FHBG): a new potential imaging agent for viral infection and gene therapy," *Nucl. Med. Biol.*, 25:175-180, 1998.
Alauddin et al., "9-[(3-18F]-fluoro-1-hydroxy-2-propoxy)methyl]guanine ([18F]-FHPG): a potential imaging agent of viral infection and gene therapy using PET," *Nucl. Med. Biol.*, 23:787-792, 1996.
Alauddin et al., "Evaluation of 9-[(3-18F]-fluoro-1-hydroxy-2-propoxy)methyl]guanine ([18F]-FHPG) in vitro and in vivo as probe for PET imaging of gene incorporation and expression in tumors," *Nucl. Med. Biol.*, 26:371-376, 1999.
Alauddin et al., "Receptor mediated uptake of a radiolabeled contrast agent sensitive to β-galactosidase activity," *Nucl. Med. Biol.*, 30:261-265, 2002.
Alper et al., "Assessment of renal functional changes following transurethral prostatectomy suing tc-99m ethylenedicysteine," *J. Nuclear Med.*, 37:289P, Abstract No. 1292, 1996.
Anderson et al., "N,N'-ethylene-di-1-cysteine (ec) complexes of ga(III) and In (III): molecular modeling, thermodynamic stability and in vivo studies," *Nucl. Med. Biol.*, 22:165-173, 1995.
Anderson et al., "Radiometal-labeled agents (non-technetium) for diagnostic imaging," *Chem. Rev.*, 99:2219-2234, 1999.
Antony, "Folate receptors," *Ann. Rev.*, 16:501-521, 1996.
Aoi et al., "Globular carbohydrate macromolecule 'sugar balls' 3. 'radical-growth polymerization' of sugar-substituted α-amino acid N-carboxyanhydrides (glycoNCAs) with a dendritic initiator," *Tetrahedron, Elsevier Science Publishers*, 53(45):15415-15427, 1997.
Appelbaum et al., "The use of radiolabeled anti-CD33 antibody to augment marrow irridation prior to marrow transplantation for acute myelogenous leukemia," *Transplantation*, 54(5):829-833, 1992.
Baidoo and Lever, "Evaluation of a diaminedithiol-based bifunctional chelate for labeling small molecules with $^{99m}$Tc," *Technetitum and Rhenium in Chemsitry and Nuclear Medicine*, 1990.
Baidoo et al., "Synthesis of a new diaminedithiol bifunctional chelate for the preparation of nuetral technetium complexes," *J. Nuclear Med.*, 31:806, Abstract No. 414, 1990.
Bajorin et al., *Proc. Annu. Meet. Am. Soc. Clin. Oncol.*, 7:250, A967, 1988.
Bakker et al., "Receptor scintigraphy with a radioiodinated somatostatin analogue: radiolabeling, purification, biologic activity and in vivo application in animals," *J. Nucl. Med.*, 31:1501-1509, 1990.
Bar-Sever et al., "Comparison of living related donor and recipient renograms in predicting the early postransplantation course," *J. Nuclear Med.*, 37:292P, Abstract No. 1305, 1996.

Baselga et al., "Phase I studies of anti-epidermal growth factor receptor cheimeric antibody C225 alone and in combination with cisplatin," *J. Clinical Oncology*, 18(4):904-914, 2000.
Baselga et al., "Recombinant humanized anti-HER2 antibody (herceptin) enhances the antitumor activity of paciltazel and doxorubicin against HER2/new overexpressing human breast cancer xenografts," *Cancer Research*, 58:2825-2831, 1998.
Becker et al., "Analysis of E-cadherin in diffuse-type gastric cancer using a mutation-specific monoclonal antibody," *American Journal of Pathology*, 155(6):1803-1809.
Benns et al., "Tailoring new gene delivery designs for specific targets," *Journal of Drug Targeting*, 8(1), Database Medline on STN International, Accession No. 2000222278, 2 pages, 2000.
Bertolini et al., "Angiogenic growth factors and endostatin in non-Hodgkin's lymphoma," *Br. J. Haematol.*, 106:5045, 1999.
Blair et al., "Linkage of cytotoxin agents to immunoglobulins," *Journal of Immunological Methods*, 59:129-143, 1983.
Blakenberg et al., "Apoptosis: the importance of nuclear medicine," *Nucl. Med. Comm.*, 21:241-250, 2000.
Blakenberg et al., "Imaging of apoptosis (programmed cell death) with $^{99m}$Tc annexin V.," *J. Nucl. Med.*, 40:184-191, 1999.
Blakenberg et al., "In vivo detection and imaging of phosphatidylserine expression during programmed cell death," *Proc. Natl. Acad. Sci., USA*, 95:6349-6354, 1998.
Block, "Poly(g-benzyl-L-glutamate) and other glutamic acid containing polymers," Gordon and Breach Science Publishers, New York, 11-31, 1983.
Blondeau et al., "Dimerization of an intermediate during the sodium in liquid ammonia reduction of L-thiazolidine-4-carboxylic acid," *Can J. Chem*, 45:49-52, 1967.
Bohdiewicz et al., "Indium-111 satumomab pendetide: the first FDA-approved monoclonal antibody for tumor imaging," *J. Nuclear Medicine Technology*, 26(3):155-163, 1998.
Bormans et al., "Synthesis and biological characteristics of the fourn stereoisomers of 99mTc-N, N'-bis-(mercaptoacetyl)2,3-diaminopropanoate," *Int. J. Rad. Appl. Instrum. B.*, 17(5);499-506, 1990.
Brechbiel et al., "Synthesis of 1 (P-isothiocyanatobenzyl) derivatives of DTPA and EDTA: antibody labeling and tumor-imaging studies," *Inorg. Chem.*, 25:2772-2781, 1986.
Brogi et al., "Hypoxia-induced paracrine regulation of vascular endothelial growth factor receptor expression," *J. Clin. Invest.*, 97(2):469-476, 1996.
Brokx et al., "Designing peptide-based scaffolds as drug delivery vehicles," *Science*, 78(1-3):115-123, 2002.
Budihardjo et al.,"Biochemical pathways of caspase activation during apoptosis," *Annu. Rev. Cell Dev. Biol.*, 15:269-290, 1999.
Burgen, "Targets of drug action," *Ann. Rev. Pharmacol. Toxicol.*, 40:1-16, 2000.
Burian et al., *Acta Otolaryngol.*, 119:289-292, 1999.
Bush et al., "Definitive evidence for hypoxic cells influencing cure in cancer therapy," *Br J Cancer*, (Suppl. III) 37:302-306, 1978.
Campbell et al., "Folate-binding protein is a marker for ovarian cancer," *Cancer Res*, 51:5329-5338, 1991.
Cao, "Therapeutic potentials of angiostatin in the treatment of cancer," *Haematologica*, 84:643-650, 1999.
Chapman et al., "Therapeutic antibody fragments with prolonged in vivo half-lives," *Nature Biotech.*, 17:780-783, 1999.
Chen et al., "Biological and pharmacokinetic evaluation of tc-99m ma2g2-b: a potential renal agent," *J. Nuclear Med.*, 35:263P, Abstract No. 1082, 1994.
Cherif et al., "Rapid synthesis of [$^{18}$F]Fluoro-1-(2'-Nitro-1'-Imidazolyl)-2-Propanol ([$^{18}$F]Fluoromisonidazole)," *Pharm Res.*, 11:466-469, 1994.
Cleynhens et al., "Synthesis and biological evaluation in mice of a monoamide derivative of tc99m-1,1-ec," *J. Nuclear Med.*, 38:186P, Abstract No. 799, 1997.
Collier et al. "Immunoscintigraphy performed with In-111-labeled CYT-103 in the management of colorectal cancer: comparison with CT," *Radiology*, 185:179-186, 1992.
Coney et al., "Chimeric murine-human antibodies directed against folate binding receptor are efficient mediators of ovarian carcinoma cell killing," *Cancer Res*, 54:2448-2455, 1994.

(56) References Cited

OTHER PUBLICATIONS

Corlija et al., "Contribution of radiolytically induced dissociation of 99mtc-d,1-hmpao in aqueous solutions," *J. Nuclear Med.*, 31:806, Abstract No. 413, 1990.
Culver et al., "In vivo gene transfer with retroviral vector-producer cells for treatment of experimental brain tumors," *Science*, 256:1550-1552, 1992.
Dagli et al., "Analysis of the complete dynamic scan data for camera-based determination of renal function," *J. Nuclear Med.*, 37:91P, Abstract No. 354, 1996.
Davison et al., "A new class of oxotechnetium(5+) chelate complexes containing a $TcON_2S_2$ Core," *Inorg Chem*, 20:1629-1632, 1981.
de Klerk et al., "Aspirin versus captopril renography in the diagnosis of renal artery stenosis," *J. Nuclear Med.*, 37:289P, Abstract No. 1291, 1996.
Deguchi et al., "Retention of biologic activity of human epidermal growth factor following conjugation to a blood-brain barrier drug delivery vector via an extended poly(ethylene glycol) linker," *Bioconjugate Chem.*, 10:32-37, 1999.
DeNardo et al., "Pharmacokinetics of chimeric L6 conjugated to indium 111- and yttrium-90-DOTA-peptide in tumor-bearing mice," *J. Nuclear Medicine*, 36:829-836, 1995.
DeNardo et al., "Yttrium-90/indoum-111-DOTA-peptide-chimeric L6: Pharmacokinetics, dosimetry and initial results in patients with incurable breast cancer," *Anticancer Research*, 17(3B):1735-1744, 1997.
Deutsch et al., "Synthesis of congeners and prodrugs, water-soluble prodrugs of taxol with potent antitumor activity," *J. Med. Chem.*, 32:788-792, 1989.
Deveraux and Reed, "IAP family proteins-suppressors of apoptosis," Genes and Development, 13:239-252, 1999.
Dewanjee et al., "Labeling antisense oligodeoxynucleotide (on) with tc-99m and hybridization with c-myc oncogene mrna in p388 leukemic cells," *J. Nuclear Med.*, 35:263P, Abstract No. 1081, 1994.
Dezutter et al., "Preparation and biological evaluation of technetium-$^{99m}$-L,L-propylenedicysteine" *J. of Labelled Cpd. Radiopharm.*, 42:553-565, 1999.
Dische, "A review of hypoxic-cell radiosensitization," *Int J Radiat Oncol Biol Phys*, 20:147-152, 1991.
Divgi et al., "Phase I and imaging trial of indium 111-labeled anti-epidermal growth factor receptor monoclonal antibody 225 in patients with squamous cell lung carcinoma," *J. National Cancer Institute*, 83(2):97-104, 1991.
Drobnik et al., "Soluble synthetic polymers in biological systems," *Adv. Polym. Sci.*, 57:1-50, 1984.
Dunn et al., "Receptor-mediated endocytosis of epidermal growth factor by hepatocytes in the perfused rat liver: ligand and receptor dynamics," *J. Cell Biol.*, 98:2148-2159, 1984.
Eary et al., "Radiochemistry of halogenated antibodies," *Antibodies in Radiodiagnosis and Therapy*, Boca Ratan, Florida, CPC Press, 83-100, 1988.
Eiseman et al., "Plasma pharmacokinetics and tissue distribution of paclitaxel in CD2F1 mice," *Cancer Chemother. Pharmacol.*, 34:465-471, 1994.
Eisenhut et al., "Synthesis and In Vivo Testing of a bromobutyl substituted 1,2-Dithia-5,9-diazacycloundecane: a versatile precursor for new $^{99m}$Tc-bis(aminoethanethiol) complexes," *Nucl. Med. Biol.*, 16:805-811, 1989.
Ennis et al., "Anti-epidermal growth factor receptor antibodies inhibit the autosrine-stimulated growth of MDA-468 human breast cancer cells," *Mol. Endocrinology*, 3(11):1830-1838, 1989.
Eshima et al., "Evaluating the role of protein binding on the renal extraction of tc-99m tubular agents utilizing an isolated perfused rat kidney model," *J. Nuclear Med.*, 37:47P, Abstract No. 178, 1996.
Ethier, "Growth factor synthesis and human breast cancer progression," *J. Natl. Cancer Inst.*, 87(13):964-973, 1995.
Fan et al., "Antitumor effect of anti-epidermal growth factor receptor monoclonal antibodies plus cis-diamminedichloroplatinum on well established A431 cell xenografts," *Cancer Research*, 53:4637-4642, 1993.
Fan et al., "Blockade of epidermal growth factor receptor function by bivalent and monovalent fragments of 225 anti-epidermal growth factor receptor monoclonal antibodies," *Cancer Research*, 53:4322-4328, 1993.
Fanciulli et al., "Glycolysis and growth rate in normal and in hexokinase-transfected NIH-3T3 cells," *Oncology Res.*, 6:405-409, 1994.
Fang et al., "Involvement of p21 Wafl in mediating inhibition of paclitaxel-induced apoptosis by epidermal growth factor in MDA-MB-468 human breast cancer cells," *Anticancer Research*, 20(1A):103-112, 2000.
Fidler et al., "The biology of cancer invasion and metastasis," *Adv. Cancer Res.*, 28:149-250, 1987.
Foa et al., "Taxol (paclitaxel): a novel anti-microtubule agent with remarkable anti-neoplastic activity," *J. Clin. Lab. Res.*, 24:6-14, 1994.
Frankel et al., "Targeted toxins," *Clin. Cancer Res.*, 6:326-334, 2000.
Franklin et al., "New anti-lung-cancer antibody cluster 12 reacts with human folate receptors present on adenocarcinoma," *Int J Cancer—Supplement*, 8:89-95, 1994.
Frisch and Screaton, "Anoikis mechanisms," *Curr. Opin. Cell Biol.*, 13:555-562, 2001.
Fuertges et al., "The clinical efficacy of poly(ethylene glycol)-modified porteins," *J. Controlled Release*, 11:139-148, 1990.
Fuller et al., "A procedure for the facile synthesis of amino-acid N-carboxyanhydride," *Biopolymers*, 15:1869, 1976.
Gabizon, "Selective tumor localization and improved therapeutic index of anthracyclines encapsulated in long-circulating liposomes," *Cancer Research*, 52:891-896, 1992.
Gambhir et al., "A mutant herpes simplex virus type 1 thymidine kinase reporter gene shows improved sensitivity for imaging reporter gene expression with positron emission tomography," *Proc. Natl. Acad. Sci., USA*, 97(6):2785-2790, 2000.
Gambhir et al., "Imaging adenoviral-directed reporter gene expression in living animals with positron emission tomography," *Proc. Natl. Acad. Sci., USA*, 96:2333-2338, 1999.
Gambhir et al., "Imaging of adenoviral-directed herpes simplex virus type 1 thymidine kinase reporter gene expression in mice with radiolabeled ganciclovir.," *J. Nucl. Med.*, 39:2003-2011, 1998.
Garayoa et al., "Hypoxia-inducible factor-1 (HIF-1) up-regulates adrenomedullin expression in human tumor cell lines during oxygen deprivation: a possible promotion mechanism of carcinogenesis," *Molecular Endocrinology*, 14:848-862, 2000.
Gariepy et al., "Vectorial delivery of macromolecules into cells using peptide-based vehicles," *Trends in Biotechnology*, 19(1):21-28, 2001.
Girard, "Mechanisms by which carbohydrates regulate expression genes for clycolytic and lipogenic enzymes," *Ann. Rev. Nutr.*, 17:325-352, 1997.
Giraud et al., "Application to a cartilage targeting strategy: Synthesis and in vivo biodistribution of $^{14}$C-labelled quaternary ammonium-glucosamine conjugates," *Bioconjug. Chem.*, 11:212-218, 2000.
Goh et al., "Growth hormone promotion of tubulin polymerization stabilizes the microtubule network and protects against colchicine-induced apoptosis," *Endrocrinology*, 139:4364-4372, 1998.
Goldenberg et al., "Imaging of human tumor xenografts with and indim-111-labeled anti-epidermal growth factor receptor monoclonal antibody," *J. National Cancer Institute*, 81:1616-1625, 1989.
Goldenberg, "Monoclonal antibodies in cancer detection and therapy," *Am. J. Med.*, 94:297-312, 1993.
Goldsmith et al., "Somatostatin receptor imaging in lymphoma," *Sem Nucl Med*, 25:262-271, 1995.
Goldsmith, "Receptor imaging: Competitive or complementary to antibody imaging,"*Sem Nucl Med.*, 27:85-93, 1997.
Goldspeil, "Pharmaceutical issues: preparation, administration, stability, and compatibility owth other medications," *Ann. Pharocother.*, 28:S23-S26, 1994.
Gonda, "Aerosols for delivery of therapeutic and diagnostic agents to the respiratory tract," *Critical Reviews in Therapeutic Drug Carrier Systems*, 6(4):273-313, 1990.
Green and Evan, "A matter of life and death," *Cancer Cell*, 1:19-30, 2002.

(56) References Cited

OTHER PUBLICATIONS

Greenfield et al., "In vitro evaluation of immunoconjugates prepared by linking mitomycin C to monoclonal antibodies via polyglutamic acid carriers," *Antibody, Immunoconjugates, and Radiopharmaceuticals*, 2(3):201-216, 1989.
Greenwald et al., "Drug delivery systems: water soluble tazol 2'-poly(ethylene glycol) ester prodrugs—design and in vivo effectiveness," *J. Med. Chem.*, 39:424-431, 1996.
Guozheng and Boli, "A new potential renal imaging agent 99mtcn-ec," *J. Labelled compounds and Radiopharmaceuticals*, XXXVII:797-798, 1995.
Hadley et al,"Magnetic resonance imaging in acute head injury," *Clin. Rad.*, 39:131-139, 1988.
Halpern et al., "Stability, characterization, and kinetics of In-labeled monoclonal antitumor antibodies in normal animals and nude mouse human tumor models," *Cancer Research*, 43:5347-5355, 1983.
Harada et al., "Insulin-induced egr-1 expression in chinese hamster ovary cells in insulin receptor an dinsulin receptor substrate-1 phosphorylation-independent," *J. Biol Chem.*, 270:26632-26638, 1995.
Hay et al., "Hypoxia-selective antitumor agents. Bis(nitroimidazolyl)alkanecarboxamides: a new class of hypoxia-selective cytotoxins and hypoxic cell radiosensitizers," *J Med. Chem.*, 37:381-391, 1994.
Hermann and Patel, "Adaptive recognition by nucleic acid aptamers," *Science*, 287:820-825, 2000.
Hermanson, "Amine detection reagents," *Bioconjugate Techniques*, San Diego, Academic Press, 112-114, 1996.
Hermanson, "Ellman's assay for the determination of sulfhydryls," *Bioconjugate Techniques*, Sand Diego, Academic Press, 88-90, 1996.
Hibi et al., "PGP9.5 as a candidate tumor marker for non-small-cell lung gancer," *American Journal of Pathology*, 155(3):711-715, 1999.
Hnatowich et al., "Radioactive labeling of antibody: a simple and efficient method," *Science*, 220:613-165, 1983.
Hoes et al., "Optimization of macromolecular prodrugs of the antitumor antibiotic adriamycin," *J. Controlled Release*, 2:205-213, 1985.
Holm et al., "Folate receptor of human mammary adenocarcinoma," *APMIS*, 102:413-419, 1994.
Holmes et al., "Current status oc clinical trials with paclitaxel and docetael, taxane anticancer agents: basic science and current status," *American Chemical Society*, Washington, DC, 31-57, 1995.
Hsueh and Dolnick, "Altered folate-binding protein mRNA stability in KB cells grown in folate-deficient medium," *Biochem Pharmacol*, 45:2537-2545, 1993.
Hudecz et al., "Influence of carrier on biodistibution and in vitro cytotoxicity of methotexate-branched polypeptide conjugates," *Bioconjugate Chemistry*, American Chemical Society, 4(1):25-33, 1993.
Ilgan et al., "$^{99m}$Tc-ethylenedicysteine-folate: a new tumor imaging agent, synthesis, labeling and evaluation in animals," *Cancer Biotherapy & Radiopharmaceuticals*, 13:427-435, 1998.
Inoue et al., "Paclitaxel enhances the effects of the anti-epidermal growth factor receptor monoclona antibody ImClone C225 in mice with metastatic human bladder transitional cell carcinoma," *Clinical Cancer Res.*, 6:4874, 4884, 2000.
Inoue et al., "The prognostic value of angiogenesis factor expression for predicting recurrence and metastasis of bladder cancer after neoadjuvant chemotherapy and radical cystectomy," *Clin. Cancer Res.*, 6:4866-4873, 2000.
Ionov et al., "Mutational inactivation of the proapoptotic gene BAX confers selective advantage during tumor clonal evolution," *Proc. Natl. Acad. Sci., USA*, 97(20):10872-10877, 2000.
Irie et al., "Regression of cutaneous metastic melanoma by inralesional injection with human monoclonal antibody to ganglioside GD2," *Proc. Natl. Acad. Sci., USA*, 83:8694-8698, 1986.
Itoh et al., "Graphic (patlak) method in tc-99m-mag3 renal scintigraphy: noninvasive calculation of extraction fraction (ef) and renal plasma flow (RPF)," *J. Nuclear Med.*, 37:291P, Abstract No. 1300, 1996.

Iyer et al., "8-[18F]Fluoropenciclovir: an improved reporter probe for imaging HSV1-tk reporter gene expression in vivo using PET," *J. Nucl. Med.*, 42(1):96-105, 2001.
Jamar et al., "Clearance of the new tubular agent Tc-*99m* L,L-ethylenedicysteine: Estimation by a simplified method,"*J Nucl Med*, 34:129P, 1993.
Jeppesen et al., Impact of polymer tether length on multiple ligand-recepotor bond formation, *Science*, 293:465-468, 2001.
John et al., "Tc-99m labeled ethylenediamines: quest for sigma receptor chelates," *J. Nuclear Med.*, 38:186P, Abstract No. 798, 1997.
Jones and Mayer, "Glucose metabolism in the rat small intestine: the effect of glucose analogues on hexokinase activity," *Biochem. J*, 132:125-128, 1973.
Jurisson et al., "Potential technitium small molecule radiopharmaceuticals," *Chem. Rev.*, 99:2205-2218, 1999.
Kabasakal et al., "Clinical comparison of technetium-$^{99m}$-ec, technetium-$^{99m}$-MAG3 and iodine-131-OIH in renal disorders," *J. Nucl. Med.*, 36(2):224-228, 1995.
Kabasakal et al., "Evaluation of technetium-99m-ethylenedicysteine in renal disorders and determination of extraction ratio," *J. Nucl. Med.*, 36(8):1398-1403, 1995.
Kabasakal et al., "Prospective validation of single plasma sample $^{99m}$Tc-ethylenedicysteine clearance in adults,"*J. Nucl. Med.*, 40:429-431, 1999.
Kabasakal et al., Simplified technetium-$^{99m}$-EC clearance in adults from a single plasma sample, *J. Nuclear Med.*, 38:1784-1786, 1997.
Kabasakal. "Technetium-99m ethylene dicysteine: a new renal tubular function agent," *Eur. J Nucl. Med.* 27:351-357, 2000.
Kanazawa et al., "19F NMR of 2-deoxy-2-fluro-D-glucos for tumor diagnosis in mice. An NDP-bound hexose analog as a new NMR target for imaging," *NMR in Biomed.*, 10:35-41, 1997.
Kanvinde et al., "Technetium-99m-γ-pyrones: a new class of tc-99m cationic complexes," *J. Nuclear Medicine*, 31:908, Abstract, 1990.
Kao et al., "Detection of esophageal carcinoma susing Tc-99m MIBI SPECT imaging," *Clin. Nucl. Med.*, 19(12):1069-1074, 1994.
Kao et al., "Relationship of alveolar permeability and lung inflammation in patients with active diffuse infiltrative lung disease detected by 99Tcm-DTPA radioaerosol inhalation lung scintigraphy and quantitative 67Ga lung scans," *Nucl. Med. Commun.*, 15(10):850-854, 1994.
Kao et al., "Role of radioisotope penile plethysmigraphy in the evaluation of penile hemodynamic of impotent patients," *J. Nuclear Med.*, 37:292P, Abstract No. 1304, 1996.
Kao et al., "Tc-99m MIBI uptake in breast carcinoma and axillary lymph node metastases," *Clin. Nuc. Med.*, 19(10):898-900, 1994.
Kato and Sugiyama, "Targeted delivery of peptides, proteins, and genes by receptor-mediated endocytosis," *Critical Reviews in Therapeutic Drug Carrier Systems*, 14(3):287-331, 1997.
Kato et al., "A novel method of conjugation of daunomycin with antibody with a poly-L-glutamic acid-a-fetoprotien antibody-daynomycin conjugate," *J. Med. Chem.*, 27:1602-1607, 1984.
Kengen, "Good results of tc-99m-mag3 clearance measurements with a dual headed gamma camera without plasma sampler,"*J. Nuclear Med.*, 37:91P, Abstract No. 353, 1996.
Kikukawa et al., "Early and delayed Tc-99m ECD brain SPECT in SLE patients with CNS involvement," *Ann Nucl Med.* 14:25-32, 2000.
Kim et al., "Synthesis, biodistribution and imaging of mammary tumors using 99mtc-ec-polyglutamate; a glutamate receptor peptide," *J. Nuclear Medicine*, 41:231P Abstract, 2000.
Kitamura et al., "Chemical engineering of the monoclonal antibody A7 by polyethylene clycol for targeting cancer chemotherapy," *Cancer Research*, 51:4310-4315, 1991.
Klok et al., "Star-shaped fluorescent polypeptides," *Journal of Polymer Science*, 39(10):1572-1582, 2001.
Knight et al, "Thrombus imaging with technetium-99m synthetic peptides based upon the binding domain of a monoclonal antibody to activated platelets," *J. Nucl. Med.*, 35:282-288, 1994.
Koh et al., "Imaging of hypoxia in human tumors with [F-18]fluoromisonidazole,"*Int J Radiat Oncol Biol Phys*, 22:199-212, 1992.
Kopecek et al. "Targetable polymeric prodrugs," *J. Control. Release*, 6:315-327, 1987.

(56) References Cited

OTHER PUBLICATIONS

Kopecek et al., "Targetable water-soluble polymeric antcancer drugs: achievements and unsolved problems," *Proc. Intern. Symp. Conol. Rel. Bioact. Mater.*, 20:190-191, 1993.
Kopecek, "The potential of water-soluble polymeric carriers in targeted and site-specific drug delivery," *Journal of Controlled Release*, 11:279-290, 1990.
Kranz et al., "Conjugates of folate and anti-T-cell-receptor antibodies specifically target folate-receptor-positive tumor cells for lysis," *Proc Natl Acad Sci*, 92:9057-9061, 1995.
Lamberts et al., "Somatostatin receptor imaging in vivo localization of tumors with a radiolabeled somatostatin analog," *J. Steoid Biochem Mol Biol*, 37:1079-1082, 1990.
Lamki, "Radioimmunoscintigraphy of cancer: problems, pitfalls, and prospects," *Nuclear Medicine Annual 1990*, New York, Raven Press Ltd., 113-150, 1990.
Larson et al., "Overview of clinical radioimmunodetection of human tumors," *Cancer*, 73(supp):832-835, 1994.
Leamon and Low, "Cytotoxicity of momordin-folate conjugates in cultured human cells," *J Biol Chem*, 267:24966-24971, 1992.
Leamon and Low, "Delivery of macromolecules into living cells: a method that exploits folate receptor endocytosis," *Proc Natl Acad Sci*, 88:5572-5576, 1991.
Leamon et al., "Cytotoxicity of folate-*pseudomonas*exotoxin conjugates toward tumor cells," *J Biol Chem*, 268:24847-24854, 1993.
Lee and Low, "Delivery of liposomes into cultured KB cells via folate receptor-mediated endocytosis," *J Biol Chem*, 269:3198-3204, 1994.
Li et al., "Antitumor activity of poly (L-glutamic acid)-paclitaxel on syngeneic and xenografter tumors," *Clinical Cancer Res.*, 5:891-897, 1999.
Li et al., "Complete regression of well-established tumors using a novel water-soluble poly(L-glutamic acid)-paclitaxel conjugate," *Cancer Res.*, 58:2404-2409, 1998.
Li et al., "Poly(L-glutamic acid)-anticancer drug conjugates," *Advanced Drug Delivery Rev.*, 54:695-713, 2002.
Li et al., "Synthesis and evaluation of water-soluble polyethylene glycol paclitaxel conjugate as a paclitaxel prodrug," *Anticancer Drugs*, 7(5):642-648, 1996.
Li et al., "Synthesis, metal chelate stability studies, and enzyme digestion of a peptide-linked DOTA derivative and its corresponding radiolabeled immunoconjugates," *Bioconjugate Chem.*, 4:275-283, 1993.
Liang et al., "The use of diaminodithiol for labeling small molecules with technetium-99m," *Nucl. Med. Biol.*, 14:63-67, 1987.
Lin et al., "The role of Tc-99m MDP and Ga-67 imaging in the clinical evaluation of malignant fibrous histiocytoma," *Clin. Nucl. Med.*, 19(11):996-1000, 1994.
Liu et al., "99mTc-labeled small peptides as diagnostic radiopharmaceuticals," *Chem. Rev.*, 99:2235-2268, 1999.
Liu et al., "Apoptotic signals delivered through the T-cell receptor of a T-cell hybrid require the immediate-early gene nur77," *Nature*, 367(6460):281-284, 1994.
Liu et al., "Bifunctional chelators for therapeutic lanthanide radiopharmaceuticals," *Bioconjugate Chemistry*, 12:7-34, 2001.
Liu et al., "Detection of anaerobic odontogenic infections by fluorine-18 fluoromisonidazole," *Eur. J. Nucl. Med.*, 23(10):1384-1387, 1996.
Liu et al., "Induction of apoptosis and activation of the capase cascade by anti-EGF receptor monoclonal antibodies in DiFI human colon cancer cells do not involve the C-jun N-terminal kinase activity," *British Journal of Cancer*, 82(12):1991-1999, 2000.
Lu et al., "Polymerizable fab' antibody fragments for targeting of anticancer drugs," *Nat. Biotech.*, 17:1101-1104, 1999.
Lu, "Antimitotic agents," In: Foye, WO. Ed., "Cancer chemotherapeutic agents," Washington, DC: American Chemical Society, 345-368, 1995.
Macapinlac et al., "Callium-67-citrate imaging in nuclear oncology," Nucl. Med. Biol., 21(5):731-738, 1994.

Maeda et al., "Tumoritropic and lymphotropic principles of macromolecular drugs," *Crit. Rev. Ther. Drug Carrier Syst.*, 6(3):193-210, 1989.
Maeda, "SMANCS and polymer-conjugated macromolecular drugs: advantages in cancer chemotherapy," *Adv. Drug Delivery Rev.*, 6(2):181-202, 1991.
Makin and Hickman, "Apoptosis and cancer chemotherapy," *Cell Tissue Res.*, 301:143-152, 2000.
Mangera and Verbruggen, "Synthesis and evaluation of .beta.-homocysteine derivatives of 99mTc-L, L-EC and 99mTc-L, L-ECD," *J. Labelled Comp.Radiopharm.*,42:683-699,1999.
Mann et al., "Molecular amplifiers: synthesis and functionalization of a poly(aminopropyl dextran bearing a uniquely reactive terminus for univalent attachment to biomolecules," *Bioconjugate Chemistry*, 3:154-159, 1992.
Marti and Risau, "Systematic hypoxia changes the organ-specific distribution of vascular endothelial growth factor and its receptors," *Proc. Natl. Acad. Sci., USA*, 95:15809-15814, 1998.
Martin et al., "Enhanced binding of the hypoxic cell marker [$^3$H]fluoromisonidazole in ischemic myocardium," *J Nucl Med*, 30:194-201, 1989.
Martin et al., "Noninvasive detection of hypoxic myocardium using fluorine-18 fluoromisonidazole and positron emission tomography," *J. Nucl. Med.*, 33(12):2202-2208, 1992.
Mason et al., "99mtc-desferoxamine: production, stability and solute clearance measurements after aerosolization,"*J. Nuclear Med.*, 31:908, Abstract No. 865, 1990.
Masui et al., "Growth inhibition of human tumor cells in athymic mice by anti-epidermal growth factor receptor monoclonal antibodies," *Cancer Research*, 44:1002-1007, 1984.
Mather et al., "Tumour cell uptake of technetium dithiocarbamate complexes," *J. Nuclear Med.*, 38:186P, Abstract No. 797, 1997.
Mathew et al., "Synthesis and evaluation of some water-soluble prodrugs and derivatives of taxol with antitumor activity," *J. Med. Chem.*, 35:145-151, 1992.
Mathias et al., "Tumor-selective radiopharmaceudcal targeting via receptor-mediated endocytosis of Gallium-67-deferoxamine-folate," *J Nucl Med*, 37:1003-1008, 1996.
Mathias et al., "Indium-111-DTPA-folate as a radiopharmaceutical for targeting tumor-associated folate binding protein," *J Nucl Med*, (Supplement) 38:133P, 1997.
Mathias et al., "Synthesis of Tc-*99m*-DTPA-folate and preliminary evaluation as a folate-receptor-targeted radiopharmaceutical,"*J Nucl Med*, (Supplement); 38:87P, 1997.
Meares et al., "Macrocyclic chelates of radiometals for diagnosis and therapy," *British J. Cancer*, 62:21-26, 1990.
Mease et al., "Comparison of renal agents for detecting unilateral acute ischemic/reperfusion renal injury in rats," *J. Nuclear Med.*, 36:231P, Abstract No. 1033, 1995.
Mendelsohn et al., "Anti-epidermal growth factor recepotr monoclonal antibodies may inhibit A431 tumor cell proliferation by blocking autocrine pathway," *Trans. Assoc. Am. Phys.*, 100:173-178, 1987.
Mendelsohn, "Epidermal growth factor receptor inhibition by a monoclonal antibody as anticancer therapy," *Clinical Cancer Research*, 3:2703-2707, 1997.
Meredith et al., "Treatment of metastatic prostate carcinoma with radiolabeled antibody CC49," J. Nucl. Med., 35(6):1017-1022, 1994.
Michiels et al., "Simultaneous estimation of effective renal plasma flow and glomerular filtration rate using tc-99m-ec.," *J. Nuclear Med.*, 37:91P, Abstract No. 355, 1996.
Miltross et al., "Relationship of mitotic arrest and apoptosis to antitumor effect of paclitaxel," *J. National Cancer Institute*, 88(18):1308-1314, 1996.
Mitchell et al., "Active-specific immunotherapy for melanoma," *J. Clin. Oncol.*, 8(5):856-869, 1990.
Mochizuki et al., "Synthesis of poly-L-glutamates containing 5-substituted uracil moieties," *Nucleic Acids Symp. Ser.*, 16:121-124, 1985.
Modjahedi et al., "The receptor for EGF and its ligands: expression, prognostic value and target for therapy in cancer (review)," *Int. J. Oncology*, 4(2):277-296, 1994.

(56) References Cited

OTHER PUBLICATIONS

Moller et al., "Biologic activities of naturally occurring human insulin receptor mutations," *J. Biol. Chem.*, 266:10995-11001, 1991.
Moran, "Technetium-$^{99m}$-EC and other potential new agents in renal nuclear medicine," *Seminars in Nucl. Med.*, 29: 91-101, 1999.
Morton et al., "Comparison of 2-point postural drainage with diuresis renography in the assessment hydronephrosis," *J. Nuclear Med.*, 37:46P, Abstract No. 174, 1996.
Morton et al., "Prolongation of survival in metastatic melanoma after active specific immunotherapy with a new polyvalent melanoma vaccine," *Ann. Surg.*, 216(4):463-482, 1992.
Mosmann, "Rapid colorimetic assay for cellular growth and survival: application to proliferation ans cytotoxicity assay,"*J. Immunol. Methods*, 65:55-63, 1983.
Mrhac et al., "Abnormal first-pass flow through the azygos vein from valsalva maneuver," *Clinical Nucl. Med.*, 21:331-332, 1996.
Namavari et al., "Synthesis of 8-[18F]Fluoroguanin derivatives: in vivo probes for imaging gene expression with positron emission tomography," *Nucl. Med. Biol.*, 27:157-162, 2000.
Nicolaou et al., "Design, synthesis, and biological activity of protaxols," *Nature*, 364:464-466, 1993.
Nosco et al., "Development of a kit formulation for 99mtcmag3 of very high purity and very high stability," *J. Nuclear Med.*, 31:908, Abstract No. 863, 1990.
Offield et al., "PDX-1 is required for pancreatic outgrowth and differentiation of the rostral duodenum," *Development*, 122:983-995, 1996.
Oldham et al., "Comparison of action of paclitaxel and poly (L-glutamic acid)-paclitaxel conjugate in human breast cacner cells," *Int. J. Oncol.*, 16(1):125-132, 2000.
Olexa et al.,"Radiolabeling of fibrinogen using the Iodogen technique," *Throm.Haemostas.*, 46(3):593-596, 1982.
Omelyanenko et al., "HPMA copolymer-anticancer drug-OV-TL16 antibody conjugates: influence of synthesis on the binding affinity to OVCAR-3 ovarian carcinoma cells in vitro," *J. Drug Targeting*, 3:357-373, 1996.
Omelyanenko et al., "HPMA copolymer-anticancer drug-OV-TL16 antibody conjugates II. Processing in epithelial ovarian carcinoma cells in vitro," *International Journal of Cancer*, 75(4):600-608, 1998.
Orr et al., "Similarity of folate receptor expression in UMSCC 38 cells to squamous cell carcinoma differentiation markers," *J Natl Cancer Inst*, 87:299-303, 1995.
Ozanne et al., "Over-expression of the EGF receptor is a hallmark of squamous cell carcinomas," *J. Pathol.*, 149:9-14, 1986.
Ozker et al.,"Technetium-$^{99m}$-N,N-ethylenedicysteine—a comparative study of renal scintigraphy with technetium-$^{99m}$-MAG3 and iodine-131-OIH in patients with obstructive renal disease," *J. Nucl. Med.*, 35:840-845, 1994.
Pedley et al., "The potential for enhanced tumour localisation by poly(ethylene glycol) modification of anti-CEA antibody," *British J. Cancer*, 70:1126-1130, 1994.
Petrak et al., "Transport of macromolecules across the capillary walls," *Adv. Drug Deliv. Review*, 3:191-214, 1989.
Phillips-Hughes et al., "Restenosis: pathophysiology and preventive strategies," *JVIR*, 7:321-333, 1996.
Pietersz et al., "Specific in vitro anti-tumor activity of methotrexate-monoclonal antibody conjugates prepared using human serum albumin as an intermediary," *Immunol. Cell Biol.*, 66:43-49, 1988.
Pimm et al., "Differences in tumor and normal tissue concentrations of iodine and indium labeled monoclonal antibody II: biodistribution studies in mice with human tumor xenografts," *Dur. J. Nucl. Med.*, 11:300-304, 1985.
Pimm et al., "Strategies for labelling branched polypeptides with a poly (L-Lysine) backbone with radioiodines 123I, 125I, 131I) and radiometals (111In, 51Cr) for biodistribution studies wnad radiopharmaceutical development," *Journal of Labelled Compunds and Radiopharmaceuticals*, 36(2):157-172, 1995.
Piper et al.,"A synthetic approach to poly(γ-glutamyl) conjugates of methotrexate," *J. Med. Chem.*, 26:291-294, 1983.

Pirmettis et al., "Synthesis and characterization of the tcd(ec) complex, a renal imaging agent," *J. Nuclear Med.*, 35:263P, Abstract No. 1079, 1994.
Popovici et al., "The influence of some antibiotics on hexokinase and pyruvate-kinase activity in the rat liver and kidney," *Arch. int. Pharmacodyn*, 193:80-86, 1971.
Potamianos et al., "Radioimmunoscintigraphy and radioimmunotherapy in cancer: principles and application," *Anticancer Research*, 20(2A):925-948, 2000.
Prvulovich et al., "Clinical evaluation of technetium-$^{99m}$-L,L-ethylenedicysteine in patients with chronic renal failure," *J. Nucl. Med.*, 38:809-814, 1997.
Putnam et al., "Polymer conjugates with anticancer activity," *Polymer Science*, 122:55-123, 1995.
Quadri et al., "Effects of linker chemistry on the pharmacokinetics of radioimmunoconjugates," *Quart. J. Nucl., Med.*, 42:250-261, 1998.
Raffauf et al., "Colchicine. Derivatives of trimethylcolchicinic acid," *J. Am Chem Soc*, 75:5292-5294, 1953.
Rasey et al., "Characterization of the binding of labeled fluoromisonidazole in cells in vitro," *Radiat Res*, 122:301-308, 1990.
Rasey et al., "Radiolabeled fluoromisonidazole as an imaging agent for tumor hypoxia," *Int. J. Radiat Oncol. Biol Phys*, 17:985-991, 1989.
Ratner and Clarke, "The action of formaldehyde upon cysteine," *J. Am Chem. Soc.*, 59:200-206, 1937.
Ravindranath et al., "Quantitation of the density of cell surface carbohydrate antigens on cancer cells with a sensitive cell-suspension ELISA," *J. Immunol. Methods*, 16(197):51-67, 1996.
Reed, "Apoptosis-targeted therapies for cancer," *Cancer Cell*, 3:17-22, 2003.
Reilly et al., "A comparison of EGF and Mab 528 labeled within for imaging human breast cancer," *J. Nucl. Med.*, 41:903-911, 2000.
Remington's Pharmaceutical Sciences, 19th Ed., Mach Printing Company, 1990, Smith and Rutlage, 1975.
Rihova et al., "Antiproliferative effect of a lectin- and anti-thy-1.2 antibody-targeted HPMA copolymer-bound doxorubicin on primary and metastatic human colorectal carcinoma and on human colorectal carcinoma transfected with the mouse thy-1.2 gene," *Bioconjugate Chemistry*, 11(5):664-673, 2000.
Rihova, "Receptor-mediated targeted drug or toxin delivery," *Adv. Drug Deliv. Rev.*, 29:273-289, 1998.
Rogers et al., "Neomycin effects on glucose transport by rat small intestine," *Digestion*, 1:159-164, 1968.
Rosenberg et al., "Experience with the use of high-dose interleukin-2 in the treatment of 652 cancer patients," *Ann. Surg.*, 210(4):474-548, 1989.
Ross et al., "Differential regulation of folate receptor isoforms in normal and malignant tissue in vivo and in established cell lines," *Cancer*, 73:2432-2443, 1994.
Roth et al., "Gene therapy for cancer: what have the inventors done and where are the inventors going?"*J. Natl. Can. Inst.*, 89(1):21-39, 1997.
Rowinsky et al., "Paclitaxel (taxol)," *New England Journal of Medicine*, 332:1004-1014, 1995.
Rowinsky et al., "Phase I and pharmacologic study of paclitaxel and cisplatin with granulocyte colony-stimulating factor: neuromuscular toxicity is dose-limiting," *J. Clin. Oncol.*, 11(10):2010-2020, 1993.
Rowland et al., "Suppression of tumor growth in mice by drug-antibody conjugate using a novel approach to linkage," *Nature*, 255:487-488, 1975.
Sabbantini et al., "Early findings in a phase I study of PG-Paclitaxel (CT2103 in recurrent ovarian or primary peritoneal cancer," *Proc. AACR-NCI-EORTC Int. Conference on Molecule Targets and Cancer Therapeutics*, Abs, 470:96, 2001.
Sasaki et al., "Assessment of antioxidative ability in brain: imaging of glutathione localization with technetium-99m meso-hexamethyl propyleneamine," *J. Nuclear Med.*, 35:263P, Abstract No. 1083, 1994.
Sato et al., "Simple estimation of fractional renal uptake of tc-99m mag3 using graphical analysis without syringe counting and renal depth correction," *J. Nuclear Med.*, 37:292P, Abstract No. 1303, 1996.

(56) References Cited

OTHER PUBLICATIONS

Seabold et al., "Comparison of $^{99m}$Tc-Methoxyisobutyl Isonitrile and $^{201}$Tl Scintigraphy for Detection of Residual Thyroid Cancer After $^{131}$I Ablative Therapy," *J. Nucl. Med.*, 40(9):1434-1440, 1999.
Semenza, "Regulation of mammalian O2 homeostasis by hypoxia-inducible factor 1," *Ann. Rev. Cell Dev. Biol.*, 15:551-578, 1999.
Serruys et al., "A comparison of balloon-expandable-stent implantation with balloon angioplasty in patients with comonary artery disease," *New England J. Medicine*, 331(8):489-495, 1994.
Seymour et al., "Synthetic polymers conjugated to monoclonal antibodies: vehicles for tumor-targeted drug delivery," *Select. Cancer Therapeut.*, 7(2):59-73, 1991.
Shankar et al., "Glucosamine infusion in rats mimics the beta-cell dysfunction of non-insulin-dependent diabetes mellitus," *Metabolism*, 47:573-577, 1998.
Shattuck et al., "Validation of the two sample technique for measuring gfr in renal transplant patients," *J. Nuclear Med.*, 36:231P, Abstract No. 1036, 1995.
Shih et al., "Anthracycline immunoconjugates prepared by a site-specific linkage via an amino-dextran intermediate carrier," *Cancer Res.*, 54:4192-4198, 1991.
Shimada et al., "Biodistribution of liposomes containing synthetic galactose-terminated diacylglyceryl-poly(ethylen glycol)s," *Biochimica et Biophysica Acta*, 1326:329-341, 1997.
Shuke et al., "Modified renal counting method for estimation of tc-99m mag3 renal clearance," *J. Nuclear Med.*, 37:291P, Abstract No. 1301, 1996.
Skrzypczak-Jankun et al, "Structure of the hirugen and hirulog 1 complexes of α-thrombin," *J. Mol. Biol.*, 221:1379-1393, 1991.
Smalley et al., "Localization of fluorescent compounds in the firefly light organ," *J. Histochem. Cytochem.*, 28(4):323-329, 1980.
Smith et al., "Prognostic significance of vascular endothelial growth factor protein levels in oral and oropharyngeal squamous cell carcinoma," *J. Clin. Oncol.*, 18(10):2046-2052, 2000.
Stoffel et al., Evaluation of technetium-99m-L,1-ec in renal transplant recipients: a comparative study with technetium-$^{99m}$-MAG3 and iodine-125-OIH, *J. Nucl. Med.*, 35:1951-1958, 1994.
Stuttle et al.,"Imaging of bone infection with labelled white blood cells: role of contemporaneous bone marrow imaging," *Eur. J. Nucl. Med.*, p. 17:148-151, 1990.
Subramanian et al., "Transchelation reactions in labeling ecd with tc-99m," *J. Nuclear Med.*, 31:908, Abstract No. 867, 1990.
Sudimack et al., "Targeted delivery via folate receptor," *Adv. Drug Deliv. Rev.*, 41:147-162, 2000.
Sun et al., "Idium(III) and Gallium(III) Complexes of Bis(aminoethanethiol) Ligands with Different Denticities: Stabilities, Molecular Modeling, and in Vivo Behavior," *Journal of Medicinal Chemistry*, 39(2):458(1996).
Surma et al., "Usefulness of Tc-*99m*-N,N'-ethylene-1-dicysteine complex for dynamic kidney investigations," *Nucl Med Comm*, 15:628-635, 1994.
Surwit et al., "Clinical assessmento f In-CYT-103 irnmunoscintigraphy in ovarian cancer," *Gynecol. Oncol.*, 48:285-292, 1993.
Suzuki et al., "A modified graphic method for estimation of glomerular filtration index using dynamic renal images with tc-99m dtpa," *J. Nuclear Med.*, 36:231P, Abstract No. 1035, 1995.
Taggart et al., *Human Mutation*, 13(3):210-220, 1999.
Tait and Smith, "Site-specific mutagenesis of annexin V: role of residues from Arg-200 to Lys-207 in phospholipid binding," *Arch Biochem Biophys*, 288:141-144, 1991.
Takamizawa et al., "Differential apoptosis gene expression in pediatric tumors of the kidney," *J. Ped. Surg.*, 35(2):390-395, 2000.
Takashina et al., "Comparative pharmacokinetic properties of murine monoclonal antibody A7 modified with neocarzinostatin, dextran and polyethylene glycol," *Jpn. J. Cancer Res.*, 82:1145-1150, 1991.
Tam, "Synthetic peptide vaccine design: synthesis and properties of a high-density multiple antigenic peptide system," *Proc. Natl. Acad. Sci., USA*, 85:5409-5413, 1988.

Taylor et al., "Comparison of tc-99m0(n,n1-ethylenedicysteine isomers in rats and in normal volunteers," *J. Nuclear Med.*, 37:46P-47P, Abstract No. 177, 1996.
Taylor et al., "Comparison of technetium-$^{99m}$-LL-EC isomers in rats and humans," *J. Nucl. Med.*, 38:821-826, 1997.
Tjuvajev et al., "Comparison of radiolabeled nucleoside probes (FIAU, FHGB, and FHPG) for PET imaging of HSV1-tk gene expression," *J. Nucl. Med.*, 43:1072-1083, 2002.
Tomalia et al., "Starburst dendrimers: molecular-level control of size, shape, surface chemistry, topology and flexibility from atoms to macroscopic matter," *Agnew. Chem. Int. Ed. Engl.*, 29:138-175, 1990.
Torchilin et al., "Chelating polymer modified monoclonal antibodies for radioimmunodiagnostics and radioimmunotherapy," *J. Controlled Release*, 24:111-118, 1993.
Tschopp et al., "Apoptosis: silencing the death receptors," *Curr. Biol.*, 9:R381-R384, 1999.
Tsukamoto et al., "The quantitation of absolute tc-99m-dmsa renal uptake in children from planar posterior-view method," *J. Nuclear Med.*, 37:291P, Abstract No. 1299, 1996.
Tubis et al.,"The preparation of $^{99m}$technetium-labelled cystine, methionine and synthetic polypetide and their distribution in mice," *Int;. Journ. Appl. Rad. Isotop.*, 19:835-840, 1968.
Tuli et al., "Comparison of a simplified quantitation of tc-99m mag-3 renogram to core needle biopsy in the diagnosis of renal transplant rejection," *J. Nuclear Med.*, 37:289P, Abstract No. 1290, 1996.
Ugar et al., "The diagnosis of renovascular hypertension with technetium-99m-ethylenedicysteine captopril scintigraphy," *Investigative Radiology*, 31:497-501, 1996.
Ugur et al., "Renovascular hypertension due to takayasu's arteritis demonstrated by Tc-$^{99m}$ethylenedicysteine captopril scintigraphy," *Clinical Nuclear Medicine*, 21:714-716, 1996.
Ugur et al., "Technetium-$^{99m}$-ethylenedicysteine in the diagnosis and follow-up of renovascular hypertension," *Investigative Radiology*, 31:378-381, 1996.
Ugur et al., "Technetium-$^{99m}$-ethylenedicysteine: an alternative agent to detect renovascular hypertension," *J. of Nuclear Med.*, 38:1662-1664, 1997.
Ugur et al., "The diagnosis of renovascular hypertension with tc-99m ethylenedicysteine captopril scintigraphy," *J. Nuclear Med.*, 37:291P, Abstract No. 1302, 1996.
Ugurel et al., "Increased serum concentration of angiogenic factors in malignant melanoma patients correlates with tumor progression and survival," *J. Clin. Oncol.*, 19(2):577-583, 2001.
Valk et al., "Hypoxia in human gliomas: Demonstration by PET with [$^{18}$F]fluoromisonidazole," *J Nucl Med*, 33:2133-2137, 1992.
Van Heeswijk et al., "The synthesis and characterization of polypeptide-adriamycin conjugates and its complexes with adiramycin Part 1," *J. Controlled Release*, 1:301-315, 1985.
Van Nerom et al., "Comparative evaluation of Tc-*99m* L,L-ethylenedicysteine and Tc-*99m* MAG3 in volunteers," *Eur J Nucl Med*, 16:417, 1990.
Van Nerom et al., "Comparison of renal excretion ocharacteristics of isomers 1,1 and d,d of tc-99m ethylenedicysteine," *J. Nuclear Med.*, 31:806, Abstract No. 412, 1990.
Van Nerom et al., "Optimalization of the labelling of ethylenedicysteine (ec) with technetium-99m," *J. Labelled Compounds and Radiopharmaceuticals*, XXX:37-39, 1991.
Van Nerom et al., "First experience in healthy volunteers with Tc-*99m*-L,L-ethylenedicysteine, a new renal imaging agent," *Eur J Nucl Med*, 20:738-746, 1993.
Van Schepdael et al., "Capillary electrophoretic analysis of ethylene dicysteine, a precursor of the radiopharmaceutical $^{99m}$Tc ethylene dicysteine," *J. Chromatography B*, 697:251-254, 1997.
Vega et al., "Targeting adriamycin to EGF receptors by site-specific conjugation of monoclonal antibody to poly(L-glutamic acid)," Division of Deagnostic Imaging and Departmetn of Experimental Therapeutics, U.T. M.D. Anderson Cancer Center, 1515 Holcombe Blvd., Houston, TX, USA.
Verbruggen et al., "Evaluation of Tc-*99m*-L,L-ethylenedicysteine as a potential alternative to Tc-*99m* MAG3," *Eur J Nucl Med*, 16:429, 1990.

(56) References Cited

OTHER PUBLICATIONS

Verbruggen et al., "Is syn or anti orientation of the oxotechnetium and carboxyl group in tc-99m renal function agents affecting the renal excretion rate?" *J. Labelled Compounds and Radiopharmaceuticals*, XXX:86-88, 1991.
Verbruggen et al., "Tc-99m1,1-ethylenedicysteine, a potential alternative to tc-99m mag3," *J. Nuclear Med.*, 31:908, Abstract No. 864, 1990.
Verbruggen et al., "Tc-*99m*-L,L-ethylenedicysteine: A renal imaging agent. I. Labelling and evaluation in animals," *J Nucl Med*, 33:551-557, 1992.
Villevalois-Cam et al., "Insulin-induced redistribution of the insulin-like growth factor II/mannose 6-phosphate receptor in intact rat liver," *J. Cell. Biochem.*, 77:310-322, 2000.
Vyas et al., "Phosphatase-activated prodrugs of paclitaxel," Taxane Anticancer Agents: Basic Science and Current Status, *American Chemical Society*, Washington, DC, 124-137, 1995.
Wahl et al., "Loss of normal p53 function conferes sensation to taxol by increasing g2/m arrest and apoptosis," *Nat. Med.*, 2(1):72-79, 1996.
Wahl, "Monoclonal antibodies in nucear medicine," *Nuclear Medicine Annual 1992*, New York, Raven Press Ltd., 91-103, 1992.
Walsh et al., "Noninvasive estimation of regional myocardial oxygen consumption by positron emission tomography with carbon-11 acetate in patients with myocardial infaction," *J. Nucl. Med.*, 30:1798-1808, 1989.
Wang et al., "Design and synthesis of [$^{111}$In]DTPA-folate for use as a tumor-targeted radiopharmaceutical," *Bioconjugate Chem*, 8:673-679, 1997.
Wang et al., "Synthesis, purification, and tumor cell uptake of Ga-67 deferoxamine-folate, a potential radiopharmaceutical for tumor imaging," *Bioconjugate Chem*, 7:56-62, 1996.
Washburn et al., "Reliable kit preparation of tc99m pentavalent dimercaptosuccinic acid [tc-99m (v) dmsa]," *J. Nuclear Med.*, 35:263P, Abstract No. 1080, 1994.
Weir et al, "Prognostic value of single-photon emission tomography in acute ischaemic strike," *Eur. Journ. Nuc. Med.*, 24:21-26, 1989.
Weiss et al., "Hypersensitivity reaction from taxol," *J. Clin. Oncol.*, 8(7):1263-1268, 1990.
Weitman et al., "Cellular localization of the folate receptor: potential role in drug toxicity and folate homeostasis," *Cancer Res*, 52:6708-6711, 1992b.
Weitman et al., "The folate receptor in central nervous system malignancies of childhood," *J Neuro-Oncology*, 21:107-112, 1994.
Weitman et al., "Distribution of the folate receptor GP38 in normal and malignant cell lines and tissues," *Cancer Research*, 52:3396-3401, 1992.
Wells et al., "Glycosylation of nucleocytoplasmic proteins: signal transduction and )-glcNAc," *Science*, 291:2376-2378, 2001.
Wen et al., "Conjugation with 111In-DTPA-poly(ethylene glycol) improves imaging of anti-EGF receptor antibody C225," *J. Nuclear Medicine*, 42(10):1530-1537, 2001.
Wen et al., "Improved radiolabeling of PEFylated protein: PEGylated annexin V for noninvasive imaging of tumor apoptosis," *Bioconjugate Chemistry*, 2002.
Wen et al., "Poly(ethylene glucol) conjugated anti-EGF receptor antibody C225 with radiometal chelator attached to the termini of polymer chains," *Bioconjugate Chem.*, 12:545-553, 2001.
Westerhof et al., "Membrane transport of natural folates and antifolate compounds in murine L1210 leukemia cells: Role of carrier- and receptor-mediated transport systems," *Cancer Res*, 51:5507-5513, 1991.
Wu et al., "Apoptosis induced by and anti-epidermal growth factor receptor monoclonal antibody in a human colorectal carcinoma cell line and its delay by insulin," *J. Clin. Invest.*, 95:1897-1905, 1995.
Yaghoubi et al., "Human pharacokinetic and dosimetry studies of {18F]FHBG: a reporter probe for imaging herpes simplex virus type-1 thymidine kinase reporter gene expression," *J. Nucl. Med.*, 42:1225-1234, 2001.

Yamori et al., Potent antitumor activity of MS-247, a novel DNA minor groove binder, evaluated by an in vitro and in vivo human cancer cell line panel., *Cancer Res.*, 59:4042-4049, 1999.
Yang et al., "Development of F-18-labeled fluoroerythronitroimidazole as a PET agent for imaging tumor hypoxia," *Radiology*, 194:795-800, 1995.
Yang et al., "99mtc-ec-deoxyglucose: synthesis, cellular uptake, biodistribution an dscintigraphic imaging," *J. Labelled Cpd. Radiopharm.*, 44:S513-S514, Abstract, 2001.
Yang et al., "Imaging tumor folate receptors using 99mtc-ethylenedicysteine-folate," *Proceedings of the American Association for Cancer Research*, 40:259, Abstract #1720, 1999.
Yang et al., "Imaging tumor folate receptors using radiolabeled folate and methotrexate," *J. Labelled Cpd. Radiopharm.*, 42:S696-S697, 1999.
Yang et al., "Molecular imaging using 99m-tc-ec-nitroimidazole, and 99mtc-ec-annexin v in tumor-bearing rodents," *Proceedings of the American Association for Cancer Research Annual Meeting*, 41:766, Abstract, 2000.
Yang et al., "Noninvasive assesment of tumor hypoxia with 99mTc labeled metronidazole," *Pharm. Research*, 16:743-750, 1999.
Yasui et al., "Expression of epidermal growth factor receptor in human gastric and colonic carcinomas," *Cancer Res.*, 48:137-141, 1995.
Ye et al., TRAF family proteins interact with the common neurotrophin receptor and modulate apoptosis induction, *J. Biol. Chem.*, 274(42):30202-30208, 1999.
Yeh et al., "Fluorine-18 fluoromisonidazole tumour to muscle retention ratio for the detection of hypoxia in nasopharyngeal carcinoma," *Eur. J. Nucl. Med.*, 23(10):1378-1383, 1996.
Yen et al., "A comparative study of evaluating renal scars by 99mTc-DSMA planar and SPECT renal scans, intravenous urography, and ultrasonography," *Ann. Nucl. Med.*, 8(2):147-152, 1994.
Yen et al., "Technetium-99m-DMSA renal SPECT in diagnosing and monitoring pediatric acute pyelonephritis," *J. Nucl. Med.*, 37(8):1349-1353, 1996.
Yen et al., "The role of technetium-99m sestamibi whole-body scans in diagnosing metastatic Hurthle cell carcinoma of the thyroid gland after total thyroidectomy: a comparison with iodine-131 and thallium-201 whole-body scans," *Eur. J. Nucl. Med.*, 21(9):980-983, 1994.
Yokoyama et al., "Polymer micelles as novel drug carrier: adriamycin-conjugated poly(ethylen glycol)-poly(aspartic acid) block copolymer," *J. Controlled Release*, 11:269-278, 1990.
Yoshino et al., "Differential effects of troglitazone and D-chiroinositol on glucosamine-induced insulin resistance in vivo in rats," *Metabolism.* 48:1418-23, 1999.
Anderson et al., "Copper-64-Labeled Antibodies for PET Imaging," *J. Nuclear Medicine*, 33:1685-1691, 1992.
Anderson et al., "Preparation, Biodistribution and Dosimetry of Copper-64-Labeled Anti-Colorectal Carcinoma Monoclonal Antibody Fragments 1A3-F(ab')2," *J. Nuclear Medicine*, 36:850-858, 1995.
Auzeloux et al., "Technetium-99m Radiolabelling of an N-Amino-Alkyl-Benzamide Nitrido- and Oxo-Technetium Bis(Aminoethanethiol) Derivative Synthesis and Biological Results. Potential Melanoma Tracer Agents," *J. Labelled Compounds and Radiopharmaceuticals*, 42:567-579, 1999.
Ginobbi et al., "Folic acid-polylysine carrier improves efficacy of c-myc antisense oligodeoxynucleotides on human melanoma (M14) cells," *Anticancer Res*, 17:29-35, 1997.
Jamar et al., "Clinical evaluation of Tc-*99m* L,L-ethylenedicysteine, a new renal tracer, in transplanted patients," *J Nucl Med*, 34:129P, 1993.
Kung et al., "Synthesis of new bis(aminoethanethiol) (BAT) derivatives: possible ligands for 99mTc brain imaging agents," *J. Med. Chem*, 28:1280-1284, 1985.
Nordsmark et al., "Pretreatment oxygenation predicts radiation response in advanced squamous cell carcinoma of the head and neck," *Radiother Oncol*, 41:31-39, 1996.
Wang et al., "Microtubule-interfering agents activate c-Jun N-terminal kinasae/stress-activated protein kinase through both Ras and apoptosis signal-regulating kinase pathways," *J. Biol. Chem.*, 273:4928-4936, 1998.

(56) References Cited

OTHER PUBLICATIONS

Wester et al., "Synthesis and radiopharmacology of -O(2-[$^{18}$F]fluoroethyl)-L-Tyrosine for tumor imaging," *J. Nucl. Med.*, 40:205-212, 1999.

Yokoyama et al., "Preparation of micelle-formin polymer-drug conjugates," *Bioconjugate Chem.*, 3:295-301, 1992.

Verbeke et al., "Development of a conjugate of 99mtc-ec with aminomethylenediphosphonate in the search for a bone tracer with fast clearance from soft tissue," *Bioconjugate Chemistry*, 13:16-22, 2002.

Verbeke et al., "Preparation and preliminary evaluation of <99m>Tc-EC-for-MLFK," *Nuclear Medicine and Biology*, 29:585-592, 2002.

U.S. Appl. No. 10/627,763, filed Jul. 28, 2003, Lin.

U.S. Appl. No. 11/737,694, filed Apr. 19, 2007, Yang.

U.S. Appl. No. 60/828,347, filed Oct. 5, 2005, Yang.

Aime et al., "Ternary Gd(III)L-HAS adducts: evidence for the replacement of inner-sphere water molecules by coordinating groups of the protein. implications for the design of contrast agents for MRI," *J. of Biol. Inorg. Chem.*, 5:488-497, 2000.

Angello et al., "Effect of eating on thallium-201 myocardial redistribution after myocardial ischemia," *Am. J. Cardiol.*, 60:528-533, 1987.

Benveniste and Davies, "Aminoglycoside antibiotic-inactivating enzymes in actinomycetes similar to those present in clinical isolates of antibiotic-resistant bacteria," *Proc. Natl. Acad. Sci. USA*, 70:2276-2280, 1973.

Borchardt et al., "Targeted actinium-225 in vivo generators for therapy of ovarian cancer," *Cancer Research*, 63:5084-5090, 2003.

Borodina et al., "Metabolic network analysis of *Streptomyces tenebrarius*, a *Streptomyces* species with an active entner-doudoroff pathway," *Appl. Environ. Microb.*, 71:2294-2302, 2005.

Boschi et al., "A CD(4)/T(4) receptor peptide ligand labeled with technetium-99m: synthesis and biological activity," *Nucl. Med. Biol.*, 27:791-795, 2000.

Botta et al., "NMR relaxometric study of new Gd$^{III}$ macrocyclic complexes and their interaction with human serum albumin," *Organic & Biomolecular Chemistry*, 2:570-577, 2004.

Brouwers et al., "Optimization of radioimmunotherapy of renal cell carcinoma: labeling of monoclonal antibody cG250 with $^{131}$I, $^{90}$I, $^{177}$Lu, or $^{186}$Re," *J. Nucl. Med.*, 45:327-337, 2004.

Canet et al., "Kinetic characterization of CMD-A2-Gd-DOTA as an intravascular contrast agent for myocardial perfusion measurement with MRI," *Magentic Resonance in Medicine*, 43:403-409, 2000.

Chappell et al., "Synthesis, characterization, and evaluation of a novel bifunctional chelating agent for the lead isotopes $^{203}$Pb and $^{212}$Pb," *Nucl. Med. Biol.*, 27:93-100, 2000.

Chmura et al., "Electrophilic chelating agents for irreversible binding of metal chelates to engineered antibodies," *J. of Controlled Release*, 78:249-258, 2002.

Connett et al., "Maximum tolerated dose and large tumor radioimmunotherapy studies of 64Cu-labeled monoclonal antibody 1A3 in a colon cancer model," *Clin. Cancer Res.*, 5(10 Suppl):3207s-3212s, 1999.

Connett et al., "Radioimmunotherapy with a 64Cu-labeled monoclonal antibody: a comparison with 67Cu," *Proc. Natl. Acad. Sci. USA*, 93:6814-6818, 1996.

Craig et al., "Renal outcomes for children on year after urinary tract infection," *J. Nuclear Med.*, 37:46P, Abstract No. 175, 1996.

Cronin et al., "A new class of macrocycle capable of binding exogenous metals: synthesis, structure, magnetic and electrochemical properties of a Cu(II) trinuclear complex based upon 1,4,8,11-tetraazacyclotetradecane-2,3-dione [exoO(2)]cyclam," *J. Chem. Soc., Dalton Transactions*, 12:1925-1927, 1999.

Cutler et al., "Dosimetry of copper-64-labeled monoclonal antibody 1A3 as determined by PET imaging of the torso," *J. Nucl. Med.*, 36:2363-2371, 1995.

Das et al., "[$^{186/188}$Re] rhenium-ethylene dicysteine (Re-Ec): preparation and evaluation for possible use in endovascular brachytherapy," *Nucl. Med. Biol.*, 27:189-197, 2000.

DeNardo et al., "Enhancement of 67Cu-2IT-BAT-LYM-1 therapy in mice with human Burkitt's lymphoma (Raji) using interleukin-2," *Cancer*, 80(12 Suppl):2576-2582, 1997.

Diamond et al., "Glycolysis in quiescent cultures of 3T3 cells. Stimulation by serum, epidermal growth factor, and insulin in intact cells and persistence of the stimulation after cell homogenization," *J. Biol. Chem.*, 253:866-871, 1978.

Drapé et al., "Intraarticular diffusion of Gd-DOTA after intravenous injection in the kneww: MR imaging evaluation," *Radiology*, 188:227-234, 1993.

Edreira et al., "Optimization of the small-scale synthesis of DOTA-Tyr$^3$-octreotide," *Nuclear Medicine Communications*, 23:493-499, 2002.

Ellis and Sharma, "Co, Fe and Ga chelates for cell labelling: a potential use in PET imaging?" *Nuclear Medicine Communications*, 20:1017-1021, 1999.

Froidevaux et al., "Preclinical comparison in AR4-2J tumore bearing mice of four radiolabeled 1,4,7,10-tetraazacyclododecane-1,4,7,10-tetraacetic acid somatostatin analogs for tumor diagnosis and internal radiotherapy," *Endocrinology*, 141:3304-3312, 2000.

Green and Wuts, Chapter 1, 1999.
Green and Wuts, Chapter 2, 1999.
Green and Wuts, Chapter 4, 1999.
Green and Wuts, Chapter 5, 1999.
Green and Wuts, Chapter 6, 1999.
Green and Wuts, Chapter 7, 1999.

Gregson et al., "meso-5,5,7,12,14-Hexamethyl-1,4,8,11-tetraazacyclotetradecane as a building block in supramolecular chemistry; salts formed with 2,2'-biphenol, 4,4'-thiodiphenol, 4,4'sulfonyldiphenol, 3- and 4-hydroxybenzoic acids, 3,5-dihydroxybenzoic acid and phenylphosphonic acid; supramolecular structures in zero, one, two and three dimensions," *Acta Crystallogr.*, B56:39-57, 2000.

Griffiths et al., "$^{90}$Y-DOTA-hLL2: an agent for radioimmunotherapy of Non-Hodgkin's lymphoma," *J. Nucl. Med.*, 44:77-84, 2003.

Gutman et al., Time to completed redistribution of thallium-201 in exercise myocardial scintigraphy: relationship to the degree of coronary artery stenosis, *Am. Heart J.*, 106:989-995, 1983.

Henson et al., "Gadolinium-enhanced CT angiography of the circle of Willis and neck," *AJNR Am. J. Neuroradiol.*, 25:969-972, 2004.

Hoelscher et al., "Effects of very high antibiotic concentrations on human intervertebral disc cell proliferation, viability, and metabolism in vitro," *Spine*, 25:1871-1877, 2000.

Honess et al., "Preclinical evaluation of the novel hypoxic marker $^{99m}$Tc-HL91 (prognox) in murine and xenograft systems in vivo," *Int. J. Radiation Oncology Biol. Phys.*, 42:731-735, 1998.

Hostetler and Hall, "Inhibition of kidney lysosomal phospholipases A and C by aminoglycoside antibiotics: possible mechanism of aminoglycoside toxicity," *PNAS*, 79:1663-1667, 1982.

Hu, "Neomycin inhibits angiogenin-induced angiogenesis," *Proc. Natl. Acad. Sci. USA*, 95:9791-9795, 1998.

Im et al., "Formation, properties, and characterization of a fully reduced Fe(II)Fe(II) form of spinach (and parsley) [2Fe-2S] ferredoxin with the macrocyclic complex [Cr(15-aneN(4))(H(2)O)(2)](2+) as reductant," *Inorg. Chem.*, 36:1388-1396, 1997.

Im et al., "The Cr$^{II}$Lreduction of [2Fe-2S] ferredoxins and site of attachment of Cr$^{III}$ using $^1$H NMR and site-directed mutagenesis," *Inorg. Chem.*, 39:1755-1764, 2000.

Ito et al., "PET and planar imaging of tumor hypoxia with labeled metronidazole," *Acad. Radiol.*, 13:598-609, 2006.

Kao et al., "Technetium-99m methoxyisobutylisonitrile chest imaging of small cell lung carcinoma," *Cancer*, 83:64-68, 1998.

King et al., "Imaging of bone infection with labelled white bloo cells: role of contemporaneous bone marrow imaging," *European Journal of Nuclear Medicine*, 17:18-151, 1990.

Kitamura and Shibata, "Preparation and the covalent hydration of a hexafluoro-2,4-pentanedionatotetraaminecobalt(III) complex," *Inorganica Chimica Acta*, 203:37-42, 1993.

Knight et al., "Radiolabeling of fibrinogen using the lodogen technique," *Throm. Res. Cen. Dept. Biochem.*, pp. 593-596, 1982.

Kundra et al., "Noninvasive monitoring of somatostatin receptor type 2 chimeric gene transfer," *J. Nucl. Med.*, 43:406-412, 2002.

(56) References Cited

OTHER PUBLICATIONS

Laissy et al., "Functional evaluation of normal and ischemic kidney by means of gadolinium-DOTA enhanced TurboFLASH MR imaging: a preliminary comparison with 99Tc-MAG3 dynamic scintigraphy," *Magn. Reson. Imaging*, 12:413-419, 1994.
Lewis et al., "Conjugation of monoclonal antibodies with TETA using activated esters: biological comparison of 64Cu-TETA-1A3 with 64Cu-BAT-21T-1A3," *Cancer Biother. Radiopharm.*, 16:483-94, 2001.
Li et al., "N,N'Ethylenedi-$_L$-cysteine (EC) and its metal complexes: synthesis, characterization, crystal structures, and equilibrium constants," *Inorg. Chem.*, 35:404-414, 1996.
Li et al., "Vinyl sulfone bifunctional derivatives of DOTA allow sulfhydryl- or amino-directed coupling to antibodies. Conjugates retain immunoreactivity and have similar biodistributions," *Bioconjugate Chem.*, 13:110-115, 2002.
Luckay et al., "Synthesis and structure of a complex of bismuth(III) with nitrogen donor macrocycle," *Journal of the Chemical Society, Chem. Comm.*, 2365-2366, 1995.
Michalik et al., "Effect of various aminoglycoside antibiotics on glucose formation in isolated rabbit kidney-cortex tubules ," *Pharmacol. Res.*, 21:405-414, 1989.
Murakami et al., "Calcium hydroxide ameliorates tobramycin toxicity in cultured chick tibiae," *Bone*, 21:411-418, 1997.
Murakami et al., "Interaction of tobramycin and pH in cultured chick tibiae," *J. Orthop. Res.*, 14:742-748, 1996.
Myszka et al., "Synthesis and induction of apoptosis in B cell chronic leukemia by diosgenyl 2-amino-2-deoxy-beta-D-glucopyranoside hydrochloride and its derivatives," *Carb. Res.*, 338:133-141, 2003.
Nakae and Nakae, "Diffusion of aminoglycoside antibiotics across the outer membrane of *Escherichia coli*," *Antimicrobial Agents and Chemo.*, 22:554-559, 1982.
Ohtsuki et al., "Technetium-99m HYNIC-annexin V: a potential radiopharmaceutical for the in-vivo detection of apoptosis," *Eur. J. Nucl. Med.*, 26:1251-1258, 1999.
Ozmen et al., "Effects of some antibiotics on activity of glucose-6-phosphate dehydrogenase from human erythrocytes in vitro and effect of isepamicin sulfate on activities of antioxidant enzymes in rat erythrocytes," *Drug Chem. Toxicol.*, 28:433-445, 2005.
Panneerselvam et al., "(12-hydroxymethyl-5,5 ,7,12,14-pentamethyl-1,4,8,11-tetraazacyclo-tetradecane-$N$-acetato-$N,N',N'',N''',O,O'$)cobalt(III) chloride perchlorate monohydrate," *Acta Crystallogr.,C* 56:659-660, 2000.
Philpott et al., "RadioimmunoPET: detection of colorectal carcinoma with positron-emitting copper-64-labeled monoclonal antibody," *J. Nucl. Med.*, 36:1818-1824, 1995.
Pohost et al., "Differentiation of transiently ischemic from infarcted myocardium by serial imaging after a single dose of thallium-201 ," *Circulation*, 55:294-302, 1977.
Ranganathan et al., "Polymethylated DOTA ligands. 2. synthesis of rigified lanthanide chelates and studies on the effect of alkyl substitution on conformational mobility and relaxivity," *Inorg. Chem.*, 41:6856-6866, 2002.
Ruegg et al., "Improved in vivo stability and tumor targeting of bismuth-labeled antibody," *Cancer research*, 50:4221-4226, 1990.
Schechter et al., "Assessment of epidermal growth factor receptor with 99mTc-ethylenedicysteine-C225 monoclonal antibody," *Anti-cancer Drugs*, 14:49-56, 2003.
Schechter et al., "Radiation dosimetry of 99mTc-labeled C225 in patients with squamous cell carcinoma of the head and neck," *J. Nucl. Med.*, 45:1683-1687.
Sharkey et al., "Radioimmunotherapy of Non-Hodgkin's lymphoma with $^{90}$Y-DOTA humanized anti-CD22 IgG ($^{90}$Y-Epratuzumab): do tumor targeting and dosimetry predict therapeutic response?" *J. Nucl. Med.*, 44:2000-2018, 2003.
Silverman et al., "Evaluating tumor biology and oncological disease with positron-emission tomography," *Seminars in Radiation Oncology*, 8:183-196, 1998.
Smith et al., "Radiochemical investigations of $^{177}$Lu-DOTA-8-Aoc-BBN[7-14]$NH_2$: an in vitro/in vivo assessment of the targeting ability of this new radiopharmaceutical for PC-3 human prostate cancer cells," *Nuclear Medicine and Biol.*, 30:101-109, 2003.
Song et al., "Prognostication of recovery in patients with acute ischemic stroke through the use of brain SPECT with Technetium-99m-labeled metronidazole," *Stroke*, 34:982-986, 2003.
Srivastava et al., "Comparative evaluation of chelating agents on the mobilization of cadmium: a mechanistic approach," *J. Toxicology and Environmental Health*, 47:173-182, 1996.
Stein et al., "Radioimmunotherapy of a human lung cancer xenograft with monoclonal antibody RS7: evaluation of $^{177}$Lu and comparison of its efficacy with that of $^{90}$Y and residualizing $^{131}$I," *J. Nucl. Med.*, 42:967-974, 2001.
Tachibana et al., "Inhibitory effects of kanamycin on glycolysis in cochlea and kidney—possible involvement in the formation of oto- and nephrotoxicities," *Biochem. Pharmacol.*, 25:2297-2301, 1976.
Tod et al., "Clinical pharmacokinetics and pharmacodynamics of isepamicin," *Clin. Pharmacokinet.*, 38:205-223, 2000.
Vogler et al., "Pre-clinical evaluation of gadobutrol: a new, neutral, extracellular contrast agent for magnetic resonance imaging," *Eur. J. Radiol.*, 21:1-10, 1995.
Vriens et al., "The use of technetium $^{99m}$Tc annexin V for in vivo imaging of apoptosis during cardiac allograft rejection," *J. Thorac. Cardiovasc. Surg.*, 116:844-853,1998.
Wang et al., "$[Cu(L)Mn(N_3)_2]_n$: the first complex containing both macrocyclic oxamido and alternate (mu-1,1 and mu-1,3) azido bridges," *Inorg. Chem.*, 43:852-854, 2004.
Wester et al., "Synthesis and radiopharmacology of O-(2-[18F]fluoroethyl)-L-tyrosine for tumor imaging," *J. Nucl. Med.*, 40:205-212, 1999.
Wu et al., "High-resolution microPET imaging of carcino-embryonic antigen-positive xenografts by using a copper-64-labeled engineered antibody fragment," *Proc. Nat. Acad. Sci. USA*, 97:8495-8500, 2000.
Wu et al., "Investigations of N-linked macrocycles for 111In and 90Y labeling of proteins," *Nucl. Med. & Biol.*, 19:239-244, 1992.
Wu et al., "Using Tc-99m DMSA renal cortex scan to detect renal damage in women with type 2 diabetes," *J. Diabetes Complications*, 17:297-300, 2003.
Yanai et al., "Amplification of the entire kanamycin biosynthetic gene cluster during empirical strain improvement of *Streptomyces kanamyceticus*," *Proc. Natl. Acad. Sci. USA*, 103:9661-9666, 2006.
Yang and Kim, "Tracer development and hybrid imaging," *Eur. J. Nucl. Med. Mol. Imaging*, 32:1001-1002, 2005.
Yang et al., "(99m)Tc-EC-guanine: synthesis, biodistribution, and tumor imaging in animals," *Pharm. Res.*, 22:1471-1479, 2005.
Yang et al., "Assessment of antiangiogenic effect using 99mTc-EC-endostatin," *Cancer Biother. Radiopharm.*, 17:233-245, 2002.
Yang et al., "Assessment of cyclooxygense-2 expression with 99mTc-labeled celebrex," *Anticancer drugs*, 15:255-263, 2004.
Yang et al., "Imaging with 99mTc ECDG targeted at the multifunctional glucose transport system: feasibility study with rodents," *Radiology*, 226:465-473, 2003.
Yang et al., "In vivo and in vitro measurement of apoptosis in breast cancer cells using (99m)Tc-EC-annexin V," *Cancer Biotherapy*, 16:73-83, 2001.
Yang et al., "Metabolic pathways that mediate inhibition of hypothalamic neurons by glucose," *Diabetes*, 53:67-73, 2004.
Yang et al., "Targeted molecular imaging in oncology," *Ann. Nucl. Med.*, 20:1-11, 2006.
Zhang et al., "A ferromagnetically coupled $CrCu_3$ tetramer and $GdCu_4$ pentamer with a $[15]N_4$ macrocylic ligand incorporating an oxamido bridge," *Inorg. Chem.*, 42:1462-1466, 2003.
Zhao et al., "Effects of Dextranation on the pharmacokinetics of short peptides. a PET study on mEGF," *Bioconjugate Chem.*, 10:938-946, 1999.
Zhou et al., "Efficient intracellular delievery of oligonucleotides formulated in folate receptor-targeted lipid vesicles," *Bioconjugate Chem.*, 13:1220-1225, 2002.
Ozaki et al., "Assesment of tumor imaging using $^{99m}$Tc-LA-beled guanine analogue," *The Journal of Nuclear Medicine*, 44(Suppl. 5):298P(Abstract 1067), 2003.
Office Action issued in Japanese Application 2004-552132 (related to U.S. Appl. No. 11/770,395) dated Mar. 17, 2009 (English Translation).

(56) References Cited

OTHER PUBLICATIONS

Office Action, issued in U.S. Appl. No. 11/627,299, mail date May 29, 2008.
Office Action, issued in U.S. Appl. No. 11/627,299, mail date Feb. 25, 2009.
Office Action, issued in U.S. Appl. No. 11/760,456, mail date Jul. 8, 2008.
Office Action, issued in U.S. Appl. No. 11/760,456, mail date Nov. 13, 2008.
Office Action, issued in U.S. Appl. No. 11/405,334, mail date Mar. 27, 2008.
Office Action, issued in U.S. Appl. No. 11/405,334, mail date Dec. 11, 2008.
Office Action, issued in U.S. Appl. No. 11/405,334, mail date Mar. 18, 2009.
Qu et al., "Technetium-99m labeling on monoclonal antibodies via N,N'-ethylen-bis-L-cysteine," *Radiochimica Acta*, 63:209-212, 1993.
Office Action issued in Japanese Application 2004-552132, mailed Sep. 9, 2009. (English Translation).
Young et al., "Influence of immunoglobulin heavy and light-chain expression on B-cell differentiation," *Genes Develop.*, 8:1043-1057, 1994.
Zakko et al., "Biliary excretion of Tc-$^{99m}$ec in renal studies," *Clinical Nuclear Medicine*, 23:417-419, 1998.
Zareneyrizi et al., "Synthesis of [$^{99m}$Tc] ethylenedicysteine-colchicine for evaluation of antiangiogenic effect," *Anti-Cancer Drugs*, 10:685-692, 1999.

\* cited by examiner

NMR Spectra Data of EC-celecoxib-Ester

| Observed (ppm) | |
|---|---|
| 7.86 (2H, d, J=8.6Hz) | f |
| 7.33 (2H, d, J=8.6Hz) | e |
| 7.03 (2H, d, J=8.2Hz) | c |
| 6.98 (2H, d, J=8.2Hz) | b |
| 6.62 (1H, s) | d |
| 4.41 (2H, s) | g |
| 4.01 (2H, q, J=7.1Hz) | h |
| 2.22 (3H, s) | a |
| 1.11 (3H, t, J=7.1Hz) | i |

NMR Spectra Data of EC-celecoxib

| Observed (ppm) | |
|---|---|
| 7.83 (2H, d, J=8.6Hz) | f |
| 7.27 (2H, d, J=8.6Hz) | e |
| 7.03-7.09 (4H, m) | c,b |
| 6.68 (1H, s) | d |
| 3.56 (2H, br) | g |
| 3.38 (2H, br) | h |
| 2.94 (2H, br) | i |
| 2.26 (3H, s) | a |

FIG. 15

Scintigraphic Images of $^{99m}$Tc-EC-LHRH $^{99m}$Tc-EC-LHRH 0.5        2hrs $^{99m}$Tc-EC 0.5        2hrs

Synthesis of $^{99m}$Tc-Fullerene-EC-Drug Conjugates

$N_2S_2$ CHELATE-TARGETING LIGAND CONJUGATES

The benefit of the filing date of U.S. application Ser. No. 10/703,405, filed Nov. 7, 2003, and entitled "Ethylenedicysteine (EC)-Drug Conjugates, Compositions, and Methods for Tissue-Specific Disease Imaging" by David J. Yang, et al., which application in turn claims the benefit of U.S. provisional patent application Ser. No. 60/424,493, filed Nov. 7, 2002, is hereby claimed under 35 U.S.C. §120. The entire contents of U.S. application Ser. No. 10/703,405, filed Nov. 7, 2003, entitled "Ethylenedysteine (EC)-Drug Conjugates, Compositions, and Methods for Tissue-Specific Disease Imaging" by David J. Yang, et al., and the entire contents of U.S. provisional patent application Ser. No. 60/424,493, filed Nov. 7, 2002, are hereby specifically incorporated by reference.

BACKGROUND OF THE INVENTION

I. Field of the Invention

The present invention relates generally to the fields of labeling, radioimaging, radioimmunotherapy, and chemical synthesis. More particularly, it concerns a strategy for radiolabeling target ligands. It further concerns methods of using those radiolabeled ligands to target tumor angiogenesis, hypoxia, apoptosis, disease receptors, disease functional pathways, and disease cell cycles, as well as for the assessment of pharmaceutical agent effectiveness on these biochemical processes.

II. Description of Related Art

Angiogenesis, the proliferation of endothelial and smooth muscle cells to form new blood vessels, is an essential component of the metastatic pathway. These vessels provide the principal route by which certain cells exit the primary tissue site and enter the circulation. For many disease tissue, the vascular density can provide a prognostic indicator of metastatic potential or survival, with highly vascularized tumors having a higher incidence of metastasis than poorly vascularized tissues (Bertolini et al., 1999; Cao, 1999; Smith et al, 2000).

It may be feasible to block angiogenesis and tumor progression by using anti-angiogenic agents. At present, antiangiogenic agents under clinical testing include: naturally occurring inhibitors of angiogenesis (e.g. angiostatin, endostatin, platelet factor-4), (Jiang et al., 2001; Dhanabal et al., 1999; Moulton et al., 1999; Jouan et al., 1999) specific inhibitors of endothelial cell growth (e.g. TNP-470, thalidomide, interleukin-12), (Logothetis et al., 2001; Moreira et al., 1999; Duda et al., 2000) agents neutralizing angiogenic peptides (e.g. antibodies to fibroblast growth factor or vascular endothelial growth factor, suramin and analogues, tecogalan) (Bocci et al., 1999; Sakamoto et al., 1995) or their receptors, (Pedram et al., 2001) agents that interfere with vascular basement membrane and extracellular matrix (e.g. metalloprotease inhibitors, angiostatic steroids), (Lozonschi et al., 1999; Maekawa et al., 1999; Banerjeei et al., 2000) anti-adhesion molecules, (Liao et al., 2000) antibodies such as anti-integrin $\alpha_v\beta_3$, (Yeh et al., 2001) and miscellaneous drugs that modulate angiogenesis by diverse mechanisms of action (Gasparini 1999).

For example many malignant tumors are angiogenesis-dependent. Several experimental studies suggest that primary tumor growth, invasiveness and metastasis require neovascularization (Sion-Vardy et al., 2001; Guang-Wu et al., 2000; Xiangming et al., 1998). Tumor-associated angiogenesis is a complex, multi-step process under the control of positive and negative soluble factors. Acquisition of the angiogenic phenotype is a common pathway for tumor progression, and active angiogenesis is associated with molecular mechanisms leading to tumor progression (Ugurel et al., 2001). For instance, vascular endothelial growth factor (VEGF) is a mitogen, morphogen and chemoattractant for endothelial cells and, in vivo, is a powerful mediator of vessel permeability (Szus et al., 2000). Interleukin-8 (IL-8) is a chemo-attractant for neutrophils and is a potent angiogenic factor (Petzelbauer et al., 1995). Basic fibroblast growth factor (bFGF) has been associated with tumorigenesis and metastasis in several human cancers (Smith et al., 1999). The prognostic value of angiogenesis factor expression (e.g. VEGF, bFGF, microvessel density, IL-8, MMP-2 and MMP-9) has been determined for cancer patients treated with chemotherapy (Inoue et al., 2000; Burian et al., 1999). These factors regulate metastasis and angiogenesis and may predict the metastatic potential in individual cancer patients (Slaton et al., 2001).

Apoptosis defects in programmed cell death play an important role in tumor pathogenesis. These defects allow neoplastic cells to survive beyond their normal intended lifespan, and subvert the need for exogenous survival factors. Apoptosis defects also provide protection from hypoxia and oxidative stress as the tumor mass expands. They also allow time for genetic alterations that deregulate cell proliferation to accumulate, resulting in interference with differentiation, angiogenesis, and increased cell motility and invasiveness during tumor progression (Reed, 1999). In fact, apoptosis defects are recognized as an important complement to protooncogene activation, as many deregulated oncoproteins that drive cell division also trigger apoptosis (Green and Evan, 2002). Similarly, defects in DNA repair and chromosome segregation normally trigger cell suicide as a defense mechanism for readicating genetically unstable cells. Thus, apoptosis defects permit survival of genetically unstable cells, providing opportunities for selection of progressively aggressive clones (Ionov et al., 2000). Apoptosis defects also facilitate metastasis by allowing epithelial cells to survive in a suspended state, without attachment to extracellular matrix (Frisch and Screaton, 2001). They also promote resistance to the immune system, inasmuch as many of the weapons used for attacking tumors, including cytolytic T cells (CTLs) and natural killer (NK) cells, depend on the integrity of the apoptosis machinery (Tschopp et al., 1999). Finally, cancer-associated defects in apoptosis play a role in chemoresistance and radioresistance, increasing the threshold for cell death and thereby requiring higher doses for tumor killing (Makin and Hickman, 2000). Thus, defective apoptosis regulation is a fundamental aspect of the biology of cancer.

When it comes to the successful eradication of cancer cells by nonsurgical means, all roads ultimately lead to angiogenesis and apoptosis. Essentially all cytotoxic anticancer drugs currently in clinical use block angiogenesis and induce apoptosis of malignant cells. While microtubule binding drugs, DNA-damaging agents, and nucleosides are important weapons in the treatment of cancer, new classes of targeted therapeutics may soon be forthcoming. These new classes of targeted therapeutics may soon be forthcoming based on strategies that have emerged from a deeper understanding of the molecular mechanisms that underlie the phenomenon of angiogenesis and apoptosis (Reed, 2003).

Though angiogenic and apoptotic factors reflect angiogenesis and apoptosis status, these agents may not adequately reflect the therapeutic response of tumors. Currently, methods of assessing angiogenesis and apoptosis in tumors rely on counting microvessel density in the areas of neovascularization and observing annexin V with FACS techniques. After tissue biopsy, immunohistochemistry of tissue specimen is then performed. Both techniques are invasive and cannot be repeatedly performed.

Improvement of scintigraphic tumor imaging is extensively determined by development of more tumor specific radiopharmaceuticals. Due to greater tumor specificity, radiolabeled ligands as well as radiolabeled antibodies have opened a new era in scintigraphic detection of tumors and undergone extensive preclinical development and evaluation (Mathias et al., 1996, 1997a, 1997b). Radionuclide imaging modalities (positron emission tomography, PET; single photon emission computed tomography, SPECT) are diagnostic cross-sectional imaging techniques that map the location and concentration of radionuclide-labeled radiotracers. Although CT and MRI provide considerable anatomic information about the location and the extent of tumors, these imaging modalities cannot adequately differentiate invasive lesions from edema, radiation necrosis, grading or gliosis. PET and SPECT can be used to localize and characterize tumors by measuring metabolic activity.

[$^{18}$F]FMISO has been used to diagnose head and neck tumors, myocardial infarction, inflammation, and brain ischemia (Martin et al. 1992; Yeh et al. 1994; Yeh et al. 1996; Liu et al. 1994). Tumor to normal tissue uptake ratio was used as a baseline to assess tumor hypoxia (Yet et al. 1996). Although tumor metabolic imaging using [$^{18}$F]FDG was clearly demonstrated, introducing molecular imaging agents into clinical practice depends on some other factors such as easy availability and isotope cost. [$^{18}$F]fluorodeoxyglucose (FDG) has been used to diagnose tumors, myocardial infarction, and neurological disease. In addition, PET radiosynthesis must be rapid because of short half-life of the positron isotopes. $^{18}$F chemistry is complex and is not reproducible in different molecules.

Several compounds have been labeled with $^{99m}$Tc using nitrogen and sulfur chelates (Blondeau et al., 1967; Davison et al., 1980). Bis-aminoethanethiol tetradentate ligands, also called diaminodithol compounds, are known to form very stable Tc(V)O complexes on the basis of efficient binding of the oxotechnetium group to two thiol sulfur and two amine nitrogen atoms. Radiometal complexes of 2-pyrrolthiones labeled with $^{99m}$Tc-2-pyrrolthiones complexes have been developed for use as radiopharmaceuticals for imaging and therapy (WO 0180906A2). $^{99m}$Tc-L,L-ethylenedicysteine ($^{99m}$Tc-EC) is a recent and successful example of N$_2$S$_2$ chelates. EC can be labeled with $^{99m}$Tc easily and efficiently with high radiochemical purity and stability, and is excreted through the kidney by active tubular transport (Surma et al., 1994; Van Nerom et al., 1990, 1993; Verbruggen et al., 1990, 1992). Furthermore, $^{99m}$Tc chelated with ethylenedicysteine (EC) and conjugated with a variety of ligands has been developed for use as an imaging agent for tissue-specific diseases, a prognostic tool or as a tool to deliver therapeutics to specific sites within a mammalian body (WO 0191807A2, AU 0175210A5). $^{99m}$Tc-EC-chelates have been developed for renal imaging and examination of renal function (U.S. Pat. No. 5,986,074 and U.S. Pat. No. 5,955,053). A method of preparing $^{99m}$Tc-EC complexes and a kit for performing said method has also been developed (U.S. Pat. No. 5,268,163 and WO 9116076A1).

However, there still exist a need for the development of new agents to target tumor angiogenesis, hypoxia, apoptosis defects, disease receptors, disease functional pathways, and disease cell cycles, as well as for the assessment of the pharmaceutical agent effectiveness on these biochemical processes.

SUMMARY OF THE INVENTION

Certain embodiments of the present invention are generally concerned with compounds that comprises an N$_2$S$_2$ chelate conjugated to a targeting ligand, wherein the targeting ligand is a disease cell cycle targeting compound, a tumor angiogenesis targeting ligand, a tumor apoptosis targeting ligand, a disease receptor targeting ligand, amifostine, angiostatin, an EGF receptor ligand, monoclonal antibody C225, monoclonal antibody CD31, monoclonal antibody CD40, capecitabine, a COX-2 inhibitor (hereinafter referred to throughout this application as "COX-2"), deoxycytidine, fullerene, herceptin, human serum albumin, lactose, leuteinizing hormone, pyridoxal, quinazoline, thalidomide, transferrin, or trimethyl lysine. In certain embodiments of the present invention, the N$_2$S$_2$ chelate is a bis-aminoethanethiol (BAT)-targeting chelate. For example, a particularly preferred BAT-targeting chelate is ethylenedicysteine. In certain embodiments, the N$_2$S$_2$ chelate conjugated to a targeting ligand is radiolabeled with a radioactive nuclide. For example, the radioactive nuclide may be $^{99m}$Tc, $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu.

A particular aspect of the invention comprises an N$_2$S$_2$ chelate compound of the formula:

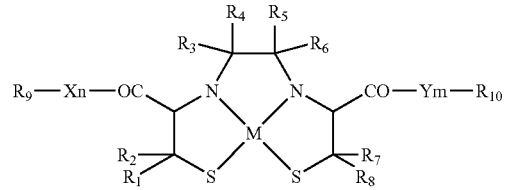

wherein R$_1$, R$_2$, R$_3$, R$_4$, R$_5$, R$_6$, R$_7$ and R$_8$ are independently H or CH$_3$; R$_9$ is H, CH$_3$, a disease cell cycle targeting compound, amifostine, angiostatin, anti-EGF receptor a tumor angiogenesis targeting ligand, a tumor apoptosis targeting ligand, a disease receptor targeting ligand, monoclonal antibody CD31, monoclonal antibody CD40, capecitabine, COX-2, deoxycytidine, fullerene, herceptin, human serum albumin, lactose, luteinizing hormone, pyridoxal, quinazoline, thalidomide, transferrin, or trimethyl lysine; R$_{10}$ is H, CH$_3$, disease cell cycle targeting compound, amifostine, angiostatin, anti-EGF receptor, monoclonal antibody CD31, monoclonal antibody CD40, capecitabine, COX-2, deoxycytidine, fullerene, herceptin, human serum albumin, lactose, luteinizing hormone, pyridoxal, quinazoline, thalidomide, transferrin, or trimethyl lysine; n is 0 or 1; m is 0 or 1; X is a water soluble peptide, C$_1$-C$_{20}$ alkyl, glutamic acid, polyglutamic acid, aspartic acid, polyaspartic acid, bromoethylacetate, ethylenediamine or lysine when n is 1, or a bond when n is 0; Y is a water soluble peptide, C$_1$-C$_{20}$ alkyl, glutamic acid, polyglutamic acid, aspartic acid, polyaspartic acid, bromoethylacetate, ethylenediamine or lysine when m is 1, or a bond when m is 0; and M is $^{99m}$Tc, $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu.

In a particular embodiment of the compound as previously described, R$_9$ and R$_{10}$ are independently H, CH$_3$, COX-2, anti-EGF receptor, herceptin, angiostatin, or thalidomide; and M is $^{99m}$Tc. In certain embodiments, COX-2 is celecoxib. One of ordinary skill in the art would be familiar with celecoxib, rofecoxib, etoricoxib, and similar agents that inhibit the COX-2 enzyme which can be used as ligands in the present compounds.

In another preferred embodiment of the compound as previously described, said disease cell cycle targeting compound is FIAU, FIRU, IVFRU, GCV, PCV, FGCV, FHPG, FHBG, adenosine or penciclovir (guanine). These disease cell cycle targeting compounds are discussed in greater detail in the specification below.

Angiogenesis targeting refers to the use of an agent to bind to neovascularization, such as neovascularization of tumor cells. This is discussed in greater detail in the specification below. Agents that are used for this purpose are known to those of ordinary skill in the art for use in performing various tumor measurements, including measurement of the size of a tumor vascular bed, and measurement of tumor volume. Some of these agents bind to the vacular wall. One of ordinary skill in the art would be familiar with the agents that are available for use for this purpose. Examples include COX-2, anti-EGF receptor ligands, herceptin, angiostatin, and thalidomide.

Tumor apoptosis targeting refers to use of an agent to bind to a cell that is undergoing apoptosis or at risk of undergoing apoptosis. These agents are generally used to provide an indicator of the extent or risk of apoptosis, or programmed cell death, in a population of cells, such as a tumor. One of ordinary skill in the art would be familiar with agents that are used for this purpose. Examples include TRAIL (tumor necrosis factor-related apoptosis inducing ligand) monoclonal antibody, caspase-3 substrate (for example, a peptide or polypeptide that includes the amino acid sequence aspartic acid-glutamic acid-valine-aspartic acid), and any member of the Bcl family. Examples of Bcl family members include, for example, Bax, Bcl-xL, Bid, Bad, Bak, and Bcl-2). One of ordinary skill in the art would be familiar with the Bcl family, and their respective substrates. Tumor apoptosis targeting is discussed in greater detail in the specification below.

In disease receptor targeting, certain ligands are exploited for their ability to bind to particular cellular receptors that are overexpressed in disease states, such as cancer. Examples of such receptors which are targeted include estrogen receptors, androgen receptors, pituitary receptors, transferrin receptors, and progesterone receptors. One of ordinary skill in the art would be familiar with these and other receptors which can be targeted in disease states. Disease receptor targeting is discussed in greater detail in the specification below.

Disease cell cycle targeting refers to targeting of agents that are upregulated in proliferating cells. Compounds used for this purpose can be used to measure various parameters in cells, such as tumor cell DNA content. Many of these agents are nucleoside analogues. Further discussion pertaining to disease cell cycle targeting is provided in the specification below.

Certain drug-based ligands of the present invention can be applied in measuring the pharmacological response of a subject to a drug. Examples include carnitine and puromycin. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject. Radiolabeled agents can be applied in measuring drug assessment. Further discussion pertaining to drug assessment is provided in other parts of this specification.

Another aspect of the current invention comprises a method of synthesizing a radiolabeled $N_2S_2$ derivative for imaging comprising the steps: obtaining a compound in accordance with the above description of an $N_2S_2$ chelate conjugated to a targeting ligand, and admixing the compound with a radionuclide labeled derivative, wherein the $N_2S_2$ chelate forms a chelate with the radionuclide.

In certain embodiments of the present invention, the $N_2S_2$ chelate is a bis-aminoethanethiol (BAT)-targeting chelate. For example, a particularly preferred BAT-targeting chelate is ethylenedicysteine.

In certain embodiments, the reducing agent may be a dithionite ion, a stannous ion or a ferrous ion. In some embodiments, the radionuclide is $^{99m}Tc$, $^{188}Re$, $^{186}Re$, $^{183}Sm$, $^{166}Ho$, $^{90}Y$, $^{89}Sr$, $^{67}Ga$, $^{68}Ga$, $^{111}In$, $^{183}Gd$, $^{59}Fe$, $^{225}Ac$, $^{212}Bi$, $^{211}At$, $^{45}Ti$, $^{60}Cu$, $^{61}Cu$, $^{67}Cu$, $^{64}Cu$ or $^{62}Cu$.

In yet another embodiment, the disease cell cycle targeting compound is adenosine or penciclovir (guanine).

Another aspect of the current invention comprises a method of imaging a site within a mammalian body that includes the steps of administering an effective amount of an $N_2S_2$ chelate-targeting ligand conjugate to the site and detecting a radioactive signal from the compound localized at the site. The previous description pertaining to $N_2S_2$ chelate-targeting ligand conjugates applies to these methods. In certain embodiments of the present invention, the $N_2S_2$ chelate is a bis-aminoethanethiol (BAT)-targeting chelate. For example, a particularly preferred BAT-targeting chelate is ethylenedicysteine.

In certain embodiments of the present methods of imaging a site within a mammalian body, the $N_2S_2$ chelate compound is of the formula:

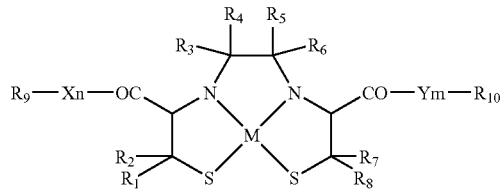

wherein $R_1$, $R_2$, $R_3$, $R_4$, $R_5$, $R_6$, $R_7$ and $R_8$ are independently H or $CH_3$; $R_9$ is H, $CH_3$, a disease cell cycle targeting compound, a tumor angiogenesis targeting ligand, a tumor apoptosis targeting ligand, a disease receptor targeting ligand, amifostine, angiostatin, anti-EGF receptor, monoclonal antibody CD31, monoclonal antibody CD40, capecitabine, COX-2, deoxycytidine, fullerene, herceptin, human serum albumin, lactose, leuteinizing hormone, pyridoxal, quinazoline, thalidomide, transferrin, or trimethyl lysine; $R_{10}$ is H, $CH_3$, a disease cell cycle targeting compound, amifostine, angiostatin, anti-EGF receptor, monoclonal antibody CD31, monoclonal antibody CD40, capecitabine, COX-2, deoxycytidine, fullerene, herceptin, human serum albumin, lactose, leuteinizing hormone, pyridoxal, quinazoline, thalidomide, transferrin, or trimethyl lysine; n is 0 or 1; m is 0 or 1; X is a water soluble peptide, $C_1$-$C_{20}$ alkyl, glutamic acid, polyglutamic acid, aspartic acid, polyaspartic acid, bromoethylacetate, ethylenediamine or lysine when n is 1, or a bond when n is 0; Y is a water soluble peptide, $C_1$-$C_{20}$ alkyl, glutamic acid, polyglutamic acid, aspartic acid, polyaspartic acid, bromoethylacetate, ethylenediamine or lysine when m is 1, or a bond when m is 0; M is $^{99m}Tc$, $^{188}Re$, $^{186}Re$, $^{183}Sm$, $^{166}Ho$, $^{90}Y$, $^{89}Sr$, $^{67}Ga$, $^{68}Ga$, $^{111}In$, $^{183}Gd$, $^{59}Fe$, $^{225}Ac$, $^{212}Bi$, $^{211}At$, $^{45}Ti$, $^{60}Cu$, $^{61}Cu$, $^{67}Cu$, $^{64}Cu$ or $^{62}Cu$; and b) detecting a radioactive signal from said compound localized at a site. In some embodiments, M is $^{99m}$Tc. The disease cell cycle targeting compound may be adenosine, penciclovir (guanine), FIAU, FIRU, IVFRU, GCV, PCV, FGCV, FPCV, FHPG, or FHBG. The discussion above pertaining to disease cell cycle targeting compounds, tumor angiogenesis targeting ligands, tumor apoptosis targeting ligands, and disease receptor targeting ligands also applies to this section and other sections of the summary.

The site may be a tumor, an infection, breast cancer, ovarian cancer, prostate cancer, endometrium, heart cancer, lung cancer, brain cancer, liver cancer, folate (+) cancer, ER (+) cancer, spleen cancer, pancreas cancer, or intestine cancer.

Yet another aspect of the invention comprises a kit for preparing a radiopharmaceutical preparation comprising: a) a sealed container including a predetermined quantity of a compound that is a $N_2S_2$ chelate-targeting ligand conjugate in accordance with the $N_2S_2$ chelates conjugated to a targeting ligand as discussed above, and a sufficient amount of a reducing agent. In certain embodiments of the present invention, the $N_2S_2$ chelate is a bis-aminoethanethiol (BAT)-targeting chelate. For example, a particularly preferred BAT-targeting chelate is ethylenedicysteine.

In certain embodiments, the kit further comprises a radionuclide. For example, the radionuclide may be $^{99m}$Tc, $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu.

In certain particular embodiments, the compound is of the formula:

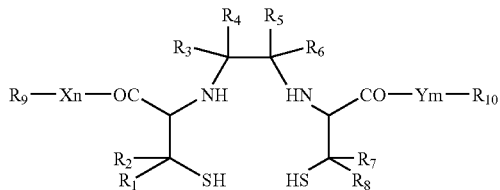

wherein R1, R2, R3, R4, R5, R6, R7 and R8 are independently H or CH3; R9 is H, CH3, a disease cell cycle targeting compounda tumor angiogenesis targeting ligand, a tumor apoptosis targeting ligand, a disease receptor targeting ligand, amifostine, angiostatin, anti-EGF receptor, monoclonal antibody CD31, monoclonal antibody CD40, capecitabine, COX-2, deoxycytidine, fullerene, herceptin, human serum albumin, lactose, leuteinizing hormone, pyridoxal, quinazoline, thalidomide, transferrin, or trimethyl lysine; R10 is H, CH3, a disease cell cycle targeting compound, amifostine, angiostatin, anti-EGF receptor, monoclonal antibody CD31, monoclonal antibody CD40, capecitabine, COX-2, deoxycytidine, fullerene, herceptin, human serum albumin, lactose, leuteinizing hormone, pyridoxal, quinazoline, thalidomide, transferrin, or trimethyl lysine; n is 0 or 1; m is 0 or 1; X is a water soluble peptide, $C_1$-$C_{20}$ alkyl, glutamic acid, polyglutamic acid, aspartic acid, polyaspartic acid, bromoethylacetate, ethylenediamine or lysine when n is 1, or a bond when n is 0; Y is a water soluble peptide, C1-C20 alkyl, glutamic acid, polyglutamic acid, aspartic acid, polyaspartic acid, bromoethylacetate, ethylenediamine or lysine when m is 1, or a bond when m is 0; and b) a sufficient amount of a reducing label conjugated with $^{99m}$Tc, $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu. The reducing label may be conjugated with $^{99m}$Tc. The disease cell cycle targeting compound may be adenosine or penciclovir or any disease cell cycle targeting compound known to those of ordinary skill in the art.

An aspect of the current invention comprises a reagent for preparing a scintigraphic imaging agent comprising an $N_2S_2$ chelate conjugated to a targeting ligand, in accordance with the description discussed above in this summary. In certain embodiments of the present invention, the $N_2S_2$ chelate is a bis-aminoethanethiol (BAT)-targeting chelate. For example, a particularly preferred BAT-targeting chelate is ethylenedicysteine.

In certain examples of the present invention, the $N_2S_2$ chelate is of the formula:

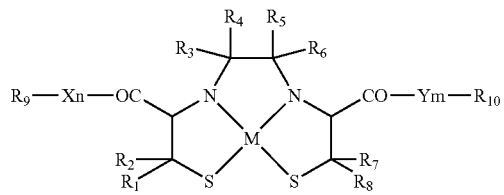

wherein $R_1$, $R_2$, $R_3$, $R_4$, $R_5$, $R_6$, $R_7$ and $R_8$ are independently H or $CH_3$; $R_9$ is H, $CH_3$, a disease cell cycle targeting compound, a tumor angiogenesis targeting ligand, a tumor apoptosis targeting ligand, a disease receptor targeting ligand, amifostine, angiostatin, anti-EGF receptor, monoclonal antibody CD31, monoclonal antibody CD40, capecitabine, COX-2, deoxycytidine, fullerene, herceptin, human serum albumin, lactose, leuteinizing hormone, pyridoxal, quinazoline, thalidomide, transferrin, or trimethyl lysine; $R_{10}$ is H, $CH_3$, a disease cell cycle targeting compound, a tumor angiogenesis targeting ligand, a tumor apoptosis targeting ligand, a disease receptor targeting ligand, amifostine, angiostatin, anti-EGF receptor, monoclonal antibody CD31, monoclonal antibody CD40, capecitabine, COX-2, deoxycytidine, fullerene, herceptin, human serum albumin, lactose, leuteinizing hormone, pyridoxal, quinazoline, thalidomide, transferrin, or trimethyl lysine; n is 0 or 1; m is 0 or 1; X is a water soluble peptide, $C_1$-$C_{20}$ alkyl, glutamic acid, polyglutamic acid, aspartic acid, polyaspartic acid, bromoethylacetate, ethylenediamine or lysine when n is 1, or a bond when n is 0; Y is a water soluble peptide, $C_1$-$C_{20}$ alkyl, glutamic acid, polyglutamic acid, aspartic acid, polyaspartic acid, bromoethylacetate, ethylenediamine or lysine when m is 1, or a bond when m is 0; and M is $^{99m}$Tc, $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu. M is preferably $^{99m}$Tc and the disease cell cycle targeting compound is preferably adenosine or penciclovir (guanine).

The present invention also pertains to methods of assessing the pharmacology of an agent of interest, comprising (1) preparing a conjugate of the agent to an $N_2S_2$ chelate, (2) adding a radioactive nuclide to said conjugated chelate to form a radioactive conjugate; (3) administering said radioactive conjugate to a subject; and (4) assessing the pharmacology of the agent. The agent of interest may be a pharmaceutical agent. The $N_2S_2$ chelate in certain embodiments is ethylenedicysteine. The subject may be any subject, such as a laboratory animal or a human. In certain embodiments, assessing the pharmacology of the agent comprises assessing the biodistribution of the agent, assessing the biostability of the agent, or assessing the bioelimination of the agent.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 15: NMR spectra data of EC-celecoxib. NMR spectra data of EA-celecoxib (compound (II)) are shown.

FIG. 43A: A: Gluconic Acid, B: Glucaric Acid; FIG. 43B: Cells were incubated with EC-DG and different concentration of Gluconic Acid (A). A1: 10%, A2: 20%, A3: 30%, A4: 50%; FIG. 43C: Cells were incubated with EC-DG and different concentration of Glucaric Acid (B). B1: 10%, B2: 20%, B3: 30%, B4: 50%.

DESCRIPTION OF ILLUSTRATIVE EMBODIMENTS

I. The Present Invention

Figure 1:
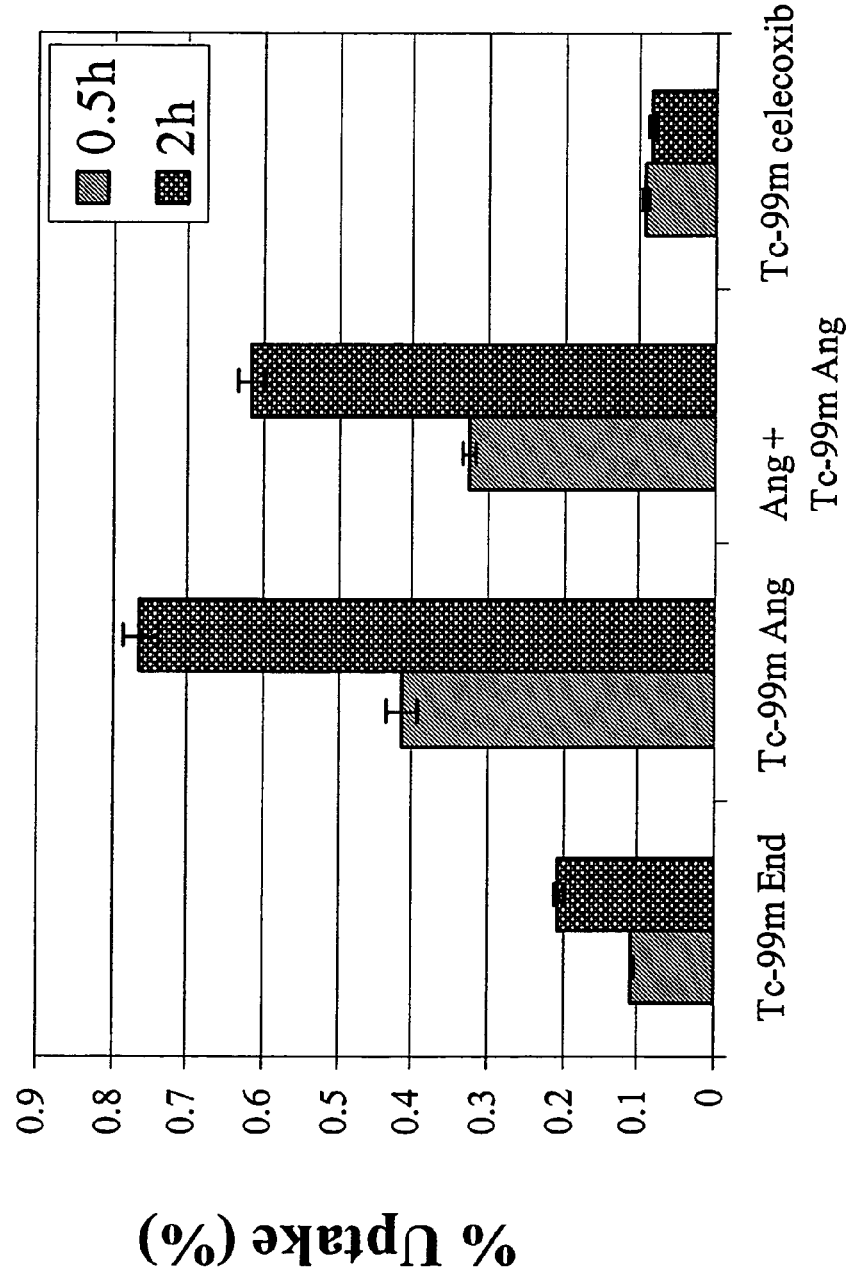
FIG. 1: In vitro cellular uptake of $^{99m}$Tc-EC-Angiostatin in breast cancer cells. Decreased uptake by adding unlabeled angiostatin is shown.

The present invention overcomes deficiencies in the art by providing novel $N_2S_2$-chelate targeting ligand conjugates designed to target tumor angiogenesis, hypoxia, apoptosis defects, disease receptors, disease function pathways, and disease cell cycles. The $N_2S_2$-chelate targeting ligand conjugates can also be used to assess the effectiveness of pharmaceutical agents on the biochemical processes stated above. More particularly, the present invention provides $N_2S_2$-chelate targeting ligand conjugates to target tumor angiogenesis, hypoxia, apoptosis defects, disease receptors, disease function pathways, and disease cell cycles, as well as for the assessment of a pharmaceutical agent effectiveness on these biochemical processes.

II. Radiopharmaceuticals

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

III. Radioimaging Methods

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

IV. Radionuclides

A variety of radionuclides are known to be useful for radioimaging and radioimmunotherapy, including $^{67}$Ga/$^{68}$Ga, $^{99m}$Tc, $^{111}$In, $^{123}$I, $^{125}$I, $^{169}$Yb or $^{186}$Re/$^{188}$Re. Due to better imaging characteristics and lower price, attempts have been made to replace or provide an alternative to $^{123}$I, $^{131}$I, $^{67}$Ga and $^{111}$In labeled compounds with corresponding $^{99m}$Tc labeled compounds when possible. Due to favorable physical characteristics as well as extremely low price ($0.21/mCi), $^{99m}$Tc is preferred to label radiopharmaceuticals. Although it has been reported that DTPA-drug conjugate could be labeled with $^{99m}$Tc effectively (Mathias et al., 1997), DTPA moiety does not chelate with $^{99m}$Tc as stable as with $^{111}$In (Goldsmith, 1997).

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. $^{99m}$Tc is a preferred radionuclide because it emits gamma radiation at 140 keV, it has a physical half-life of 6 hours, and it is readily available on-site using a molybdenum-99/technetium-99m generator.

V. Ethylenedicysteine

The present invention utilizes, in certain embodiments, $N_2S_2$ chelates which include EC. These compounds can be used to target tumor angiogenesis, hypoxia, apoptosis defects, disease receptors, disease functional pathways, and disease cell cycles, as well as for the assessment of a pharmaceutical agent's effectiveness on these biochemical processes.

The advantage of conjugating the EC with tissue targeting ligands is that the specific binding properties of the tissue targeting ligand concentrates the radioactive signal over the area of interest. It is envisioned that the use of $^{99m}$Tc-EC as a labeling strategy can be effective with ligands designed for targeting disease receptors, hypoxia, apoptosis pathways, disease cell cycles, disease functional pathways, radioimmunotherapy, and assessment of a pharmaceutical agent's effectiveness on these biochemical processes. Examples of certain embodiments for the present invention can be found in Table 1.

TABLE 1

| Targets for EC-Complex | Examples |
|---|---|
| Tumor Angiogenesis | $^{99m}$Tc-EC-celecoxib (EC-COX-2), $^{99m}$Tc-EC-C225, and $^{99m}$Tc-EC-angiostatin |
| Disease Receptor | $^{99m}$Tc-EC-luteinizing hormone ($^{99m}$Tc-EC-LH antibody), $^{99m}$Tc-EC-transferrin, $^{99m}$Tc-EC-somatostatin, $^{99m}$Tc-EC-androgen, $^{99m}$Tc-EC-estrogen, $^{99m}$Tc-EC-progesterone |
| Disease Cell Cycle | $^{99m}$Tc-EC-adenosine, and $^{99m}$Tc-EC-penciclovir ($^{99m}$Tc-EC-guanine) |
| Pharmaceutical Agent Assessment | $^{99m}$Tc-EC-carnitine, $^{99m}$Tc-EC-puromycin |
| Apoptosis Targeting | $^{99m}$Tc-EC-TRAIL mnoclonal antibody, $^{99m}$Tc-EC-caspase-3 substrate, $^{99m}$Tc-EC-Bcl family member |

VI. $^{99m}$Technetium-EC Complex $^{99m}$Tc is normally obtained as $^{99m}$Tc pertechnetate (TcO$_4^-$; technetium in the +7 oxidation state), usually from a molybdenum-99/technetium-99m generator. However, pertechnetate does not bind well with other compounds. Therefore, in order to radiolabel a compound, $^{99m}$Tc pertechnetate must be converted to another form. Since technetium does not form a stable ion in aqueous solution, it must be held in such solutions in the form of a coordination complex that has sufficient kinetic and thermodynamic stability to prevent decomposition and resulting conversion of $^{99m}$Tc either to insoluble technetium dioxide or back to pertechnetate.

For the purpose of radiolabeling, it is particularly advantageous for the $^{99m}$Tc complex to be formed as a chelate in which all of the donor groups surrounding the technetium ion are provided by a single chelating ligand—in this case, ethylenedicysteine. This allows the chelated $^{99m}$Tc to be covalently bound to a tissue specific ligand either directly or through a single linker between the ethylenedicysteine and the ligand.

Technetium has a number of oxidation states: +1, +2, +4, +5, +6 and +7. When it is in the +1 oxidation state, it is called Tc MIBI. Tc MIBI must be produced with a heat reaction (Seabold et al. 1999). For purposes of the present invention when using the N$_2$S$_2$ chelate, it is important that the Tc be in the +4 oxidation state. This oxidation state is ideal for forming the N$_2$S$_2$ chelate with EC. Thus, in forming a complex of radioactive technetium with the drug conjugates of the invention, the technetium complex, preferably a salt of $^{99m}$Tc pertechnetate, is reacted with the drug conjugates of the invention in the presence of a reducing agent.

The preferred reducing agent for use in the present invention is stannous ion in the form of stannous chloride (SnCl$_2$) to reduce the Tc to its +4 oxidation state. However, it is contemplated that other reducing agents, such as dithionate ion or ferrous ion may be useful in conjunction with the present invention. It is also contemplated that the reducing agent may be a solid phase reducing agent. The amount of reducing agent can be important as it is necessary to avoid the formation of a colloid. It is preferable, for example, to use from about 10 to about 100 μg SnCl$_2$ per about 100 to about 300 mCi of Tc pertechnetate. The most preferred amount is about 0.1 mg SnCl$_2$ per about 200 mCi of Tc pertechnetate and about 2 ml saline. This typically produces enough Tc-EC-tissue specific ligand conjugate for use in 5 patients.

It is often also important to include an antioxidant and a transition chelator in the composition to prevent oxidation of the ethylenedicysteine. The preferred antioxidant for use in conjunction with the present invention is vitamin C (ascorbic acid). However, it is contemplated that other antioxidants, such as tocopherol, pyridoxine, thiamine or rutin, may also be useful. Examples of transition chelators include glucoheptonate, gluconate, glucarate, citrate, and tartarate. In certain embodiments, the transition chelator is either gluconate or glucarate, neither of which interferes with the stability of ethylenedicysteine.

VII. EC Ligands

In certain embodiments of the present invention, the N$_2$S$_2$ ligand is an EC ligand. In general, the EC ligands for use in conjunction with the present invention will possess either amino or hydroxy groups that are able to conjugate to EC on either one or both acid arms. If amino or hydroxy groups are not available (e.g., acid functional group), a desired ligand may still be conjugated to EC and labeled with $^{99m}$Tc using the methods of the invention by adding a linker, such as ethylenediamine, amino propanol, diethylenetriamine, aspartic acid, polyaspartic acid, glutamic acid, polyglutamic acid, or lysine. Ligands contemplated for use in the present invention include, but are not limited to, angiogenesis/antiangiogenesis ligands, DNA topoisomerase inhibitors, glycolysis markers, antimetabolite ligands, apoptosis/hypoxia ligands, DNA intercalators, cell receptor markers, peptides, nucleotides, antimicrobials such as antibiotics or antifungals, organ specific ligands and sugars or agents that mimic glucose.

EC itself is water soluble. It is necessary that the EC-drug conjugate of the invention also be water soluble. Many of the ligands used in conjunction with the present invention will be water soluble, or will form a water soluble compound when conjugated to EC. If the tissue specific ligand is not water soluble, however, a linker which will increase the solubility of the ligand may be used. Linkers may attach to an aliphatic, aromatic alcohol, amine, peptide, carboxylic, peptide or any combination thereof. Linkers may be either poly amino acid (peptide), an amino acid, alanine arginine, asparagine, aspartate, cysteine, glutamate, glutamine, glycine, proline, serine, tyrosine, histidine, isoleucine, leucine, lysine, methionine, phenylalanine, threonine, tryptophan, valine or any combination thereof. More preferably linkers may be glutamic acid, aspartic acid, lysine or any combination thereof.

It is also envisioned that the EC-tissue specific ligand drug conjugates of the current invention may be chelated to other radionuclides and used for radionuclide therapy. Generally, it is believed that virtually any α, β-emitter, γ-emitter, or β, γ-emitter can be used in conjunction with the invention. Preferred α emitters include bismuth-213, astatine-211, and radium-223. Preferred β, γ-emitters include $^{166}$Ho, $^{188}$Re, $^{186}$Re, $^{153}$Sm, and $^{89}$Sr. Preferred β-emitters include $^{90}$Y and $^{225}$Ac. Preferred γ-emitters include $^{67}$Ga, $^{68}$Ga, $^{64}$Cu, $^{62}$Cu and $^{111}$In. Preferred α-emitters include $^{211}$At and $^{212}$Bi. It is also envisioned that para-magnetic substances, such as Gd, Mn, Cu or Fe can be chelated with EC for use in conjunction with the present invention.

VIII. Kit for Preparing N$_2$S$_2$ Complexes

Complexes and means for preparing such complexes are conveniently provided in a kit form including a sealed vial containing a predetermined quantity of a N$_2$S$_2$ chelate targeting ligand conjugate of the invention and a sufficient amount of reducing agent to label the conjugate with a radionuclide. In some embodiments of the present invention, the kit includes a radionuclide. In certain further embodiments, the radionuclide is $^{99m}$Tc.

$^{99m}$Tc labeled scintigraphic imaging agents according to the present invention can be prepared by the addition of an appropriate amount of $^{99m}$Tc or $^{99m}$Tc complex into a vial containing the EC-tissue specific ligand conjugate and reducing agent and reaction under conditions described in Example 1 hereinbelow. The kit may also contain conventional pharmaceutical adjunct materials such as, for example, pharmaceutically acceptable salts to adjust the osmotic pressure, buffers, preservatives, antioxidants, and the like.

In certain embodiments, an antioxidant and a transition chelator are included in the composition to prevent oxidation of the ethylenedicysteine. In certain embodiments, the antioxidant is vitamin C (ascorbic acid). However, it is contemplated that any other antioxidant known to those of ordinary skill in the art, such as tocopherol, pyridoxine, thiamine, or rutin, may also be used. Examples of transition chelators for use in the present invention include, but are not limited to, glucoheptonate, gluconate, glucarate, citrate, and tartarate. In certain embodiments of the present invention, the transition chelator is gluconate or glucarate, as these do not interfere with the stability of ethylenedicysteine. The components of the kit may be in liquid, frozen or dry form. In a preferred embodiment, kit components are provided in lyophilized form.

IX. Radioactively Labeled Reagents

Radioactively labeled reagents or conjugates provided by the present invention are provided having a suitable amount of radioactivity. In forming $^{99m}$Tc radioactive complexes, it is generally preferred to form radioactive complexes in solutions containing radioactivity at concentrations of from about 0.01 millicurie (mCi) to about 300 mCi per mL.

$^{99m}$Tc labeled scintigraphic imaging agents provided by the present invention can be used for visualizing sites in a mammalian body. In accordance with this invention, the $^{99m}$Tc labeled scintigraphic imaging agents are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 300 mCi, preferably 10 mCi to about 200 mCi. The solution to be injected at unit dosage is from about 0.01 mL to about 10 mL. After intravenous administration, imaging of the organ or tumor in vivo can take place, if desired, in hours or even longer, after the radiolabeled reagent is introduced into a patient. In most instances, a sufficient amount of the administered dose will accumulate in the area to be imaged within about 0.1 of an hour to permit the taking of gamma scintigrams. Any conventional method of scintigraphic imaging for diagnostic or prognostic purposes can be utilized in accordance with this invention.

X. Uses for $^{99m}$Tc-EC Conjugates

The $^{99m}$Tc-EC conjugates of the invention may also be used for prognostic purposes. It is envisioned that EC-conjugates, listed in Table 1, may be administered to a patient having a tumor. It is envisioned that the use of $^{99m}$Tc-EC as a labeling strategy can be effective with ligands designed for targeting disease receptors, hypoxia markers, apoptosis defects, disease cell cycles, disease functional pathways, and assessment of pharmaceutical agents effectiveness of these biochemical processes. Imaging may be performed to determine the effectiveness of the $^{99m}$Tc-EC-conjugate against a patient's specific problem relating to disease receptors, hypoxia markers, apoptosis defects, disease cell cycles, disease functional pathways, and assessment of pharmaceutical agent's effectiveness on these biochemical processes. Using this methodology physicians can quickly determine which $^{99m}$Tc-EC-conjugate will be most effective for the patient and design the corresponding therapy or mode of treatment. This novel methodology represents a dramatic improvement over the current methods of choosing a drug and administering a round of chemotherapy, which may involve months of the patient's time at a substantial cost before the effectiveness of the cancer chemotherapeutic agent can be determined.

The present invention could also be used to monitor the progress of former patients who have sucessfully undergone chemotherapy or radiation treatment to determine if cancer has remained in remission or is metastasizing. People with a history of cancer in their family or who have been diagnosed with a gene(s) associated with cancer can undergo monitoring by health professionals using the methodology of the current invention. The methods and pharmaceutical agents of the current invention can also be used by a health professional to monitor if cancer has started to develop in a person with cancer risk factors due to environmental exposure to carcinogens.

XI. Tumor Angiogenesis Targeting

Throughout this application, "tumor angiogenesis targeting" refers to the use of an agent to bind to tumor neovascularization and tumor cells. Agents that are used for this purpose are known to those of ordinary skill in the art for use in performing various tumor measurements, including measurement of the size of a tumor vascular bed, and measurement of tumor volume. Some of these agents bind to the vascular wall. One of ordinary skill in the art would be familiar with the agents that are available for use for this purpose. A tumor angiogenesis targeting ligand is a ligand that is used for the purpose of tumor angiogenesis targeting as defined above. Examples of these agents include $^{99m}$Tc-EC-COX-2 (e.g., $^{99m}$Tc-EC-celecoxib), $^{99m}$Tc-EC-C225, $^{99m}$Tc-EC-herceptin, $^{99m}$Tc-EC-angiostatin, and $^{99m}$Tc-EC-thalidomide, which have been developed for the assessment of biochemical process on angiogenesis.

XII. Tumor Apoptosis Targeting

"Tumor apoptosis targeting" refers to use of an agent to bind to a cell that is undergoing apoptosis or at risk of undergoing apoptosis. These agents are generally used to provide an indicator of the extent or risk of apoptosis, or programmed cell death, in a population of cells, such as a tumor. One of ordinary skill in the art would be familiar with agents that are used for this purpose. Examples of apoptosis targeting agents are shown in Table 1. A "tumor apoptosis targeting ligand" is a ligand that is capable of performing "tumor apoptosis targeting" as defined in this paragraph. The targeting ligand of the present invention may include TRAIL (TNF-related apoptosis inducing ligand) monoclonal antibody. TRAIL is a member of the tumor necrosis factor ligand family that rapidly induces apoptosis in a variety of transformed cell lines. The targeting ligand of the present invention may also comprise a substrate of caspase-3, such as peptide or polypeptide that includes the 4 amino acid sequence aspartic acid-glutamic acid-valine-aspartic acid.

Apoptosis suppressors are targets for drug discovery, with the idea of abrogating their cytoprotective functions and restoring apoptosis sensitivity to tumor cells (Reed, 2003).

XIII. Disease Receptor Targeting

In "disease receptor targeting," certain agents are exploited for their ability to bind to certain cellular receptors that are overexpressed in disease states, such as cancer. Examples of such receptors which are targeted include estrogen receptors, androgen receptors, pituitary receptors, transferrin receptors, and progesterone receptors. Examples of agents that can be applied in disease-receptor targeting are shown in Table 1.

The radiolabeled ligands, such as pentetreotide, octreotide, transferrin, and pituitary peptide, bind to cell receptors, some of which are overexpressed on certain cells. Since these ligands are not immunogenic and are cleared quickly from the plasma, receptor imaging would seem to be more promising compared to antibody imaging. In this invention, the inventors developed a series of new receptor ligands. These ligands are $^{99m}$Tc-EC-leuteinizing hormone ($^{99m}$Tc-EC-LH) and $^{99m}$Tc-EC-transferrin.

XIV. Disease Cell Cycle Targeting

Gene based analogues for in vivo measurement of cell proliferation has been demonstrated by PET (Alauddin et al., 2001).

Disease cell cycle targeting refers to targeting of agents that are upregulated in proliferating cells. Compounds used for this purpose can be used to measure various parameters in cells, such as tumor cell DNA content.

Many of these agents are nucleoside analogues. For example, pyrimidine nucleoside (e.g., 2'-fluoro-2'-deoxy-5-iodo-1-β-D-arabinofuranosyluracil [FIAU], 2'-fluoro-2'-deoxy-5-iodo-1-β-D-ribofuranosyl-uracil [FIRU], 2'-fluoro-2'-5-methyl-1-β-D-arabinofuranosyluracil [FMAU], 2'-fluoro-2'-deoxy-5-iodovinyl-1-β-D-ribofuranosyluracil [IVFRU]) and acycloguanosine: 9-[(2-hydroxy-1-(hydroxymethyl)ethoxy)methyl]guanine (GCV) and 9-[4-hydroxy-3-(hydroxymethyl)butyl]guanine (PCV) (Tjuvajev et al., 2002; Gambhir et al., 1998; Gambhir et al., 1999) and other $^{18}$F-labeled acycloguanosine analogs, such as 8-fluoro-9-[(2-hydroxy-1-(hydroxymethyl)ethoxy)methyl]guanine (FGCV) (Gambhir et al., 1999; Namavari et al., 2000), 8-fluoro-9-[4-hydroxy-3-(hydroxymethyl)butyl]guanine (FPCV) (Gambhir et al., 2000; Iyer et al., 2001), 9-[3-fluoro-1-hydroxy-2-propoxy methyl]guanine (FHPG) (Alauddin et al., 1996; Alauddin et al., 1999), and 9-[4-fluoro-3-(hydroxymethyl)butyl]guanine (FHBG) (Alauddin and Conti, 1998; Yaghoubi et al., 2001) have been developed as reporter substrates for imaging wild-type and mutant (Gambhir et al., 2000) HSV1-tk expression. One or ordinary skill in the art would be familiar with these and other agents that are used for disease cell cycle targeting.

In this invention, the inventors developed a series of disease cell cycle targeting ligands. These ligands include, for example, $^{99m}$Tc-EC-adenosine and $^{99m}$Tc-EC-penciclovir (EC-guanine).

XV. Drug Assessment

Certain drug-based ligands of the present invention can be applied in measuring the pharmacological response of a subject to a drug. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject. Radiolabeled agents can be applied in measuring drug assessment.

In this invention, the inventors developed a new drug based ligand, $^{99m}$Tc-EC-carnitine (Taggart et al., 1999). Other examples of these agents are shown in Table 1.

XVI. Pharmaceutical Preparations

Pharmaceutical compositions of the present invention comprise an effective amount of an $N_2S_2$ chelate-targeting ligand conjugate of the present invention dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one radiolabeled ethylenedicysteine derivative or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The $N_2S_2$ chelates of the present invention may comprise different types of carriers depending on whether it is to be administered in solid, liquid or aerosol form, and whether it needs to be sterile for such routes of administration such as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a radiolabeled ethylenedicysteine derivative. In other embodiments, the active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The radiolabeled ethylenedicysteine derivative may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the radiolabeled ethylenedicysteine derivative in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

XVII. Combinational Therapy

It is an aspect of this invention that $N_2S_2$ chelate-targeting ligand conjugates of the present invention can be used in combination with another agent or therapy method, preferably another cancer treatment. The radiolabeled ethylenedicysteine derivative may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the radiolabeled ethylenedicysteine derivative. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the radiolabeled ethylenedicysteine derivative. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the radiolabeled ethylenedicysteine derivative. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, the radiolabeled ethylenedicysteine derivative is "A" and the secondary agent, which can be any other therapeutic agent, is "B":

A/B/A B/A/B B/B/A A/A/B A/B/B B/A/A A/B/B/B B/A/
B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described arsenical agent. These therapies include but are not limited to chemotherapy, radiotherapy, immunotherapy, gene therapy and surgery.

a. Chemotherapy

Cancer therapies also include a variety of combination therapies with both chemical and radiation based treatments. Combination chemotherapy include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, cisplatinum, 5-fluorouracil, vincristin, vinblastin and methotrexate, or any analog or derivative variant of the foregoing.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Genes

In yet another embodiment, the secondary treatment is a secondary gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues.

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically or partially removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

XVIII. Synthesis of EC

EC was prepared in a two-step synthesis according to the previously described methods (Ratner and Clarke, 1937; Blondeau et al., 1967; each incorporated herein by reference). The precursor, L-thiazolidine-4-carboxylic acid, was synthesized (m.p. 195°, reported 196-197°). EC was then prepared (m.p. 237°, reported 251-253°). The structure was confirmed by $^1$H-NMR and fast-atom bombardment mass spectroscopy (FAB-MS).

XIX. Scintigraphic Imaging and Autoradiography Studies

Scintigraphic images, using a gamma camera (Siemens Medical Systems, Inc., Hoffman Estates, Ill., or Philips Medical Systems, Skylight, Milpitas, Calif.) equipped with low-energy, parallel-hole collimator, were obtained 0.5, 2 and 4 hrs after i.v. injection of 18.5 MBq of $^{99m}$Tc-labeled radiotracer.

Whole-body autoradiogram were obtained by a quantitative image analyzer (Cyclone Storage Phosphor System, Packard, Meridian, CI.). Following i.v. injection of 37 MBq of $^{99m}$Tc-EC-folate, animal killed at 1 h and body was fixed in carboxymethyl cellulose (4%). The frozen body was mounted onto a cryostat (LKB 2250 cryomicrotome) and cut into 100 μm coronal sections. Each section was thawed and mounted on a slide. The slide was then placed in contact with multipurpose phosphor storage screen (MP, 7001480) and exposed for 15 h $^{99m}$Tc-labeled). The phosphor screen was excited by a red laser and resulting blue light that is proportional with previously absorbed energy was recorded.

XX. Definitions

As used herein the term "radionuclide" is defined as a radioactive nuclide (a species of atom able to exist for a measurable lifetime and distinguished by its charge, mass, number, and quantum state of the nucleus) which, in specific embodiments, disintegrates with emission of corpuscular or electromagnetic radiation. The term may be used interchangeably with the term "radioisotope".

The term "therapeutic agent" as used herein is defined as an agent which provides treatment for a disease or medical condition. The agent in a specific embodiment improves at least one symptom or parameter of the disease or medical condition. For instance, in tumor therapy, the therapeutic agent reduces the size of the tumor, inhibits or prevents growth or metastases of the tumor, or eliminates the tumor. Examples include a drug, such as an anticancer drug, a gene therapy composition, a radionuclide, a hormone, a nutriceutical, or a combination thereof.

The term "tumor" as used herein is defined as an uncontrolled and progressive growth of cells in a tissue. A skilled artisan is aware other synonymous terms exist, such as neoplasm or malignancy. In a specific embodiment, the tumor is a solid tumor. In other specific embodiments, the tumor derives, either primarily or as a metastatic form, from cancers such as of the liver, prostate, pancreas, head and neck, breast, brain, colon, adenoid, oral, skin, lung, testes, ovaries, cervix, endometrium, bladder, stomach, and epithelium (such as a wart).

The term "drug" as used herein is defined as a compound which aids in the treatment of disease or medical condition or which controls or improves any physiological or pathological condition associated with the disease or medical condition. In a specific embodiment, the drug is a $^{99m}$Tc-EC-drug conjugate.

The term "anticancer drug" as used herein is defined as a drug for the treatment of cancer, such as for a solid tumor. The anticancer drug preferably reduces the size of the tumor, inhibits or prevents growth or metastases of the tumor, and/or eliminates the tumor.

As used herein the specification, "a" or "an" may mean one or more. As used herein in the claim(s), when used in conjunction with the word "comprising", the words "a" or "an" may mean one or more than one. As used herein "another" may mean at least a second or more.

XXI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Targeting Integrin ($\alpha_v\beta_3$) with EC-Angiostatin a. Synthesis of Ethylenedicysteine (EC)

Integrin ($\alpha_v\beta_3$) is a disease angiogenic target that can be targeted with EC-angiostatin, a compound of the present invention. EC was prepared in a two-step synthesis according to the previously described methods (Ratner and Clarke, 1937; Blondeau et al., 1967; each incorporated herein by reference). The precursor, L-thiazolidine-4-carboxylic acid, was synthesized (m.p. 195°, reported 196-197°). EC was then prepared (m.p. 237°, reported 251-253°). The structure was confirmed by 1H-NMR and fast-atom bombardment mass spectroscopy (FAB-MS).

b. Radiosynthesis of $^{99m}$Tc-EC-Angiostatin

Sodium bicarbonate (1N, 1 ml) was added to a stirred solution of EC (3.27 mg, 12.2 µmol). To this colorless solution, sulfo-N-hydroxysulfosuccinimide (Sulfo-NHS, Pierce Chemical Co., Radford, Ill.) (3.0 mg, 13.8 mmol) and 1-ethyl-3-(3-dimethylaminopropyl) carbodiimide (EDC, 2.0 mg, 10.5 µmol) (Aldrich Chemical Co., Milwaukee, Wis.) were added. Angiostatin (32.7 mg, 0.93 µmol) was then added. The mixture was stirred at room temperature for 18 hrs. The mixture was dialyzed for 48 hrs (M.W. cut-off of 10,000). EC-angiostatin weighed 17 mg (yield: 100%) after freeze drying. $^{99m}$Tc-pertechnetate (5.5 mCi) (Syncor Pharmaceutical Inc., Houston, Tex.) was added to a vial containing the lyophilized residue of EC-angiostatin (10 µg, 0.5 nmol) and tin chloride (II) ($SnCl_2$, 100 g, 0.53 µmol) in 0.2 ml water. The product was purified by using a sephadex G-25 column (bed volume 10 ml) (Sigma Chemical Company, St. Louis, Mo.) and eluted with PBS (5 ml). One milliliter of eluant was collected in each test tube. The product was isolated in Tubes 3 and 4, and yielded 3.9 mCi (70%). Radiochemical purity was assessed by Radio-TLC scanner (Bioscan, Washington, D.C.) using 1M ammonium acetate:methanol (4:1) as an eluant. High performance liquid chromatograph (HPLC), equipped with a GPC column (Biosep SEC-S3000, 7.8×300 mm, Phenomenex, Torrance, Calif.) and two detectors (NaI and UV), was used to analyze the purity of the product. The eluant was 0.1% LiBr in PBS (10 mM) and the flow rate was 1.0 ml/min.

c. In Vitro Cellular Uptake Assays and Tissue Distribution Studies

Figure 2:
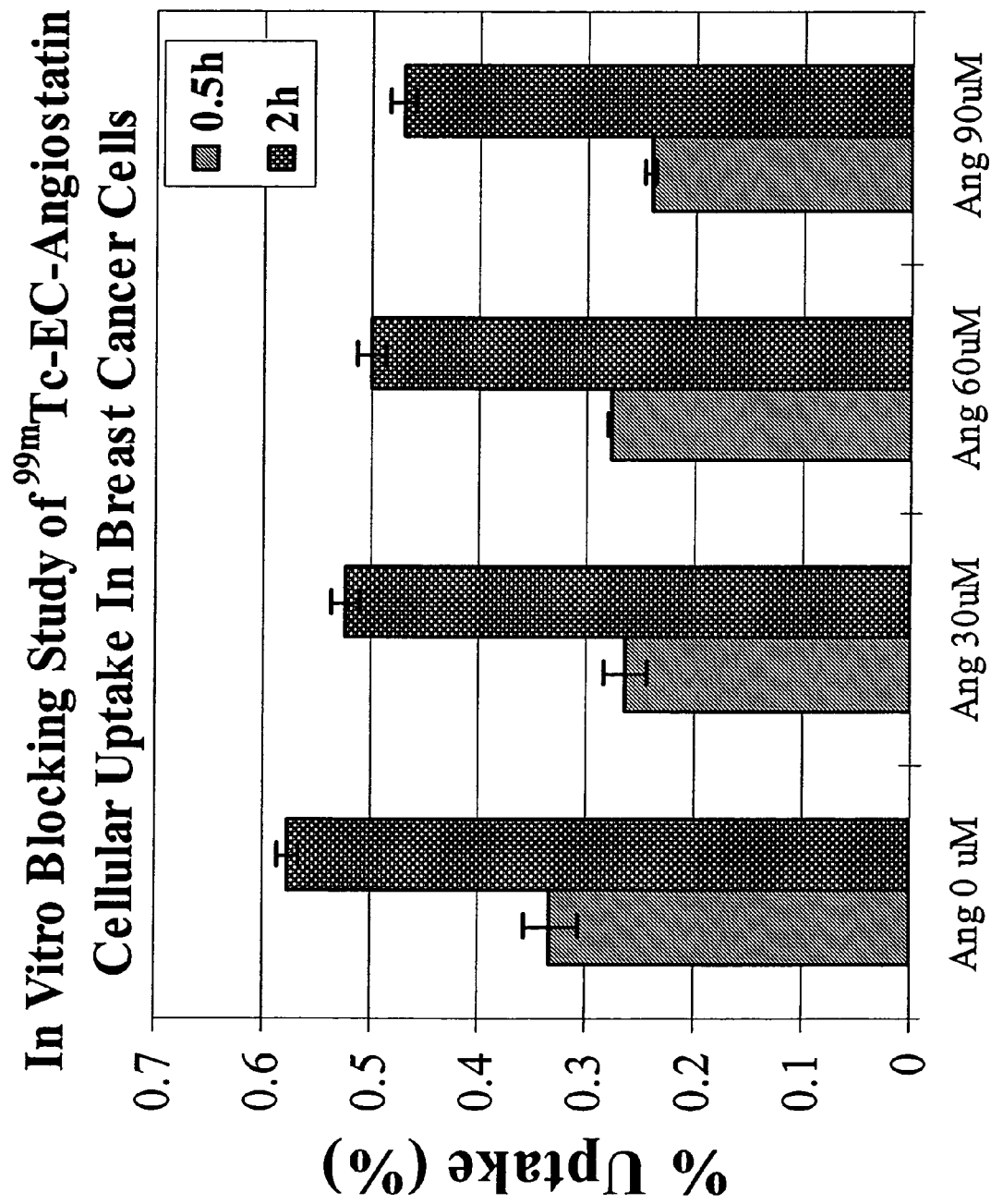
FIG. 2: In vitro blocking study of $^{99m}$Tc-EC-Angiostatin in breast cancer cells with unlabeled angiostatin. In vitro cellular uptake assays showed decreased uptake by adding unlabeled angiostatin.
Figure 3:
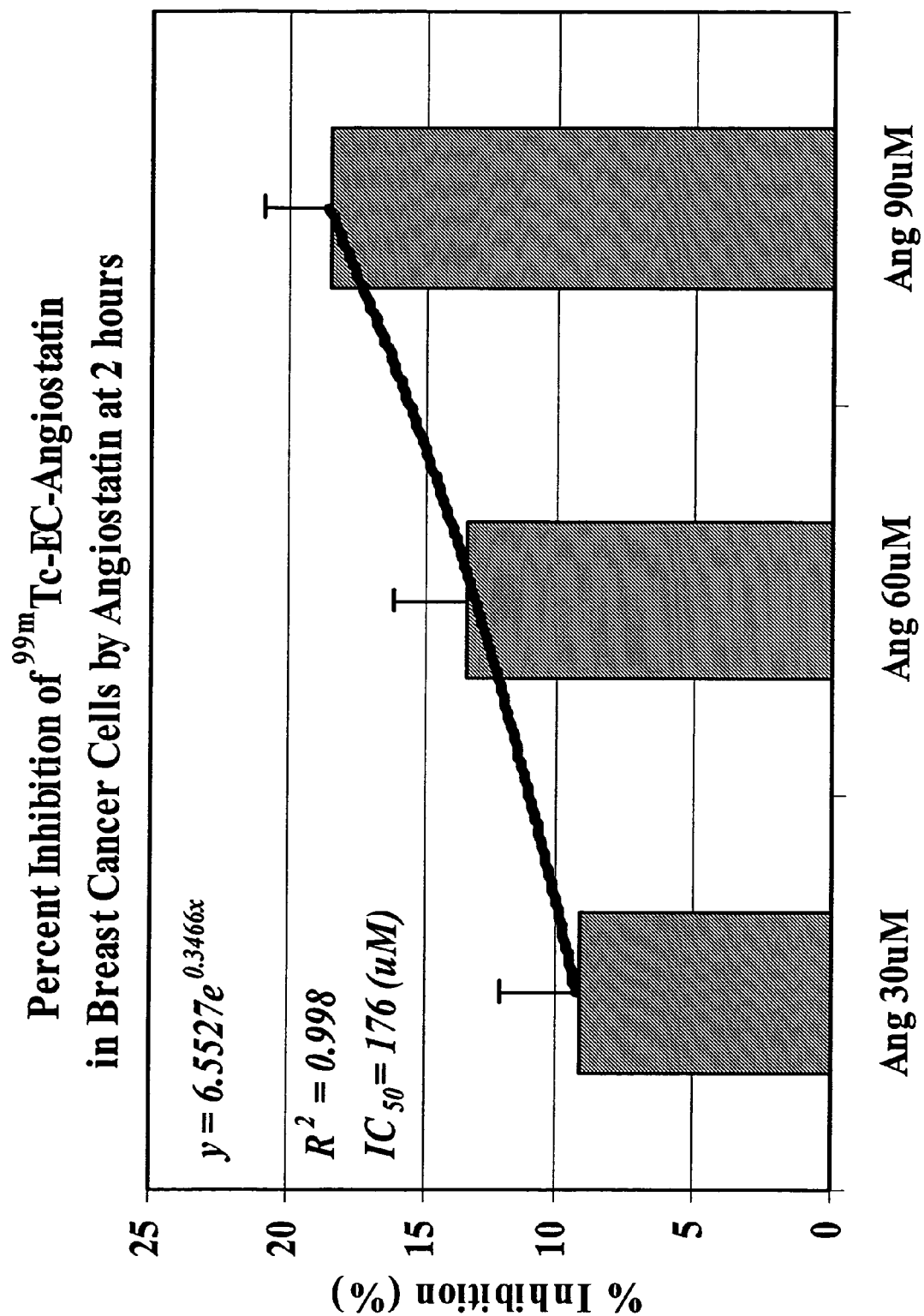
FIG. 3: Percent inhibition of $^{99m}$Tc-EC-Angiostatin after adding unlabeled angiostatin in breast cancer cells at 2 hours.

In vitro cell culture at various concentration of angiostatin (0-200 µM) was incubated with $^{99m}$Tc-EC-angiostatin (4 µCi/50,000 cells/well) at 0.5-2 hrs in RBA CRL-1747. There was a significant decreased uptake of $^{99m}$Tc-EC-angiostatin after adding unlabeled angiostatin in cancer cells, suggesting receptor mechanism of the uptake (FIGS. 1-2). The IC-50 of angiostatin was 176 µM ($R^2$=0.998) (FIG. 3).

Figure 4:
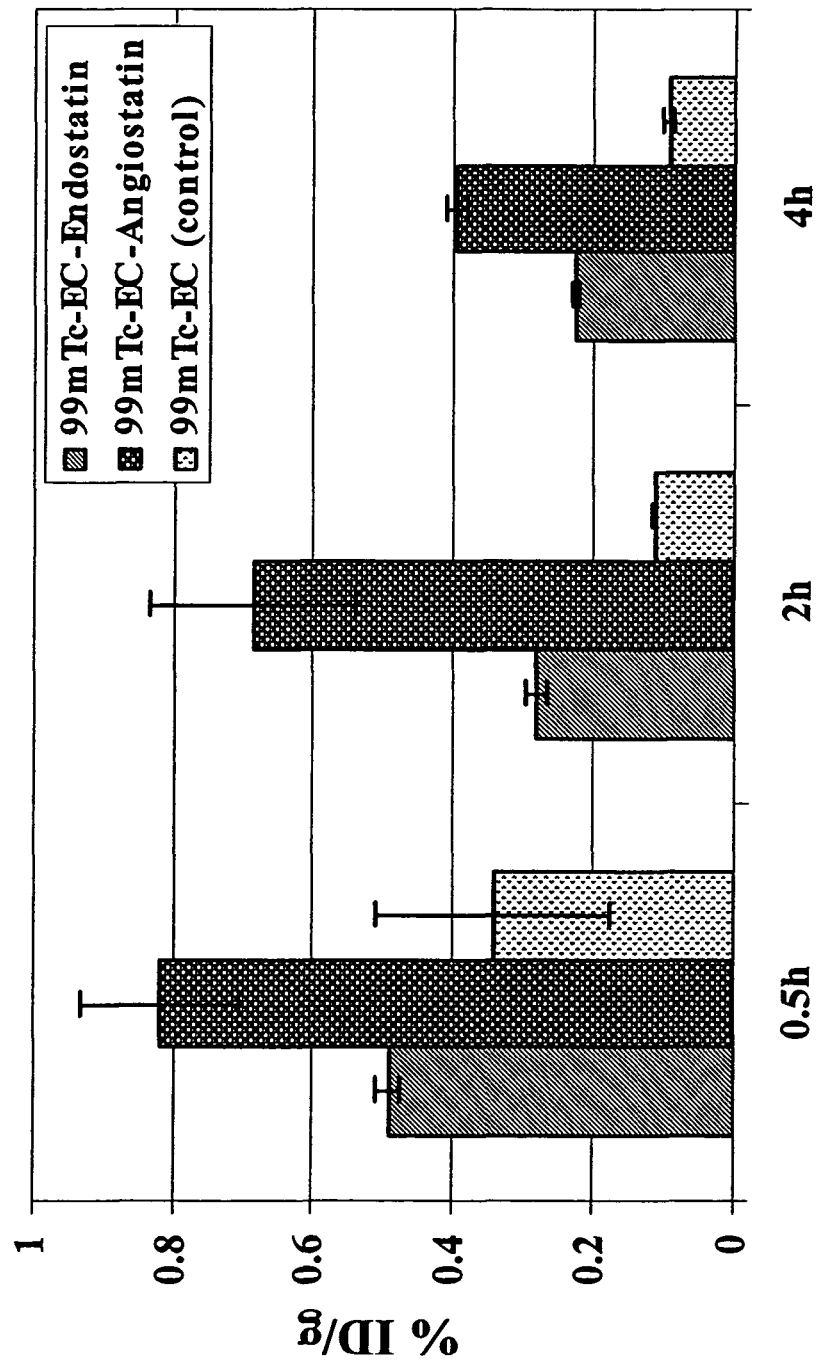
FIG. 4: Tumor uptake of $^{99m}$Tc-EC-anti-angiogenic agents in breast tumor-bearing rats. Nine rats/group were administered $^{99m}$Tc-EC-endostatin, $^{99m}$Tc-EC-angiostatin, and $^{99m}$Tc-EC (iv., tail vein) and sacrificed at 0.5-4 hours post-injection where selected organs were excised. Data are reported as mean±SEM (n=3). The data points were calculated as percentage of injected dose per gram of tissue.
Figure 5:
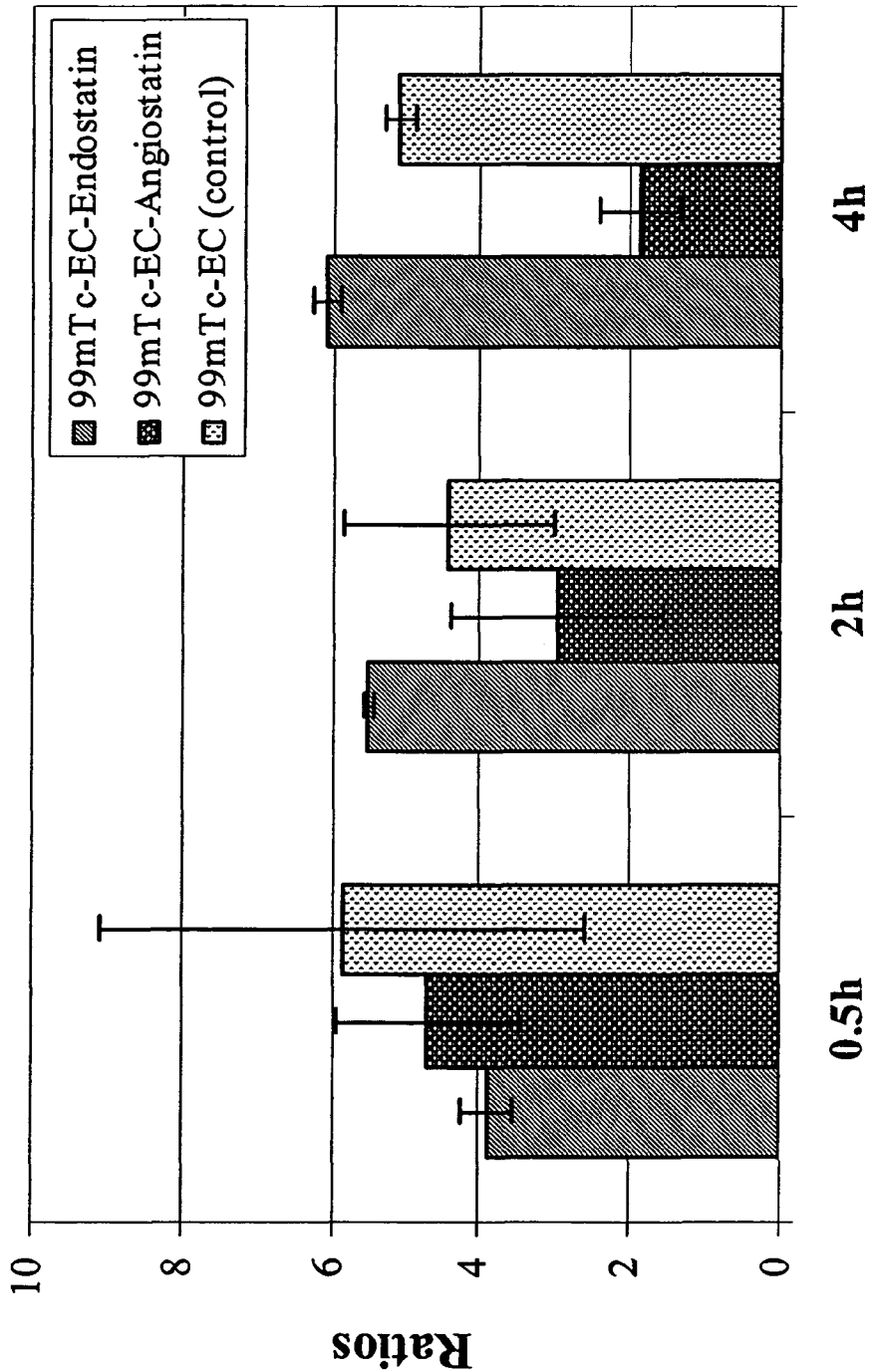
FIG. 5: Tumor-to-muscle count density ratios of $^{99m}$Tc-EC-anti-angiogenic agents. Tumor-to-muscle count density ratios of $^{99m}$Tc-EC-labeled agents in breast tumor bearing rats are shown. Nine rats/group were administered $^{99m}$Tc-EC-endostatin, $^{99m}$Tc-EC-angiostatin, and $^{99m}$Tc-EC (iv., tail vein) and sacrificed at 0.5-4 hours post-injection where selected organs were excised. Data are reported as mean±SEM (n=3). The data points were calculated as percentage of injected dose per gram of tissue.

Biodistribution was assessed in mammary tumor-bearing rats (RBA CRL-1747, n=3/time interval, iv). Studies were performed 14 to 17 days after implantation when tumors reached approximately 1 cm in diameter. Following administration of the radiotracer, rats were sacrificed at 0.5-4 hrs. The selected tissues were excised, weighed and counted for radioactivity by using a gamma counter (Packard Instruments, Downers Grove, Ill.). The biodistribution of tracer in each sample was calculated as percentage of the injected dose per gram of tissue wet weight (% ID/g). Biodistribution of $^{99m}$Tc-EC-angiostatin in tumor-bearing rats showed increased tumor-to-tissue count density ratios as a function of time (FIGS. 4-5).

d. Scintigraphic Imaging Studies

Figure 6:
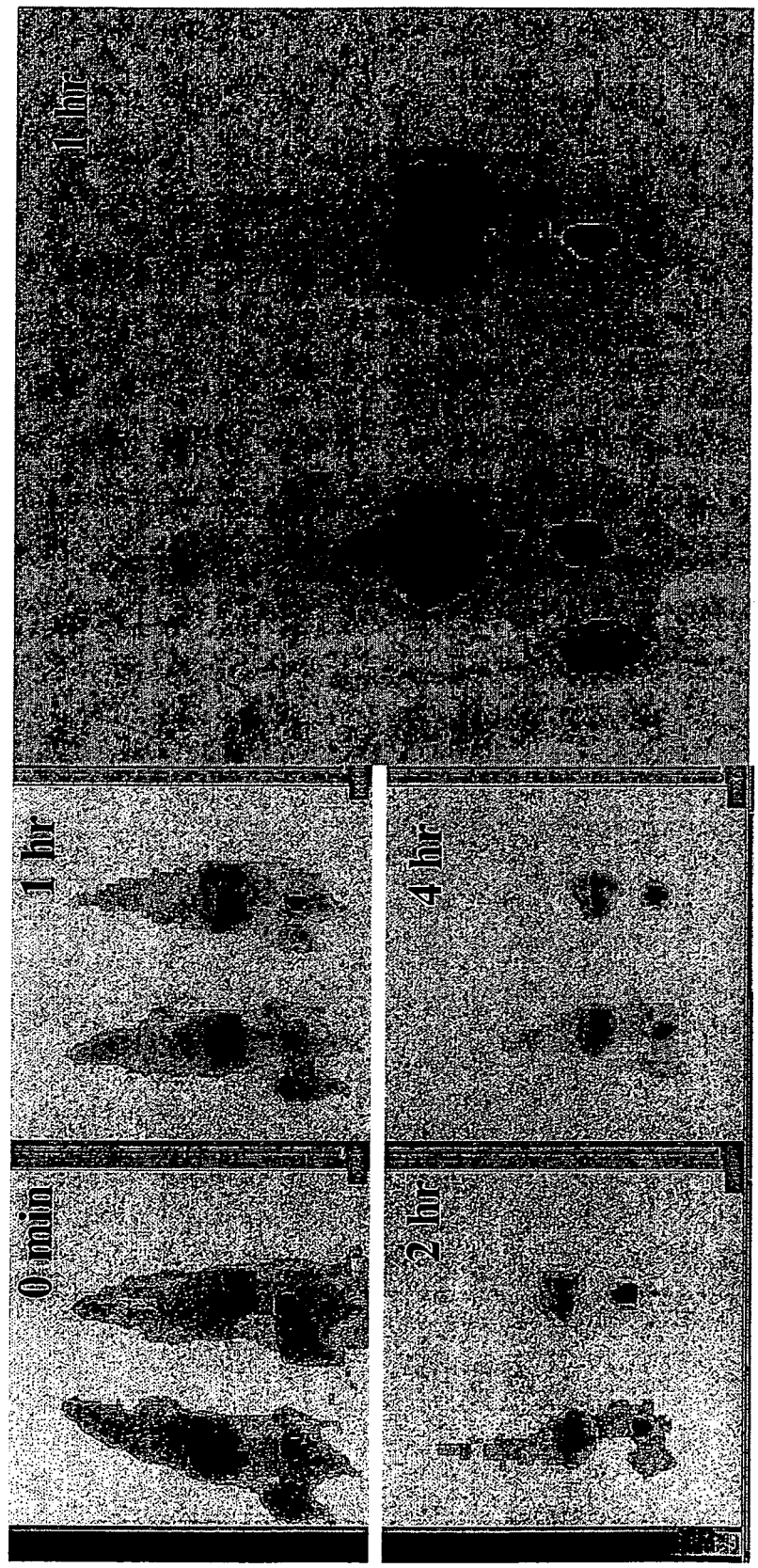
FIG. 6: Scintigraphic images of $^{99m}$Tc-EC-angiostatin. Planar images of breast tumor-bearing rats after administration of $^{99m}$Tc-EC-angiostatin (left rat) and $^{99m}$Tc-EC (right rat) showed that tumor could be visualized from 0.5-4 hours post-injection.

Scintigraphic imaging studies was performed in mammary tumor-bearing rats at 0.5-4 hrs (0.3 mCi/rat, n=3, iv). Control group was administered $^{99m}$Tc-EC. Computer-outlined region of interest was used to determine tumor uptake (counts/pixel) and tumor/nontumor count density ratios. Planar images confirmed that the tumors could be visualized clearly with radiolabeled angiostatin (FIG. 6).

Numerous other proteins and peptides can be applied using this technology described in Example 1. These include EC- VEGF (Vascular endothelial growth factor), EC-endostatin (anti-endothelial cells), EC-interferon α (anti-FGF).

Example 2

Targeting EGFR with EC-C225 Monoclonal Antibody a. Radiosynthesis of $^{99m}$Tc-EC-C225

Figure 7:
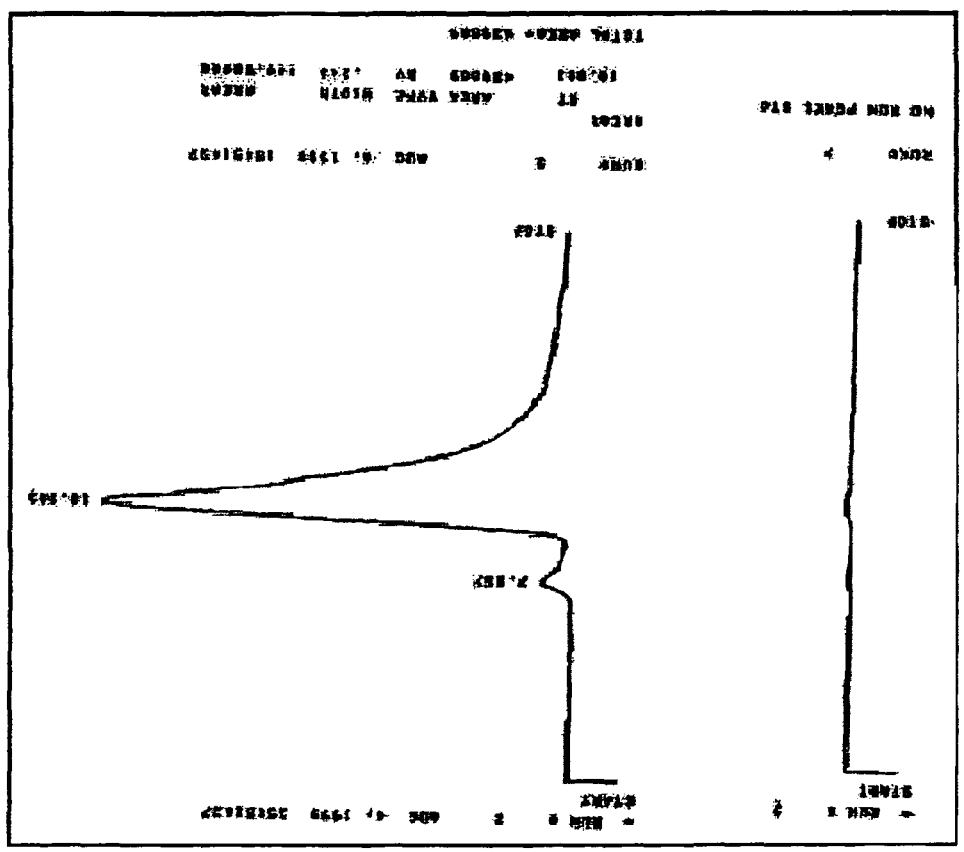
FIG. 7: HPLC chromatogram of $^{99m}$Tc-EC-C225. Peak designates 20 μl injection of fraction #2 (3 ml, 5.8 μCi). Conditions: Phenomenex C-18 reverse phase column; flow rate: 1 ml/min, 0.1% LiBr in 10 mM PBS; pH=7.4.

EGFR is a disease angiogenic target that can be targeted with $^{99m}$Tc-EC-C225 monoclonal antibody, a compound of the present invention. Clinical grade anti-EGF receptor R MAb C225 (IMC-C225) was obtained from ImClone Systems, Inc. (Somerville, N.J.). C225 (20 mg) was stirred with EC (28.8 mg, 0.11 mmol in 1.4 ml of 1N NaHCO$_3$), sulfo-NHS (23.3 mg, 0.11 mmol) and EDC (16.6 mg, 0.09 mmol). After dialysis, 17 mg of EC-C225 was obtained. 100 mCi of Na$^{99m}$TcO4 was added into a vial containing 1 mg EC-C225 and 100 μg SnCl$_2$ and the product was purified with a G-25 column and eluted with PBS, yielded 80 mCi $^{99m}$Tc-EC-C225. Radiochemical purity for $^{99m}$Tc-EC-C225 was 100% (HPLC, gel permeation column, 0.1% LiBr in 100 mM PBS, pH 7.4). Specific activity was 2 Ci/μmol (FIG. 7).

Figure 8:
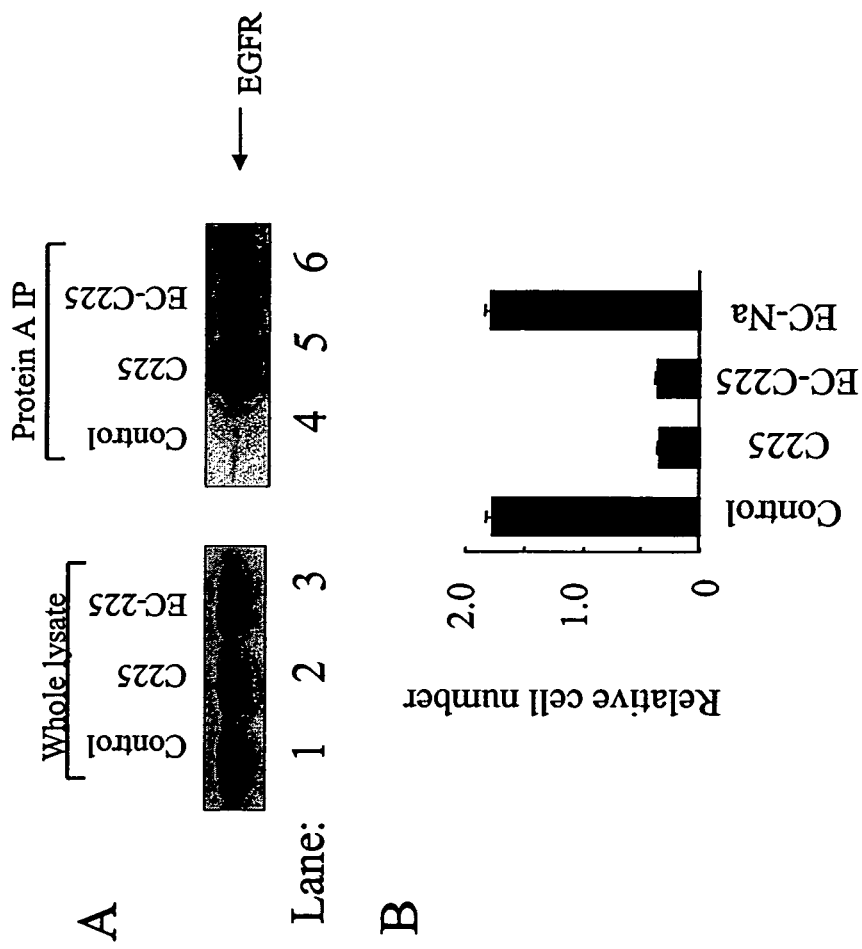
FIG. 8: In vitro comparison of EC-C225 and C225. Western blot and immunoprecipitation assays (Panel A) showed that EC-C225 was immunocompetent in binding to the EGFR in A431 cells. Cell proliferation assays (MTT, Panel B) showed that both C225 and EC-C225 induced cell death (apoptosis) in DiFi human colon cancer cells. EC-Na did not show any effect on cell proliferation compared with untreated control cells.

For example, an immunoassay (Western Blot and Immunoprecipitation) and cell proliferation assays were used to examine the integrity of EC-C225. Briefly, DiFi cells are known to undergo apoptosis when they are exposed to C225 in cell culture. Cells were seeded onto 24-well culture plates. Cell viability was assayed by adding 50 ul of 10 mg/ml MTT (3-[4,5-dimethylthiazol-2-yl]-2,5-diphenyltetrazolium bromide) (Sigma) into 0.5 ml of culture medium and the cells were incubated for 3 h at a 37° C. in a CO$_2$ incubator, followed by cell lysis with buffer containing 20% SDS in dimethyl formamide/H$_2$O, pH 4.7, at 37° C. for more than 6 h. Cell viability was then determined by measuring the optical absorbance of cell lysate at a wavelength of 595 nm and normalizing the value with the corresponding untreated cells. The result shows that EC-C225 is biologically active in inducing cell death in DiFi cells. In contrast, the EC-Na did not show any effect on cell proliferation when compared with untreated control cells (FIG. 8).

b. Tissue Distribution Studies

Figure 9:
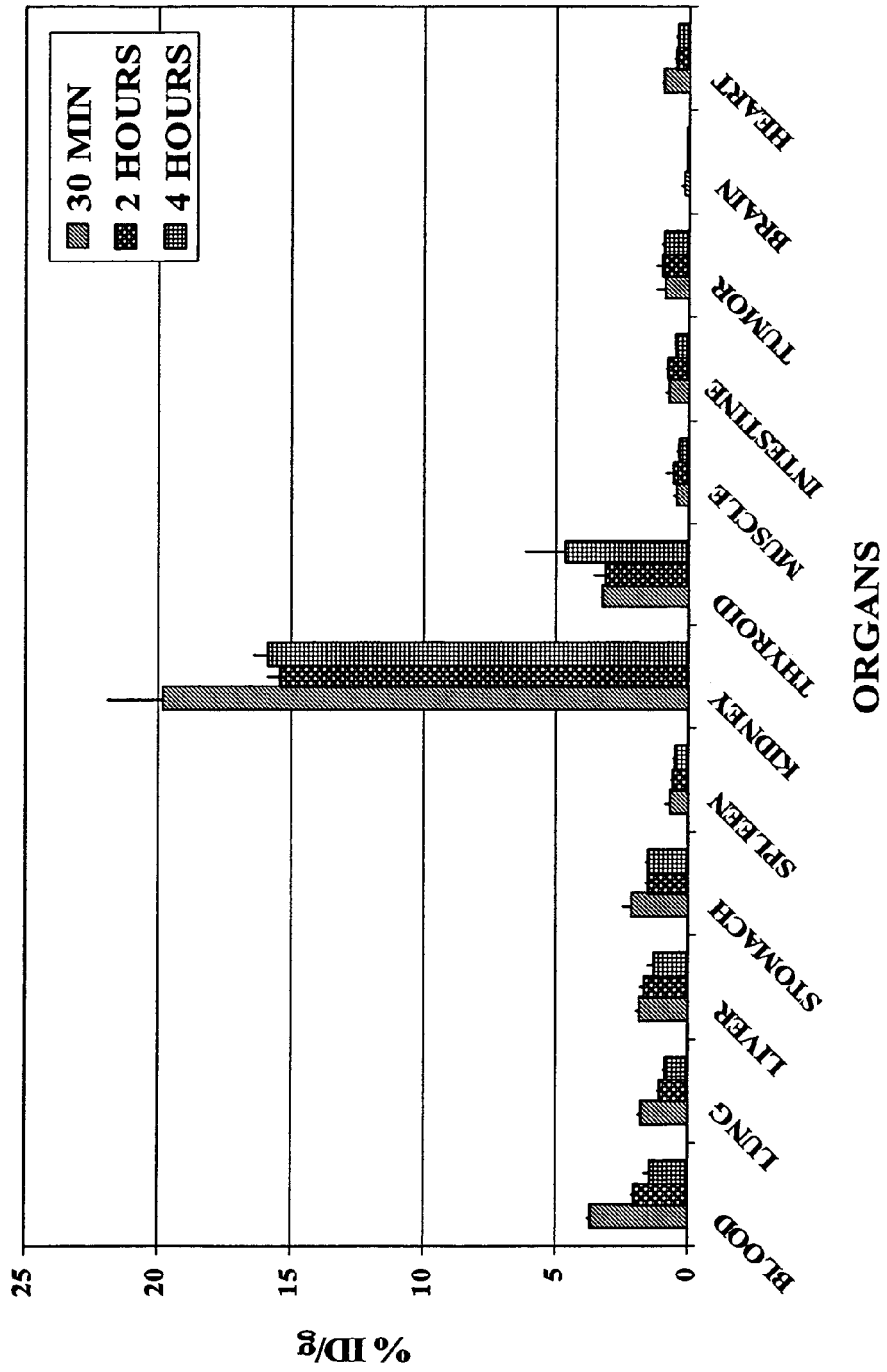
FIG. 9: Biodistribution of $^{99m}$Tc-EC-C225 in A431 vulvic tumor-bearing nude mice. Tissue uptake of $^{99m}$Tc-EC-C225 in vulvic tumor bearing nude mice are shown. Nine mice were administered $^{99m}$Tc-EC-C225 (iv., tail vein) and sacrificed at 0.5-4 hours post-injection where selected organs were excised. Data are reported as mean±SEM (n=3). The data points were calculated as percentage of injected dose per gram of tissue.
Figure 10:
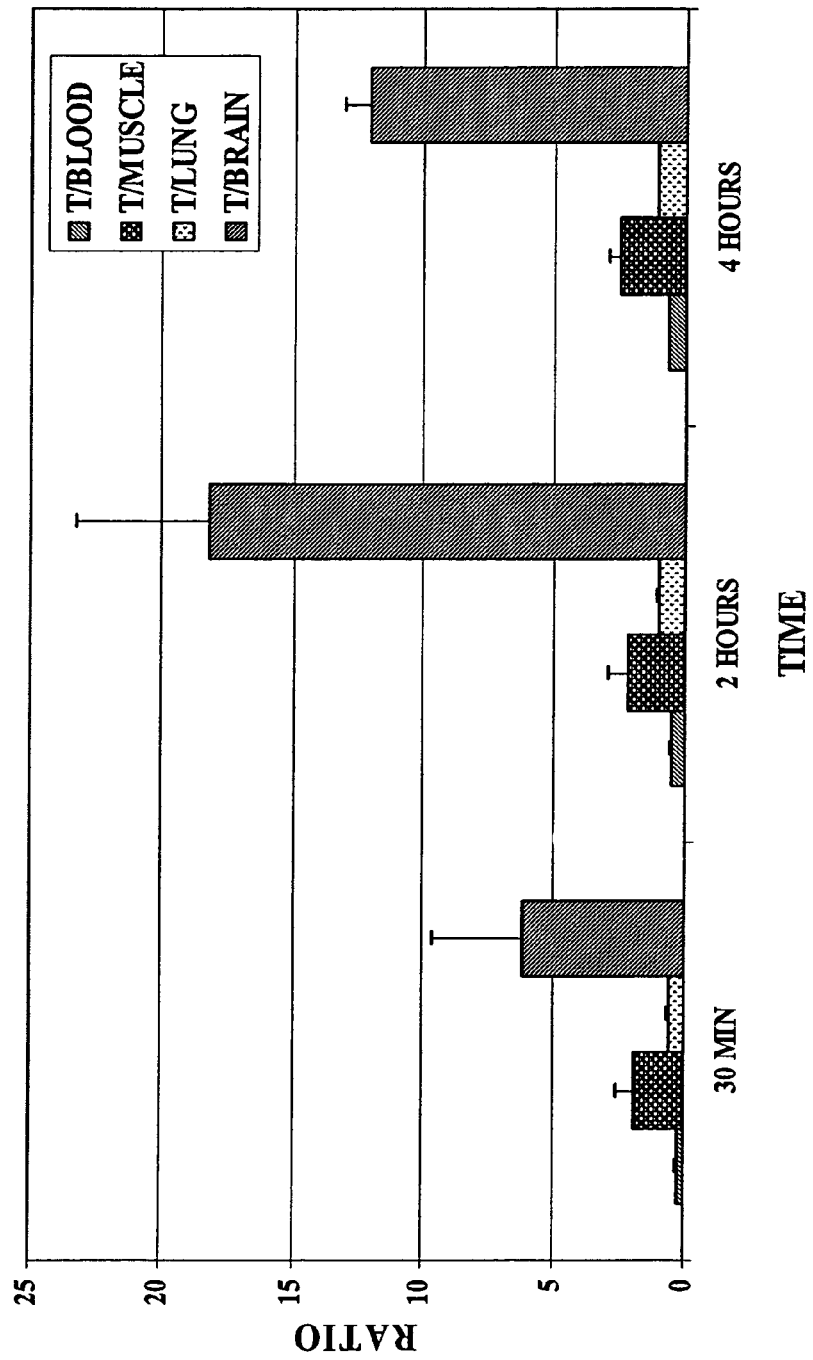
FIG. 10: Tumor-to-tissue count density ratios of $^{99m}$Tc-EC-C225 in A431 vulvic tumor-bearing nude mice. Nine mice were administered $^{99m}$Tc-EC-C225 (iv., tail vein) and sacrificed at 0.5-4 hours post-injection where selected organs were excised. Data are reported as mean±SEM (n=3). The data points were calculated as percentage of injected dose per gram of tissue.

Biodistribution was assessed in A431 (an EGFR overexpressing xenograft) grown in nude mice (1 μCi/mouse, 10 μg/mouse, n=3/time interval, iv). Studies were performed 14 to 17 days after implantation when tumors reached approximately 1 cm in diameter. Following administration of the radiotracer, mice were sacrificed at 0.5-4 hrs. The selected tissues were excised, weighed and counted for radioactivity by using a gamma counter. The biodistribution of tracer in each sample was calculated as percentage of the injected dose per gram of tissue wet weight (% ID/g). Biodistribution studies showed that tumor-to muscle count density ratios increased as a function of time (FIG. 9). Tumor uptake (% ID/g) was 1±0.2%. Total tumor uptake was 6% of injected dose (FIG. 10).

c. Scintigraphic Imaging Studies

Figure 11:
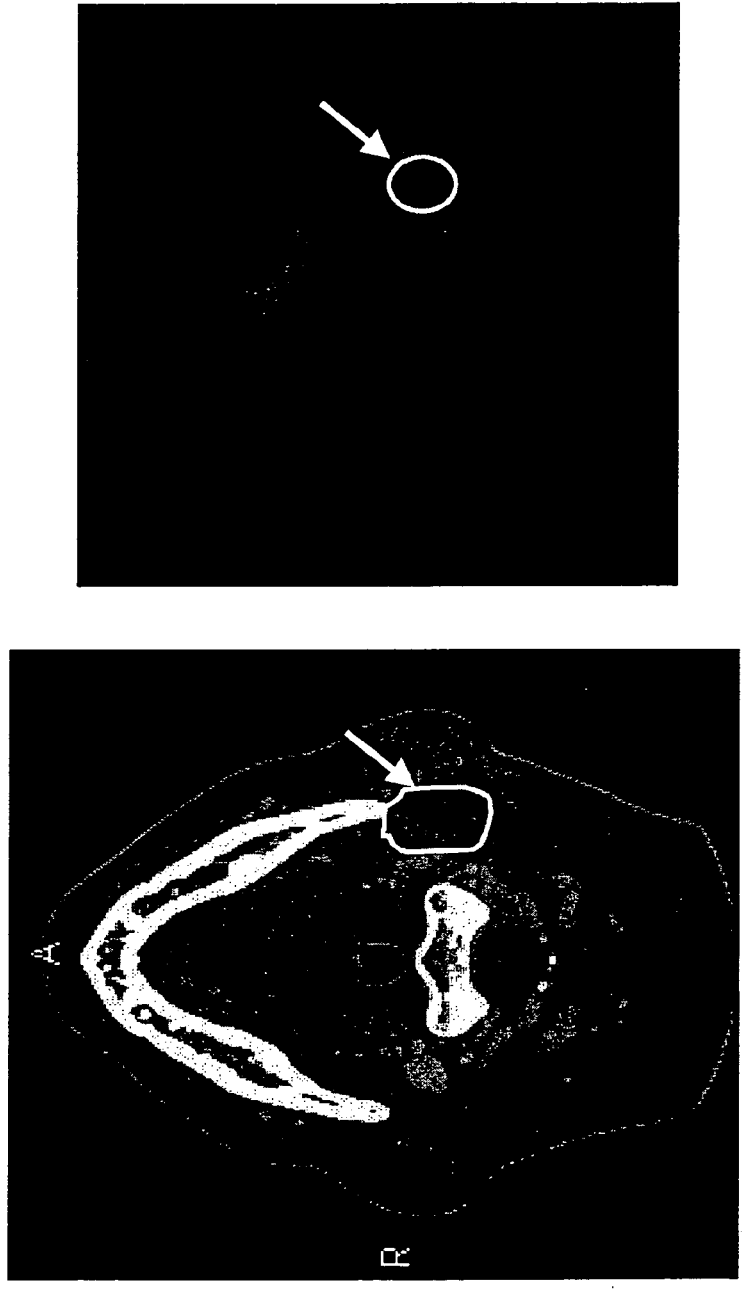
FIG. 11: Case study 1: $^{99m}$Tc-EC-C225 scan for head and neck cancer: left jugulodigastric lymph node. CT (left) and $^{99m}$Tc-EC-C225 (right) scans are shown. Dynamic flow study of the head and neck after the injection of 22.7 mCi of $^{99m}$Tc-EC-C225 shows no focal area of significantly increased blood flow. Uptake of $^{99m}$Tc-EC-C225 in the left jugulodigastric and submandibular lymphadenopathy chains is outlined and designated by arrow.
Figure 12:
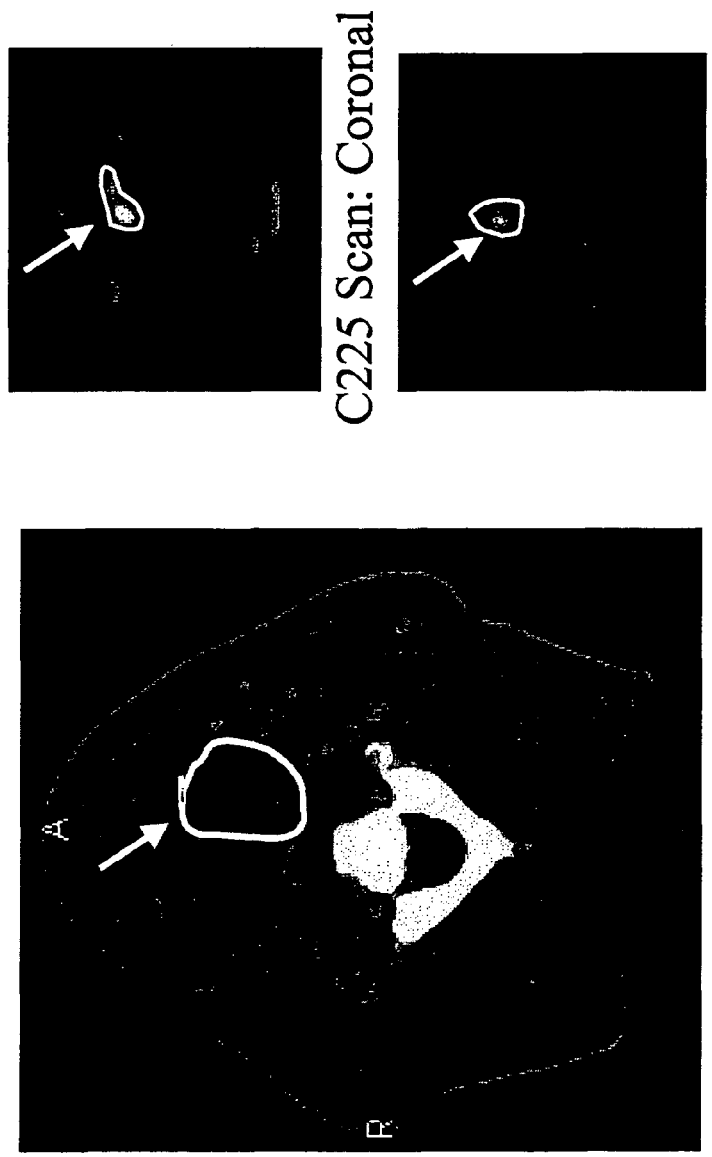
FIG. 12: Case study 2: $^{99m}$Tc-EC-C225 scan for head and neck cancer: left base of tongue and floor of mouth. CT (left) and $^{99m}$Tc-EC-C225 (right:top and bottom) scans are shown. Dynamic flow study and blood pool images of head and neck after injection of 25.7 mCi $^{99m}$Tc-EC-C225 demonstrate no focal area of abnormally increased blood flow or vascularity. Focal areas of markedly increased activity in the left tongue base and focal areas of slightly increased activity in the left upper and lower jugular lymphatic chains are outlined and designated by arrow.

SPECT imaging (25-30 mCi/patient) was performed in 5 patients with HNSCC at 0.5-24 hrs. Each patient underwent a scan prior to C225 antibody therapy in combination with radiotherapy. Computer-outlined region of interest was used to determine tumor uptake (counts/pixel) and tumor/nontumor count density ratios. Clinical SPECT images showed that tumor could be visualized at 0.5-4 hrs. Images and findings were illustrated in FIGS. 11-12.

Other antibodies can be applied using the EC technology, including EC-Herceptin (anti-HER2), EC-CD31, EC-CD40 (immunomodulator), EC-HSA (human serum albumin).

Example 3

Targeting COX-2 Enzyme with EC-Celecoxib a. Synthesis of Ethylamino Celecoxib (EA-Celecoxib)

Figure 13:
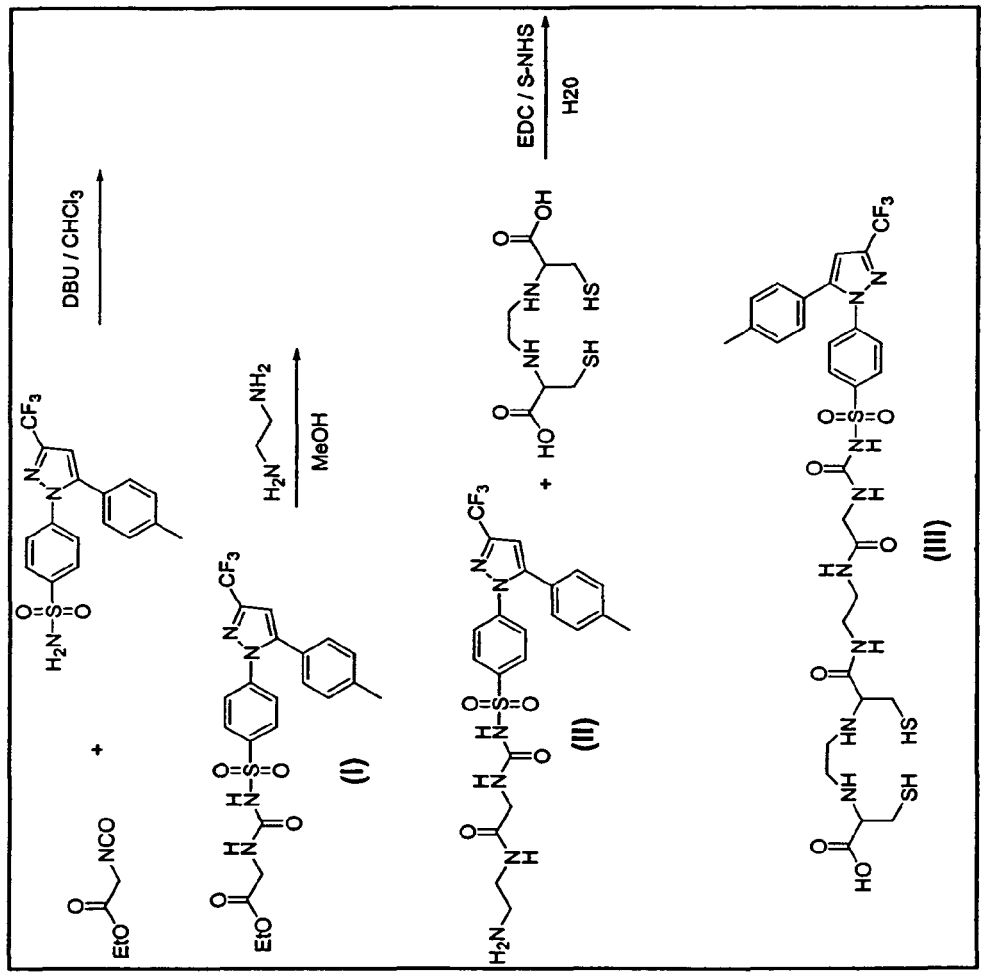
FIG. 13: Synthesis of $^{99m}$Tc-EC-celecoxib.
Figure 14:
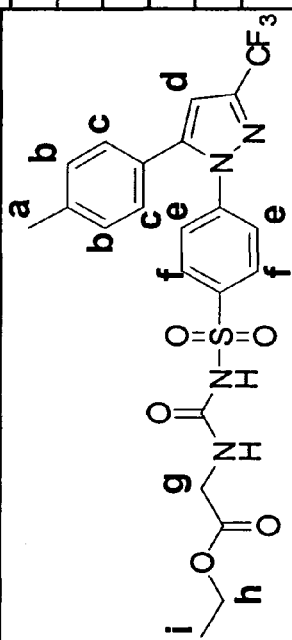
FIG. 14: NMR spectra data of EC-celecoxib-ester. NMR spectra data of celecoxib ester (compound (I)) are shown.

The COX-2 enzyme is a disease angiogenic target that can be targeted with EC-celecoxib, a compound of the present invention. N-4-(5-p-tolyl-3-trifluoromethyl-pyrazol-1-yl) benzenesulfonylamide (celecoxib) (114.4 mg, 0.3 mmol) was dissolved in chloroform (2 ml). To this solution, DBU 44.9 μl (0.3 mmol in chloroform 0.5 ml) and ethyl isocyanatoacetate 33.741 (0.3 mmol in chloroform 0.5 ml) were added. The reaction was stirred at room temperature for 6 hours. The solvent was evaporated under vacuo. The product was isolated from silica gel-packed column using chloroform/methanol as an eluant. The yield of the ester form of celecoxib (compound I) was 135 mg (88.1%). The synthetic scheme is shown in FIG. 13. NMR spectra data was recorded in FIG. 14.

Compound I (102 mg, 0.2 mmol) was dissolved in 2 ml of methanol and ethylene diamine (72.9 μl) was added. The reaction was stirred at room temperature for 24 hours. The product was isolated from silica gel-packed column using chloroform/methanol as an eluant. The desired ethylamino celecoxib (EA-celecoxib) (compound II) was isolated (91 mg, 86.7% yield). NMR spectra data of compound II was recorded in FIG. 15.

b. Synthesis of EC-Ethylamino Celecoxib (EC-Celecoxib)

To dissolve EC, NaOH (1N, 0.6 ml) was added to a stirred solution of EC (42.3 mg, 0.15 mmol) in water (3 ml). To this colorless solution, sulfo-NHS (65.1 mg, 0.3 mmol) and EDC (57.5 mg, 0.3 mmol) were added. EA-celecoxib (78.6 mg, 0.15 mmol) was then added. The mixture was stirred at room temperature for 24 hours and then dialyzed for 48 hours using Spectra/POR molecular porous membrane with molecule cut-off at 500 (Spectrum Medical Industries Inc., Houston, Tex.). After dialysis, the product was freeze dried. The product weighed 87.5 mg (yield 75%).

c. Radiolabeling of EC-Celecoxib with $^{99m}$Tc

Radiosynthesis of $^{99m}$Tc-EC-celecoxib was achieved by adding required amount of $^{99m}$Tc-pertechnetate into homemade kit containing the lyophilized residue of EC-celecoxib (5 mg), SnCl$_2$ (100 μg), Na$_2$HPO$_4$ (13.5 mg), ascorbic acid (0.5 mg), glutamic acid (2 mg) and EC (0.5 mg). Final pH of preparation was 7.4. Radiochemical purity was determined by TLC (ITLC SG, Gelman Sciences, Ann Arbor, Mich.) eluted with, respectively ammonium acetate (1M in water): methanol (4:1). From radio-TLC (Bioscan, Washington, D.C.) analysis, the radiochemical purity was >95%.

d. In Vitro Cellular Uptake Assays and Tissue Distribution Studies

Figure 16:
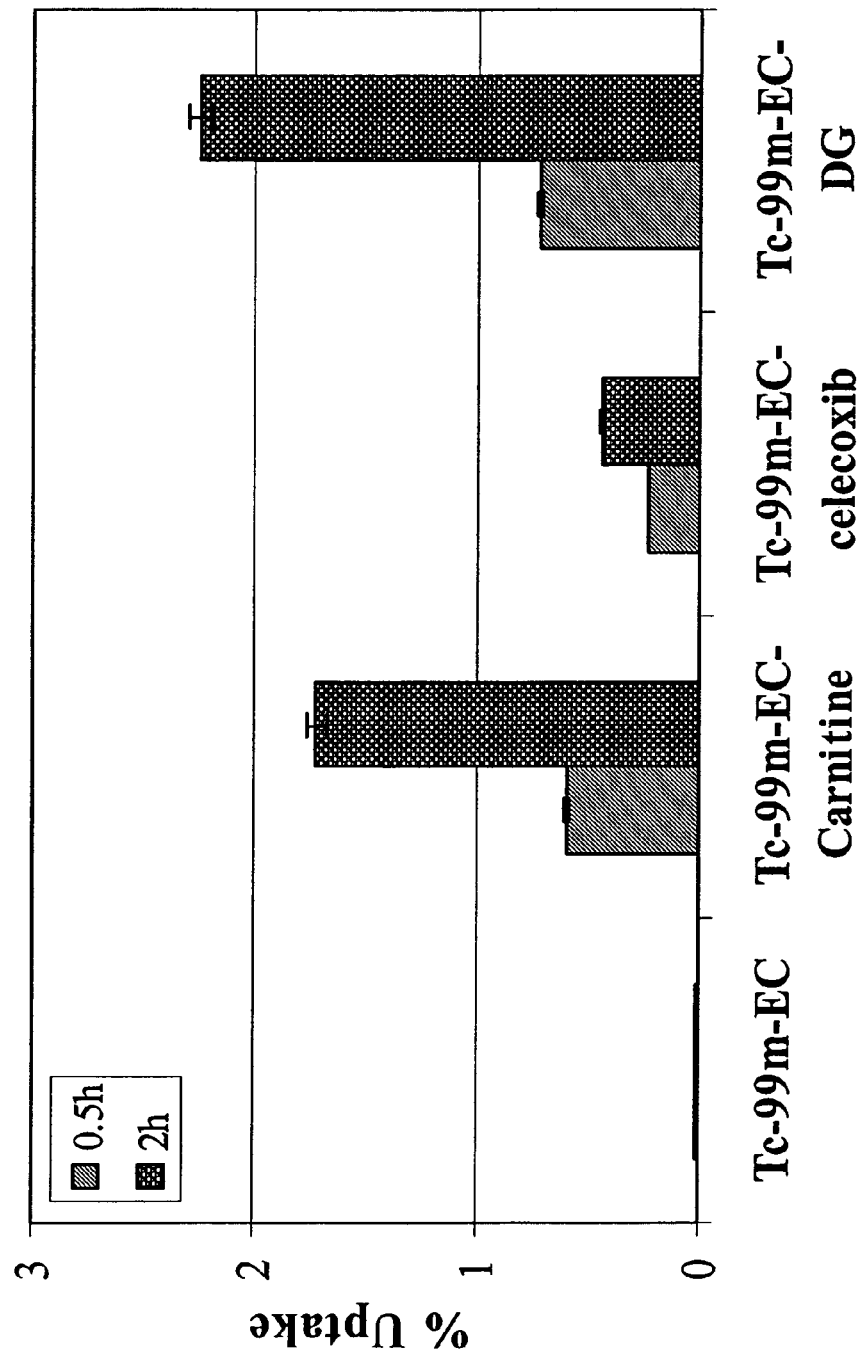
FIG. 16: In vitro cellular uptake of $^{99m}$Tc-EC-agents in breast cancer cells.

An in vitro cell culture using tumor cells was incubated with $^{99m}$Tc-EC-celecoxib (4 μCi/50,000 cells/well) at 0.5-2 hrs in RBA CRL-1747. There was a significant increase in uptake compared to $^{99m}$Tc-EC (FIGS. 1 and 16).

Biodistribution was assessed in mammary tumor-bearing rats (RBA CRL-1747, n=3/time interval, iv). Studies were performed 14 to 17 days after implantation when tumors reached approximately 1 cm in diameter. Following administration of the radiotracer, rats were sacrificed at 0.5-4 hrs. The selected tissues were excised, weighed and counted for radioactivity by using a gamma counter (Packard Instruments, Downers Grove, Ill.). The biodistribution of tracer in each sample was calculated as percentage of the injected dose per gram of tissue wet weight (% ID/g). Biodistribution of $^{99m}$Tc-EC-celecoxib in tumor-bearing rats showed increased tumor-to-tissue count density ratios as a function of time compared to $^{99m}$Tc-EC (Tables 2 and 3).

TABLE 2

Biodistribution of $^{99m}$Tc-EC in Breast Tumor Bearing Rats

|  | 30 Min. | 1 Hour | 2 Hour | 4 Hour |
| --- | --- | --- | --- | --- |
| Blood | 0.435 ± 0.29 | 0.273 ± 0.039 | 0.211 ± 0.001 | 0.149 ± 0.008 |
| Lung | 0.272 ± 0.019 | 0.187 ± 0.029 | 0.144 ± 0.002 | 0.120 ± 0.012 |
| Liver | 0.508 ± 0.062 | 0.367 ± 0.006 | 0.286 ± 0.073 | 0.234 ± 0.016 |
| Stomach | 0.136 ± 0.060 | 0.127 ± 0.106 | 0.037 ± 0.027 | 0.043 ± 0.014 |
| Kidney | 7.914 ± 0.896 | 8.991 ± 0.268 | 9.116 ± 0.053 | 7.834 ± 1.018 |
| Thyroid | 0.219 ± 0.036 | 0.229 ± 0.118 | 0.106 ± 0.003 | 0.082 ± 0.005 |
| Muscle | 0.060 ± 0.006 | 0.043 ± 0.002 | 0.028 ± 0.009 | 0.019 ± 0.001 |
| Intestine | 0.173 ± 0.029 | 0.787 ± 0.106 | 0.401 ± 0.093 | 0.103 ± 0.009 |
| Urine | 9.124 ± 0.808 | 11.045 ± 6.158 | 13.192 ± 4.505 | 8.693 ± 2.981 |
| Tumor | 0.342 ± 0.163 | 0.149 ± 0.020 | 0.115 ± 0.002 | 0.096 ± 0.005 |
| Tumor/Blood | 0.776 ± 0.322 | 0.544 ± 0.004 | 0.546 ± 0.010 | 0.649 ± 0.005 |
| Tumor/Muscle | 5.841 ± 3.253 | 3.414 ± 0.325 | 4.425 ± 1.397 | 5.093 ± 0.223 |
| Tumor/Lung | 1.256 ± 0.430 | 0.797 ± 0.022 | 0.797 ± 0.002 | 0.798 ± 0.007 |

Values shown represent the mean ± standard deviation of data from 3 animals.

TABLE 3

Biodistribution of $^{99m}$Tc-EC-celecoxib in Breast Tumor-Bearing Rats % of injected dose per gram of tissue weight (n = 3/time, interval, iv)

|  | 30 min | 2 h | 4 h |
| --- | --- | --- | --- |
| BLOOD | 2.293 ± 0.038 | 1.388 ± 0.063 | 1.031 ± 0.033 |
| HEART | 0.475 ± 0.025 | 0.283 ± 0.017 | 0.224 ± 0.004 |
| LUNG | 1.033 ± 0.035 | 0.712 ± 0.018 | 0.500 ± 0.011 |
| LIVER | 1.556 ± 0.046 | 1.461 ± 0.049 | 1.506 ± 0.080 |
| SPLEEN | 0.594 ± 0.298 | 0.965 ± 0.056 | 0.981 ± 0.041 |
| KIDNEY | 4.963 ± 0.147 | 6.088 ± 0.305 | 6.363 ± 0.260 |
| INTESTINE | 0.406 ± 0.039 | 0.276 ± 0.061 | 0.190 ± 0.006 |
| UTERUS | 0.595 ± 0.003 | 0.334 ± 0.034 | 0.263 ± 0.005 |
| MUSCLE | 0.133 ± 0.007 | 0.062 ± 0.003 | 0.002 ± 0.004 |
| TUMOR | 0.587 ± 0.062 | 0.424 ± 0.019 | 0.406 ± 0.004 |
| THYROID | 0.784 ± 0.090 | 0.449 ± 0.015 | 0.372 ± 0.021 |
| STOMACH | 0.370 ± 0.010 | 0.187 ± 0.004 | 0.139 ± 0.004 |
| BONE & JOINT | 0.324 ± 0.036 | 0.190 ± 0.003 | 0.178 ± 0.022 |
| TUMOR/ MUSCLE | 4.375 ± 0.304 | 6.876 ± 0.704 | 9.715 ± 0.387 |
| TUMOR/ BLOOD | 0.255 ± 0.022 | 0.307 ± 0.018 | 0.395 ± 0.014 |
| UTERUS/ BLOOD | 0.259 ± 0.003 | 0.240 ± 0.021 | 0.255 ± 0.005 |
| UTERUS/ MUSCLE | 4.471 ± 0.257 | 5.442 ± 0.852 | 6.278 ± 0.199 |
| BONE/ MUSCLE | 2.419 ± 0.225 | 3.058 ± 0.114 | 4.314 ± 0.739 |

Values shown represent the mean ± standard deviation of data from 3 animals.

e. Scintigraphic Imaging Studies

Figure 17:
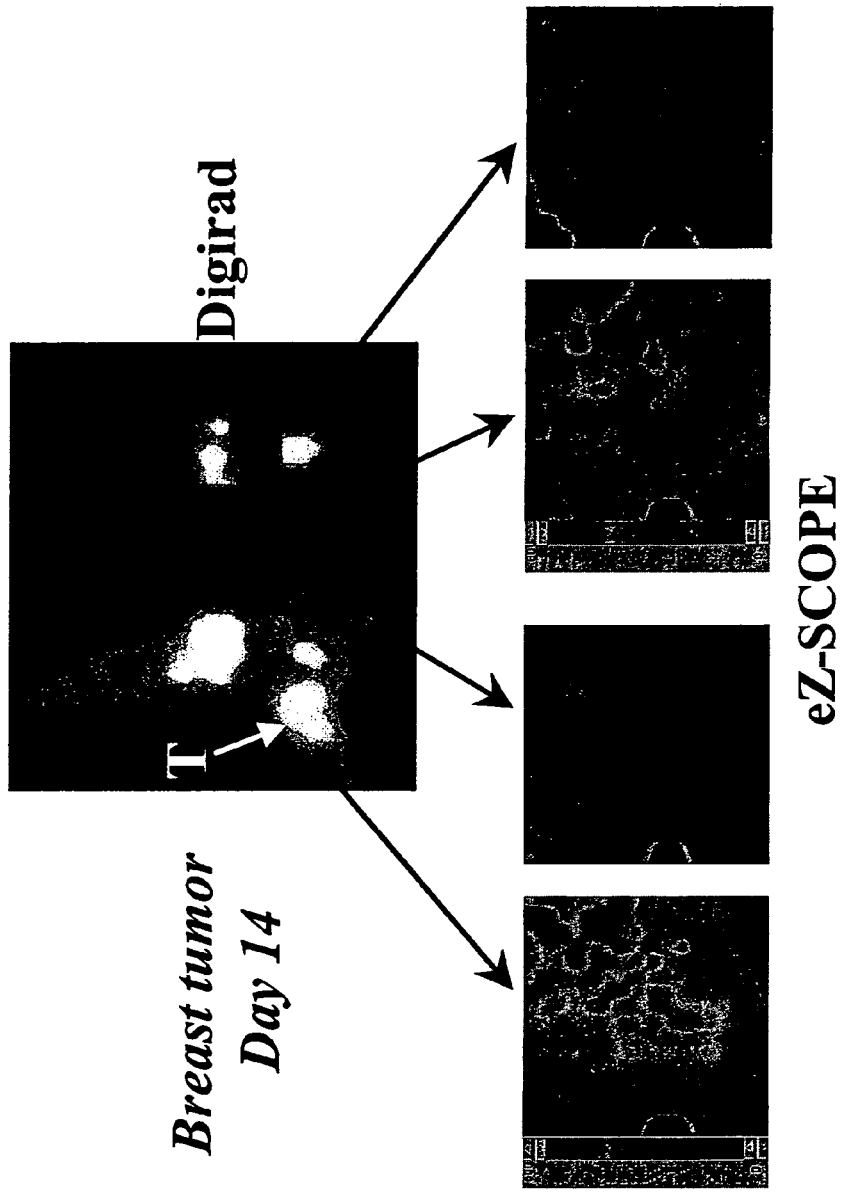
FIG. 17: Scintigraphic Images of $^{99m}$Tc-EC-celecoxib. Planar images of breast tumor-bearing rats after administration of $^{99m}$Tc-EC-celecoxib (left rat) and $^{99m}$Tc-EC (right rat) showed that tumor could be visualized using both Digirad for whole body imaging, and eZ-Scope for local imaging. T=tumor.

Scintigraphic imaging studies was performed in mammary tumor-bearing rats at 0.5-4 hrs (0.3 mCi/rat, n=3, iv). Control group was administered $^{99m}$Tc-EC. Planar images confirmed that the tumors could be visualized clearly with $^{99m}$Tc-EC-celecoxib (FIG. 17).

Figure 18:
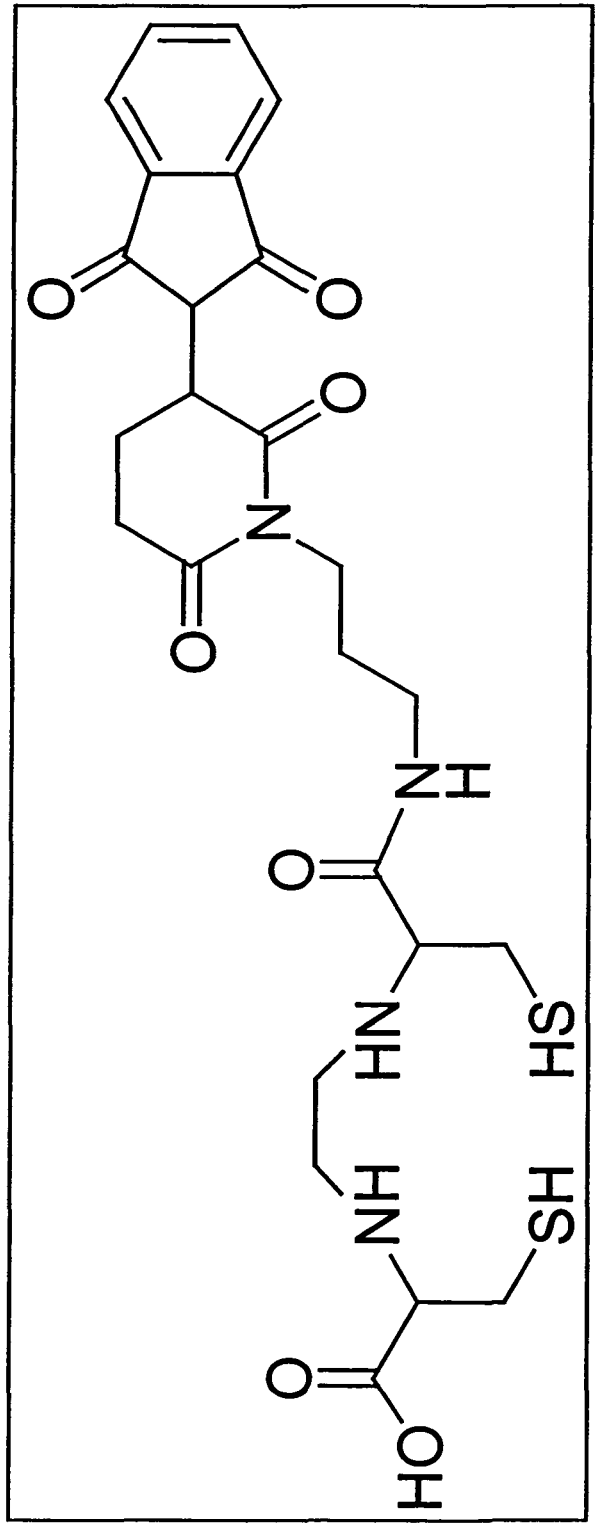
FIG. 18: Chemical structure of EC-thalidomide.
Figure 19:
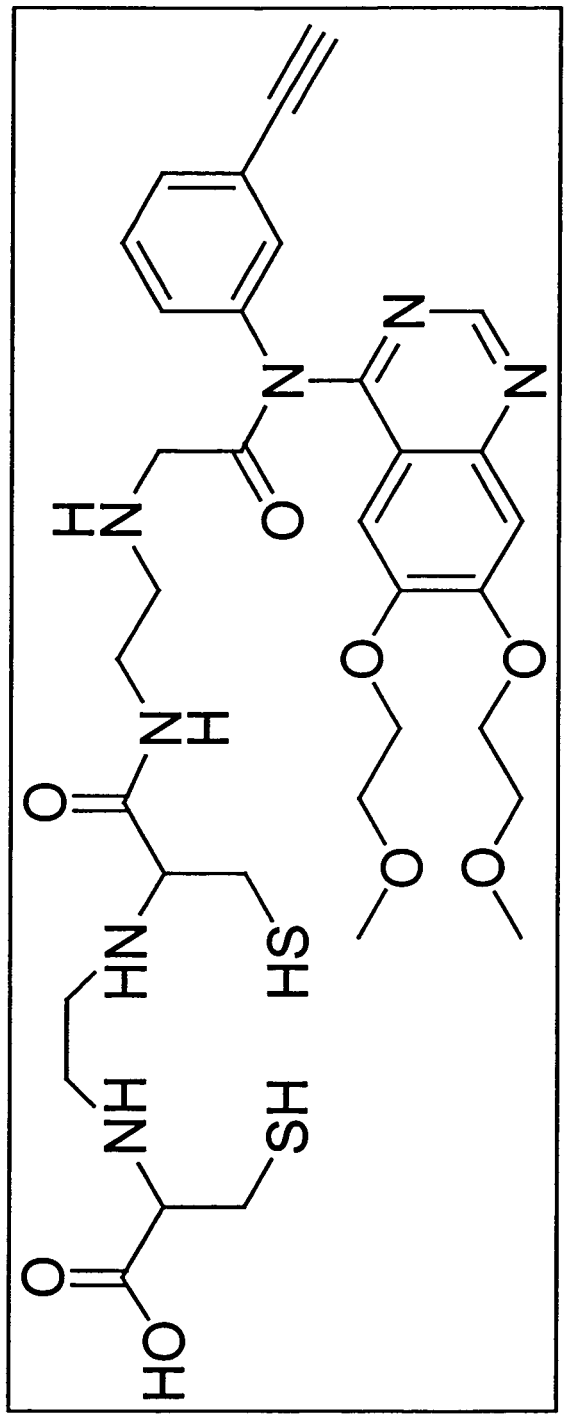
FIG. 19: Chemical structure of EC-quinazoline.

Other small molecules can be applied using the EC technology, including EC-thalidomide (anti-VEGF), EC-quinazolin analogue (anti-EGF receptor R). The structures are shown in FIGS. 18-19.

Example 4

Targeting Chromatin with EC-Penciclovir a. Synthesis of EC-Penciclovir

Figure 20:
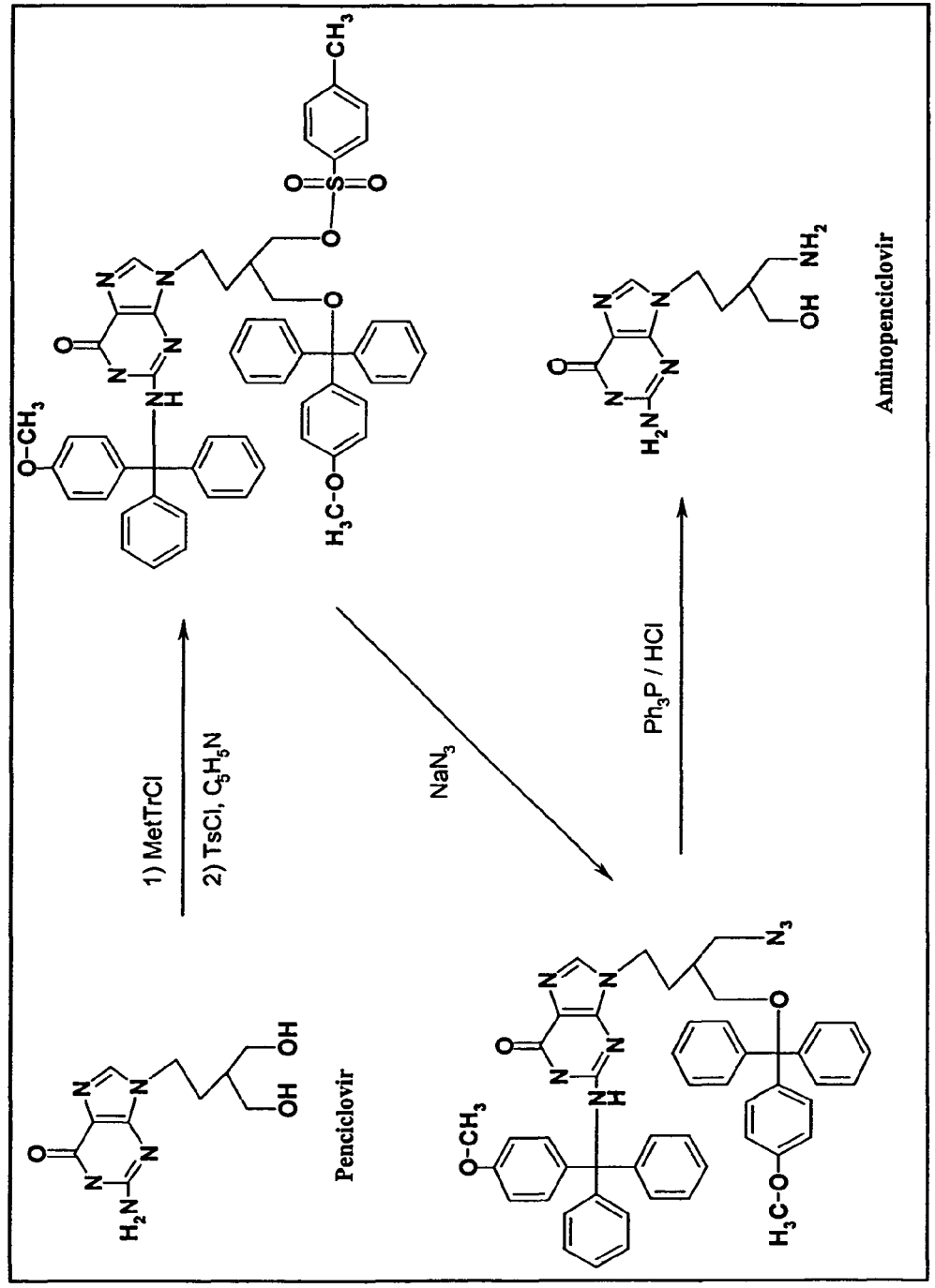
FIG. 20: Synthesis of aminopenciclovir.
Figure 21:
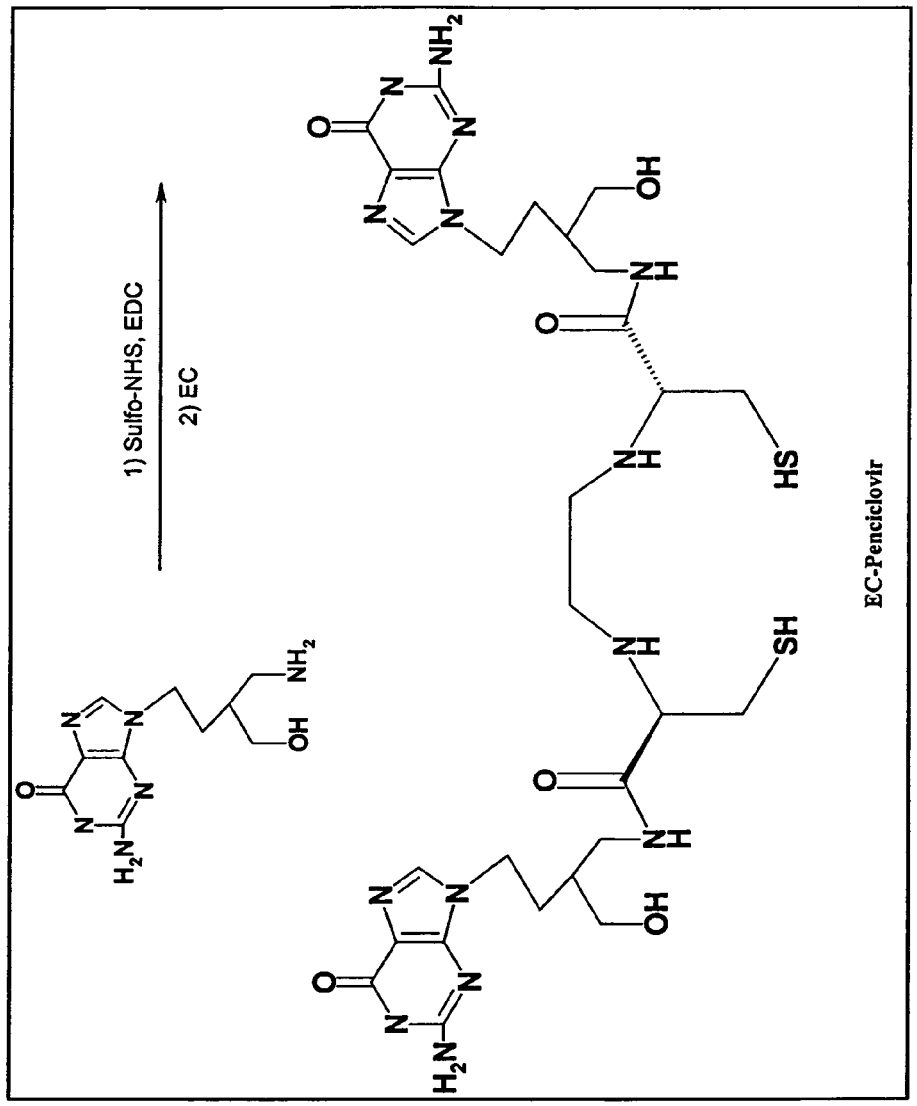
FIG. 21: Synthesis of EC-penciclovir (EC-Guanine).

Penciclovir is a guanine analogue and is used for targeting disease cell cycle targets. Synthesis of EC-Penciclovir was accomplished in a three-step manner (shown in FIGS. 20-21). The starting material, 3-N-trityl-9-(4-tosyl-3-O-tritylmethyl-butyl)guanine (penciclovir analogue), was prepared according to a published method (Allaudin 2001). Penciclovir analogue (500 mg, 0.52 mmol) was dissolved in N,N-dimethylformamide (DMF, 15 ml). To this solution, sodium azide (160 mg, 2.5 mmol) was added. The reaction was heated at 100° C. for overnight. The solvent was mixed with water and extracted with ethylacetate. The solvent was evaporated to dryness under vacuo. The azido product weighed 400 mg (yield 93%). Without further purification, the azido penciclovir analogue (400 mg, 0.48 mmol) was reduced with triphenylphosphine (655 mg, 2.5 mmol) in tetrahydrofuran (THF, 15 ml). The reaction was stirred overnight. Hydrochloric acid (5N, 0.5 ml) was added and the reaction was refluxed for 5 hours. The solvent was then evaporated. The reaction mixture was washed with water and extracted with ethylacetate. The water layer was collected and pH was adjusted to 7-8 using NaHCO$_3$ (1N). After freeze drying, the amino penciclovir analogue weighed 120 mg (90%).

To a stirred solution of EC (50 mg, 0.2 mmol) in NaHCO$_3$ (1N) (2 ml), sulfo-NHS (95.5 mg, 0.44 mmol) and EDC (84.5 mg, 0.44 mmol) were added. The amino penciclovir analogue containing saline (350 mg, 1.38 mmol) was then added. The mixture was stirred at room temperature for 24 hours. The mixture was dialyzed for 48 hours using Spectra/POR molecular porous membrane with molecule cut-off at 500 (Spectrum Medical Industries Inc., Houston, Tex.). After dialysis, the product was freeze dried. The product weighed 100 mg (yield 67%).

b. In Vitro Cellular Uptake Assays

Figure 22:
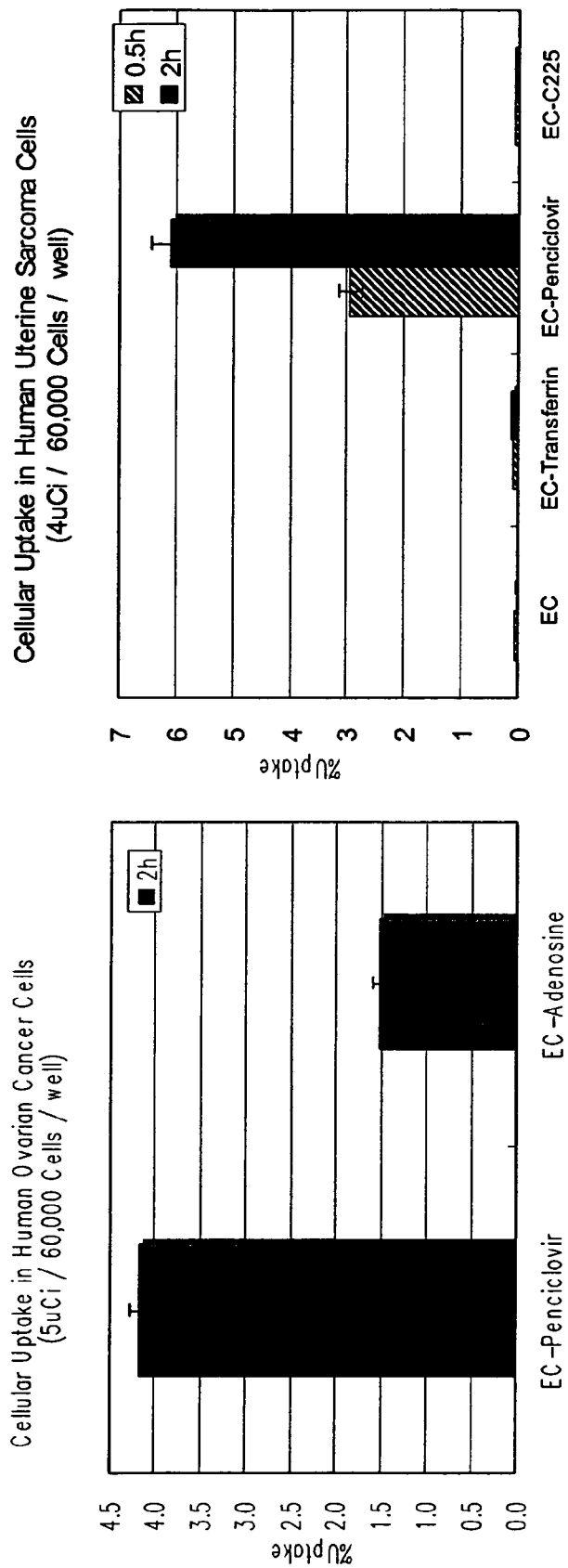
FIG. 22: In vitro cellular uptake of $^{99m}$Tc-EC-penciclovir (99mTc-EC-Guanine) in human cancer cell lines. In vitro cell culture of $^{99m}$Tc-EC-Penciclovir showed high uptake in both cell lines tested.

An in vitro cell culture using tumor cells was incubated with $^{99m}$Tc-EC-penciclovir (4-6 µCi/50,000 cells/well) at 0.5-2 hrs in human ovarian and uterine cancer cells. There was a significant increased uptake compared to $^{99m}$Tc-EC (FIG. 22).

c. Scintigraphic Imaging Studies

Figure 23:
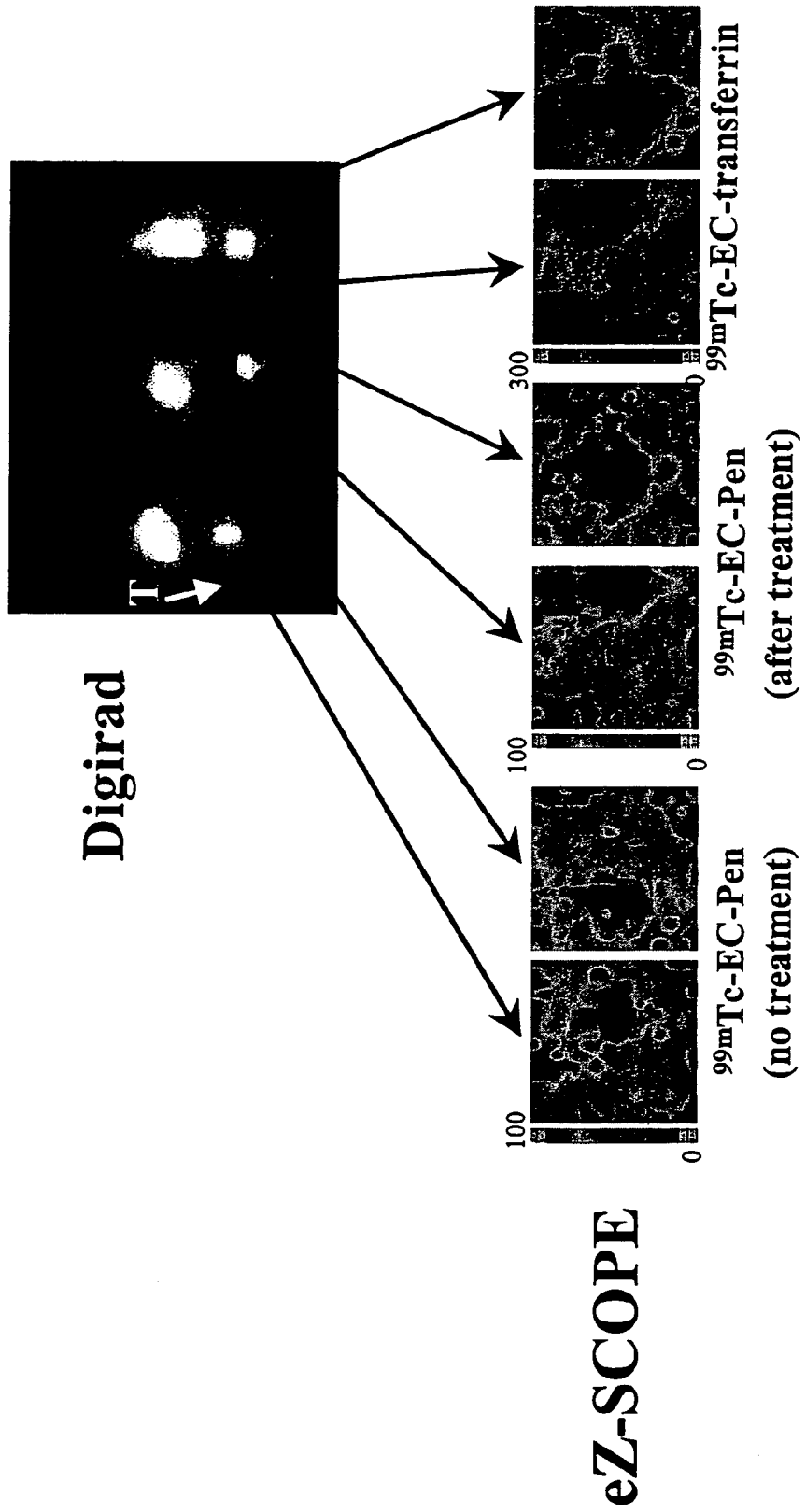
FIG. 23: Scintigraphic images of $^{99m}$Tc-EC-penciclovir ($^{99m}$Tc-EC-Guanine). Planar images of uterine sarcoma-bearing nude mice after administration of $^{99m}$Tc-EC-penciclovir (left and middle mice) and $^{99m}$Tc-EC-transferrin (right rat) showed that tumor could be visualized using both Digirad for whole body imaging, and eZ-Scope for local imaging. Middle mouse was treated with paclitaxel (60 mg/kg). T=tumor.
Figure 24:
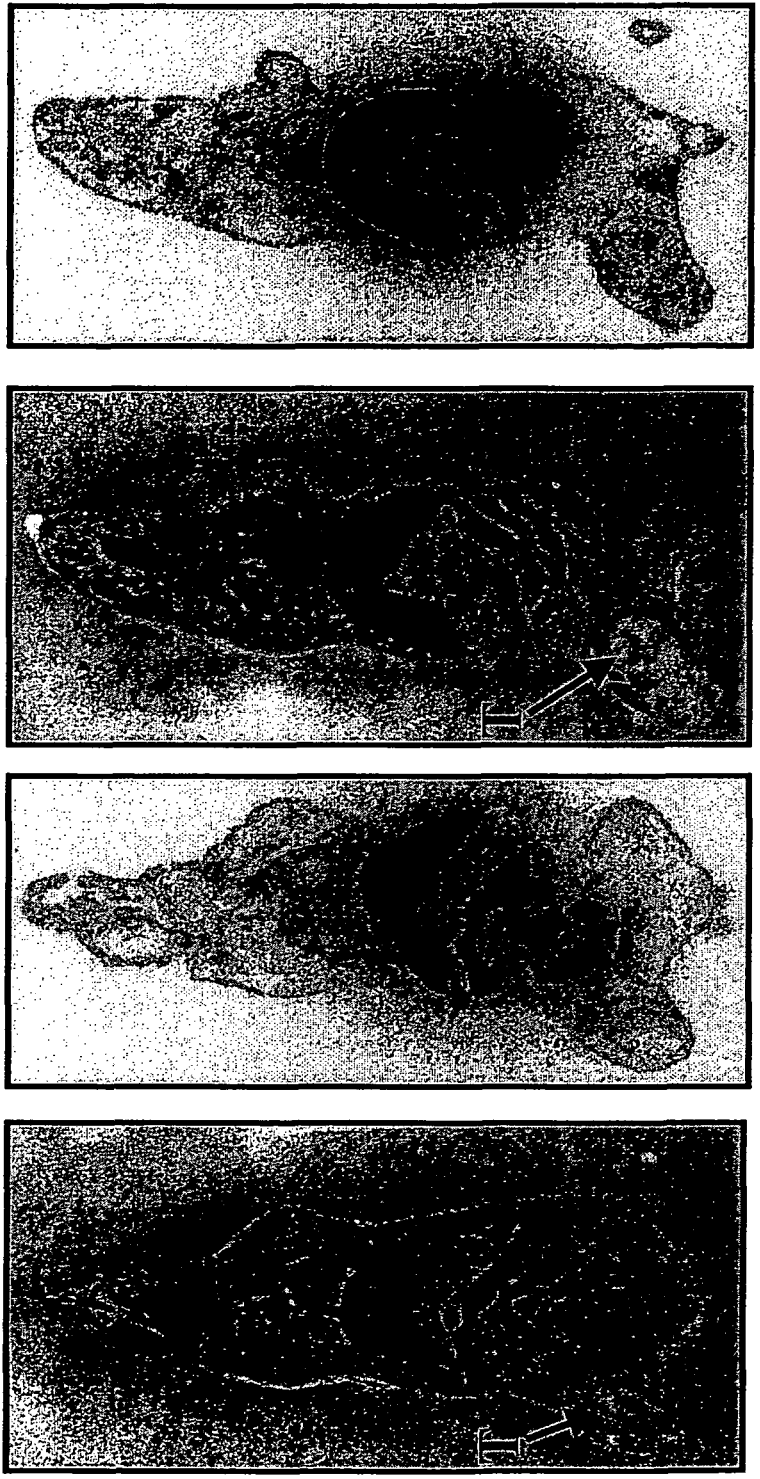
FIG. 24: Autoradiogram of $^{99m}$Tc-EC-penciclovir ($^{99m}$Tc-EC-Guanine). Doxorubicin-sensitive uterine sarcoma-bearing nude mice were injected with 100 μCi of $^{99m}$Tc-EC-penciclovir pre- (left) and post- (right) paclitaxel treatment (60 mg/kg) and sacrificed 60 min post injection. Sections were cut at 100 μm and exposed for 16 hrs. Arrow designates tumor site.

Scintigraphic imaging studies were performed in human uterine tumor-bearing mice at 0.5-4 hrs (0.1 mCi/rat, n=3, iv). Control group was administered $^{99m}$Tc-EC. Planar images confirmed that the tumors could be visualized with $^{99m}$Tc-EC-penciclovir (FIG. 23). Whole-body autoradiogram was obtained by a quantitative image analyzer (Cyclone Storage Phosphor System, Packard, Meridian, Conn.). Following i.v. injection of 0.1 m Ci of $^{99m}$Tc-EC-penciclovir, the animal was killed at 1 h and the body was fixed in carboxymethyl cellulose (4%). The frozen body was mounted onto a cryostat (LKB 2250 cryomicrotome) and cut into 100 μm coronal sections. Each section was thawed and mounted on a slide. The slide was then placed in contact with multipurpose phosphor storage screen (MP, 7001480) and exposed for 15 hrs. Autoradiograms performed at 1 hr after injection of $^{99m}$Tc-EC-penciclovir demonstrated the tumor activity (FIG. 24).

Figure 25:
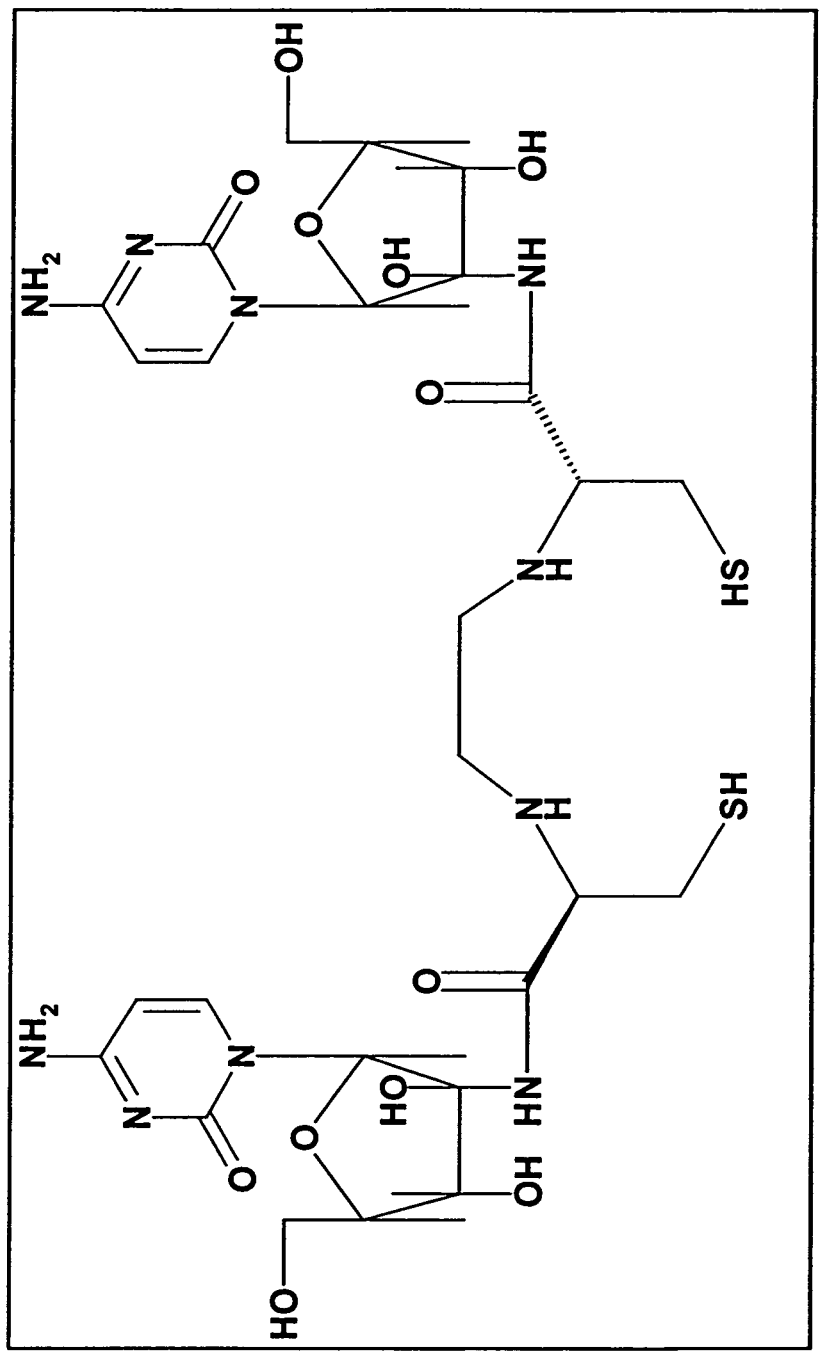
FIG. 25: Chemical structure of EC-deoxycytidine.
Figure 26:
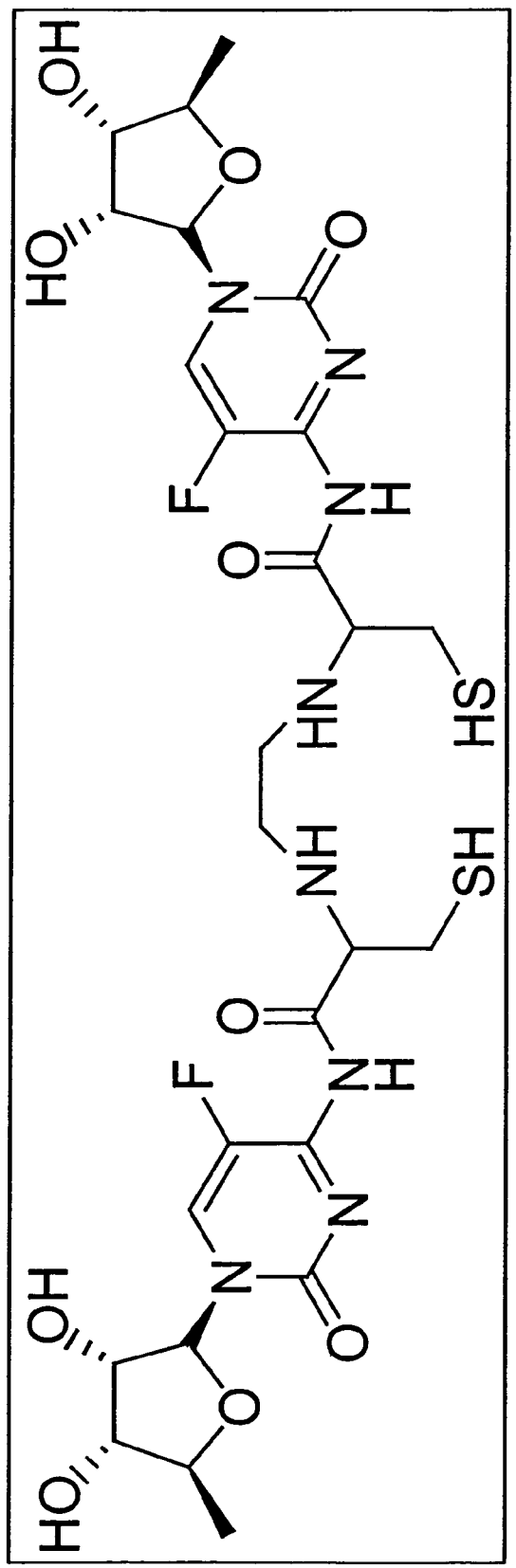
FIG. 26: Chemical structure of capecitabine.

Other small molecules that can be applied using EC technology under this example, including EC-deoxyciytidine, EC-capcitabine (cytidine analogue). The structures are shown in FIGS. 25-26.

Example 5

Targeting Chromatin with EC-Adenosine a. Synthesis of EC-Adenosine

Figure 27:
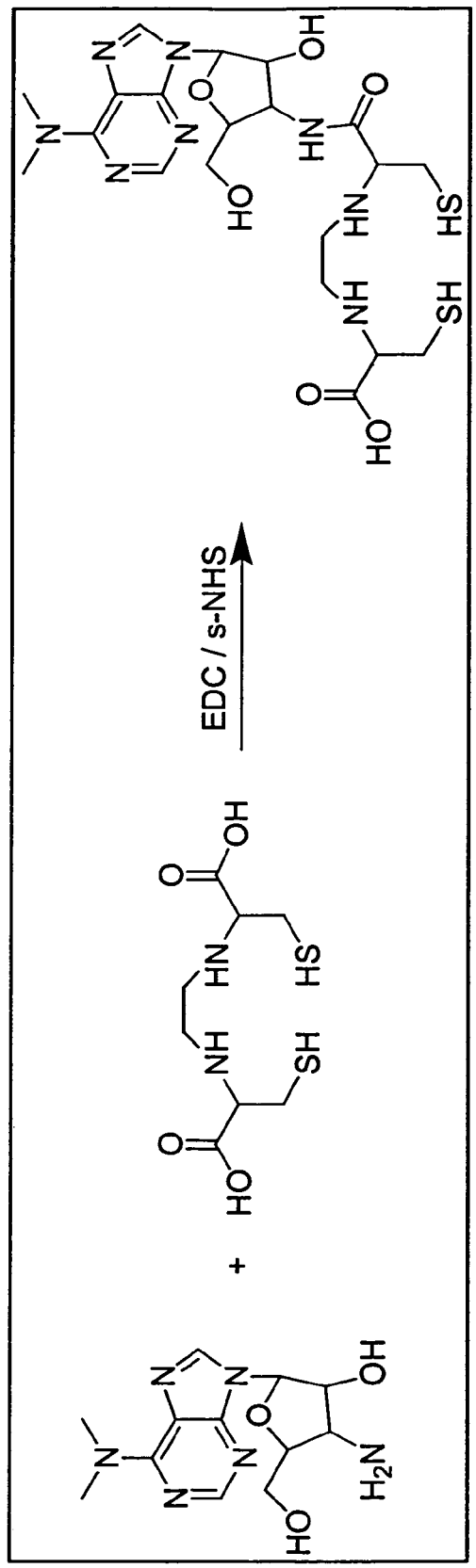
FIG. 27: Synthesis of EC-adenosine.

Chromatin is a disease cell cycle target that can be targeted with EC-adenosin, a compound of the present invention. To a stirred solution of EC (45.6 mg, 0.17 mmol) in NaHCO$_3$ (1N) (0.7 ml), sulfo-NHS (80.3 mg, 0.37 mmol) and EDC (71.0 mg, 0.37 mmol) were added. The starting material, N,N-dimethyl-3'-amino adenosine (amino adenosine analogue) (50 mg, 0.17 mmol) was then added. The mixture was stirred at room temperature for 24 hours. The mixture was dialyzed for 48 hours using Spectra/POR molecular porous membrane with molecule cut-off at 500 (Spectrum Medical Industries Inc., Houston, Tex.). After dialysis, the product was freeze dried. The product weighed 65.2 mg (yield 69.4%). Synthesis of EC-Adenosine (EC-ADN) is shown in FIG. 27.

b. In Vitro Cellular Uptake Assays

An in vitro cell culture using tumor cells was incubated with $^{99m}$Tc-EC-adenosine (4-6 μCi/50,000 cells/well) at 0.5-2 hrs in human ovarian cancer cells. There was a significant increased uptake compared to $^{99m}$Tc-EC (FIG. 22).

c. Autoradiogram Studies

Figure 28:
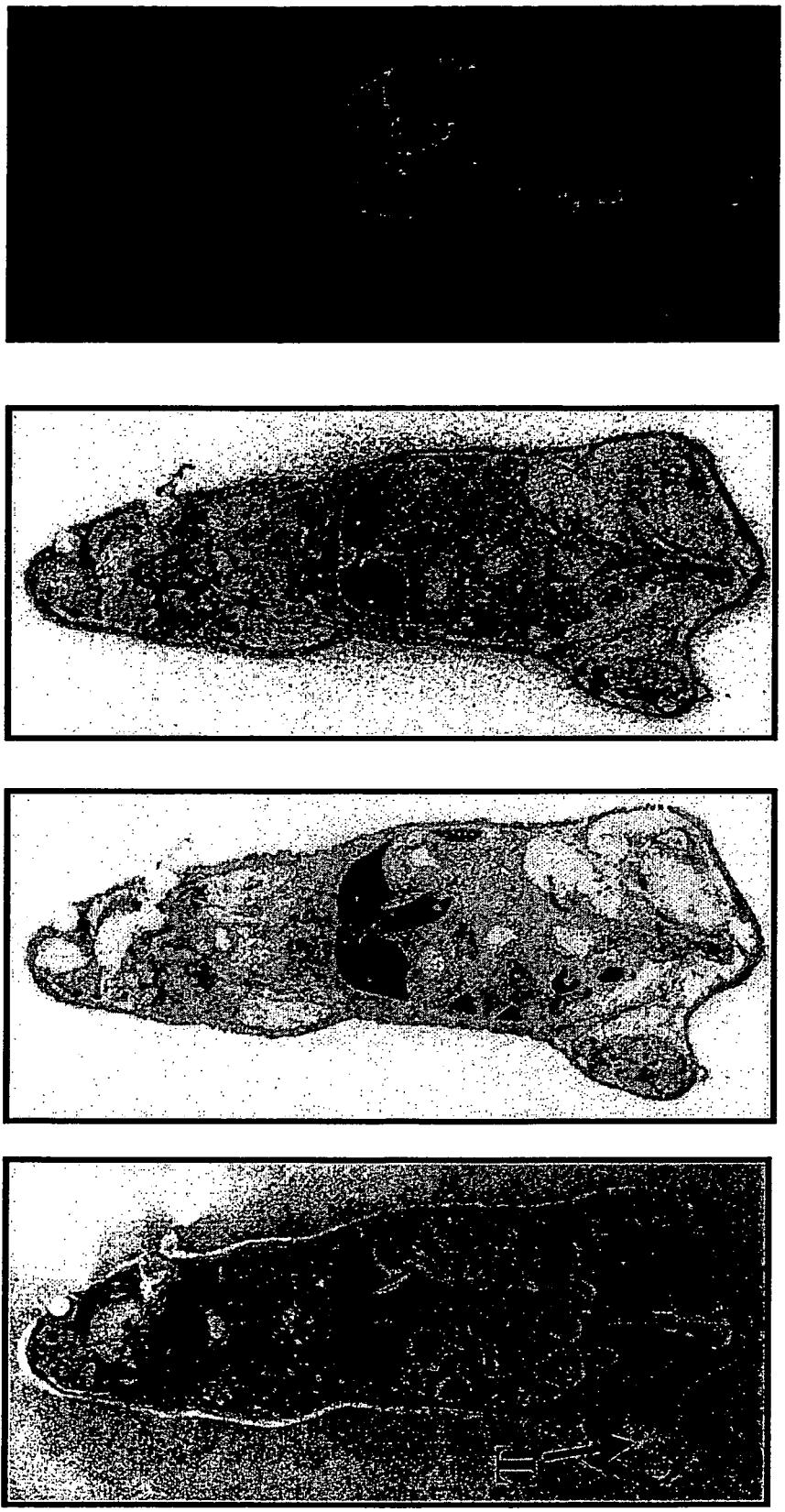
FIG. 28: Autoradiogram of 99mTc-EC-adenosine. Doxorubicin-sensitive uterine sarcoma-bearing nude mice were injected with 100 μCi of $^{99m}$Tc-EC-adenosine and sacrificed 48 min post injection. Sections were cut at 100 μm and exposed for 16 hrs. Arrow designates tumor site.

Whole-body autoradiogram was obtained by a quantitative image analyzer (Cyclone Storage Phosphor System, Packard, Meridian, Conn.). Following i.v. injection of 0.1 mCi of $^{99m}$Tc-EC-adenosine, animal was killed at 1 hr and the body was fixed in carboxymethyl cellulose (4%). The frozen body was mounted onto a cryostat (LKB 2250 cryomicrotome) and cut into 100 μm coronal sections. Each section was thawed and mounted on a slide. The slide was then placed in contact with multipurpose phosphor storage screen (MP, 7001480) and exposed for 15 hrs. Autoradiograms performed at 1 hr after injection of $^{99m}$Tc-EC-adenosine demonstrated the tumor activity (FIG. 28).

Example 6

Targeting GnRH Receptors with EC-LHRH a. Synthesis of EC-LHRH

The GnRH receptor is a disease tissue receptor that can be targeted with EC-LHRH, a compound of the current invention. To a stirred solution of EC (4.6 mg, 0.017 mmol) in NaHCO$_3$ (1N) (0.5 ml), sulfo-NHS (3.72 mg, 0.017 mmol) and EDC (3.3 mg, 0.017 mmol) were added. The starting material, luteinizing hormone releasing hormone (LHRH human, Sigma Chemical Company, St. Louis, Mo.) (50 mg, 0.042 mmol) was then added. The mixture was stirred at room temperature for 24 hours. The mixture was dialyzed for 48 hours using Spectra/POR molecular porous membrane with molecule cut-off at 1,000 (Spectrum Medical Industries Inc., Houston, Tex.). After dialysis, the product was freeze dried. The product weighed 51 mg (yield 93.4%).

b. In Vitro Cellular Uptake Assays

Figure 29:
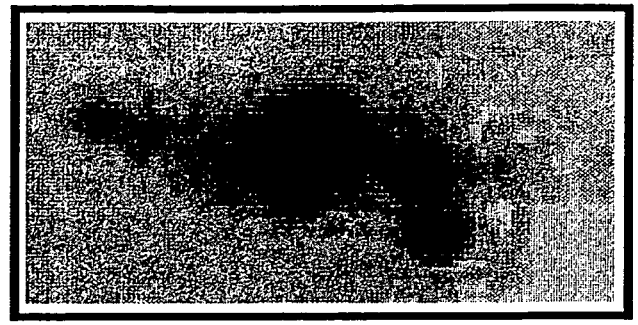
FIG. 29: Scintigraphic images of $^{99m}$Tc-EC-LHRH. Planar image of breast tumor-bearing rats after administration of $^{99m}$Tc-EC and $^{99m}$Tc-EC-LHRH (100 μCi/rat, iv.) showed that the tumor could be well visualized from 0.5-2 hours post-injection.
Figure 29:
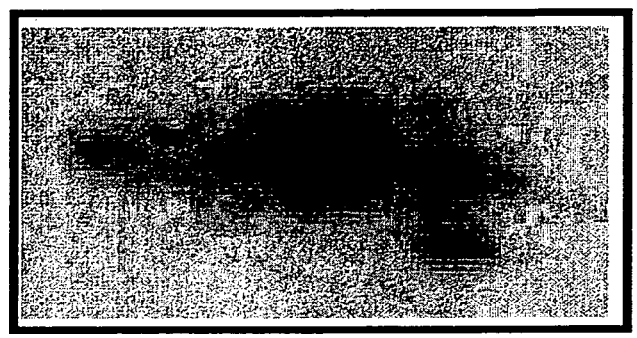
Figure 29:
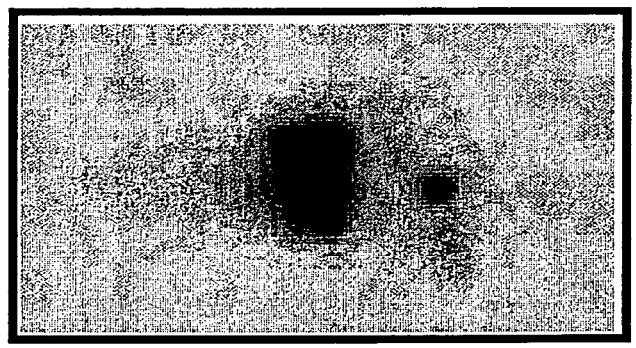
Figure 29:
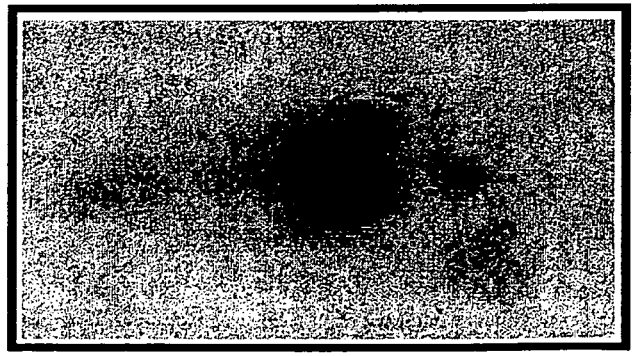

An in vitro cell culture using tumor cells was incubated with $^{99m}$Tc-EC-LHRH (4-6 μCi/100,000 cells/well) at 0.5-2 hrs in human prostate cancer cells. Two types cell lines were used. They are either sensitive to androgen (LNCap) or unresponsive to androgen (PC-3) therapy. There was a significant increased uptake compared to $^{99m}$Tc-EC (FIG. 29).

c. Scintigraphic Imaging Studies

Figure 30:
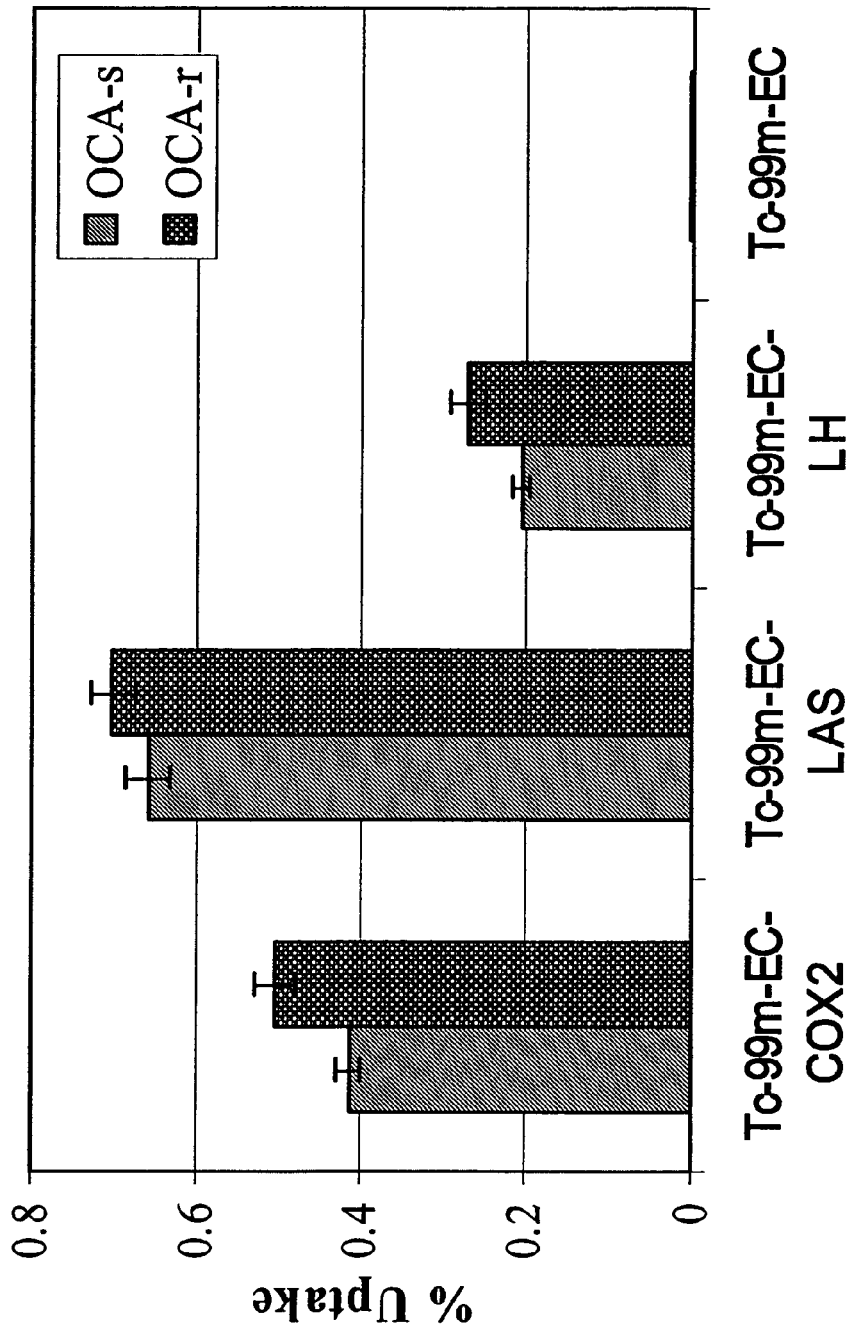
FIG. 30: In vitro cellular uptake of $^{99m}$Tc-EC-agents in human ovarian cancer cells at 2 hours.

Scintigraphic imaging studies was performed in mammary tumor-bearing rats at 0.5-4 hrs (0.1 mCi/rat, n=3, iv). Control group was administered $^{99m}$Tc-EC. Planar images confirmed that the tumors could be visualized with $^{99m}$Tc-EC-LHRH (FIG. 30).

Example 7

Targeting Luteinizing Hormone Receptors with EC-LH Antibody a. Synthesis of EC-LH Antibody The luteinizing hormone receptors are a disease tissue receptor that can be targeted with EC-LH antibody, a compound of the current invention. To a stirred solution of EC (0.51 mg, 1.90 μmol) in NaHCO$_3$ (1N) (0.1 ml), sulfo-NHS (0.41 mg, 1.9 μmol) and EDC (0.36 mg, 1.9 μmol) were added. The starting material, luteinizing hormone antibody (Sigma Chemical Company, St. Louis, Mo.) (5.1 mg) was then added. The mixture was stirred at room temperature for 18 hours. The mixture was dialyzed for 48 hours using Spectra/POR molecular porous membrane with molecule cut-off at 10,000 (Spectrum Medical Industries Inc., Houston, Tex.). After dialysis, the product was freeze dried. The product weighed 5.1 mg (yield 97%).

b. In vitro Cellular Uptake Assays and Tissue Distribution Studies

Figure 31:
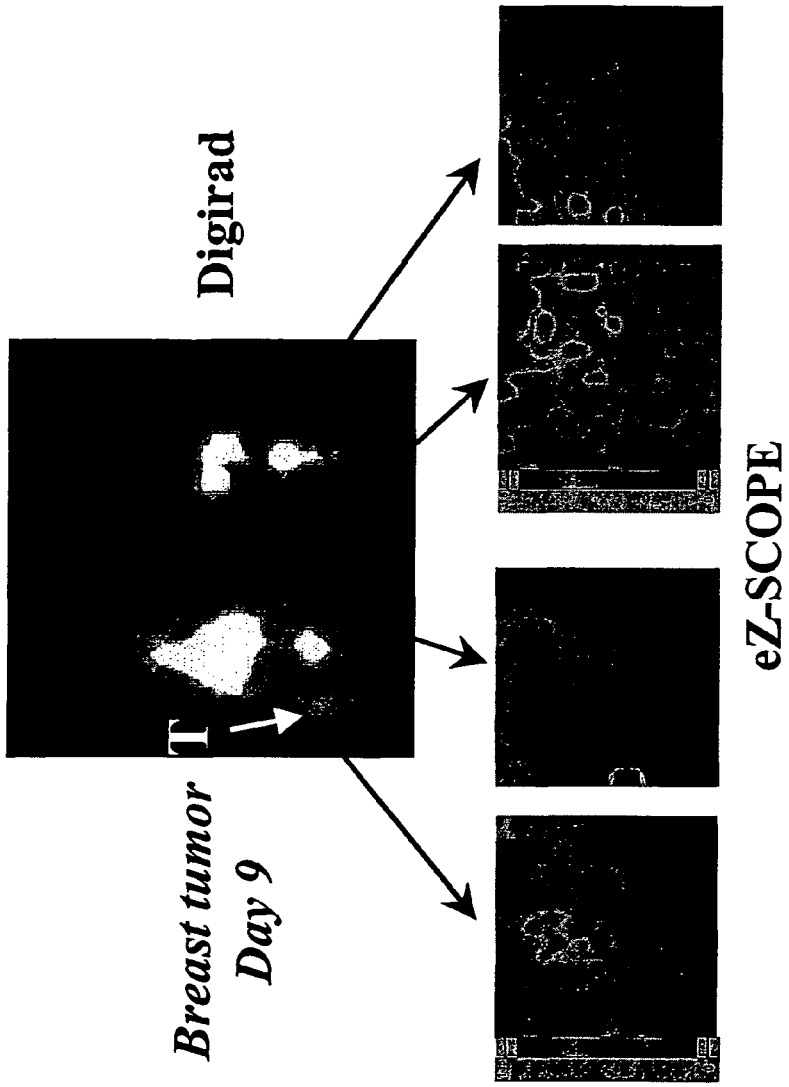
FIG. 31: Scintigraphic images of $^{99m}$Tc-EC-LH. Planar images of breast tumor-bearing rats after administration of $^{99m}$Tc-EC-LH and $^{99m}$Tc-EC showed that tumor could be visualized using both Digirad for whole body imaging, and eZ-Scope for local imaging. T=tumor.

An in vitro cell culture using tumor cells was incubated with $^{99m}$Tc-EC-LH antibody (4 μCi/50,000 cells/well) at 0.5-2 hrs in RBA CRL-1747 (breast cancer cells). There was a significant increased uptake compared to $^{99m}$Tc-EC (FIG. 31).

Biodistribution was assessed in breast tumor-bearing rats (RBA CRL-1747, n=3/time interval, iv). Studies were performed 14 to 17 days after implantation when tumors reached approximately 1 cm in diameter. Following administration of the radiotracer, rats were sacrificed at 0.5-4 hrs. The selected tissues were excised, weighed and counted for radioactivity by using a gamma counter (Packard Instruments, Downers Grove, Ill.). The biodistribution of tracer in each sample was calculated as percentage of the injected dose per gram of tissue wet weight (% ID/g). Biodistribution of $^{99m}$Tc-EC-LH antibody in tumor-bearing rats showed increased tumor-to-tissue count density ratios as a function of time compared to $^{99m}$Tc-EC (Tables 2 and 3).

TABLE 4

Biodistribution of $^{99m}$Tc-EC-LH in Breast Tumor-Bearing Rats
% of injected dose per gram of tissue weight (n = 3/time, interval, iv)

|  | 30 min | 2 h | 4 h |
| --- | --- | --- | --- |
| BLOOD | 5.368 ± 0.112 | 3.517 ± 0.058 | 2.624 ± 0.014 |
| HEART | 0.978 ± 0.114 | 0.660 ± 0.036 | 0.524 ± 0.001 |
| LUNG | 2.060 ± 0.185 | 1.343 ± 0.042 | 1.057 ± 0.018 |
| LIVER | 2.445 ± 0.089 | 1.833 ± 0.093 | 1.518 ± 0.091 |
| SPLEEN | 1.506 ± 0.117 | 1.260 ± 0.092 | 0.929 ± 0.050 |
| KIDNEY | 9.450 ± 0.313 | 12.596 ± 0.179 | 12.257 ± 0.482 |
| INTESTINE | 0.656 ± 0.073 | 0.526 ± 0.031 | 0.483 ± 0.017 |

TABLE 4-continued

Biodistribution of $^{99m}$Tc-EC-LH in Breast Tumor-Bearing Rats
% of injected dose per gram of tissue weight (n = 3/time, interval, iv)

|  | 30 min | 2 h | 4 h |
|---|---|---|---|
| UTERUS | 0.953 ± 0.044 | 0.965 ± 0.092 | 0.559 ± 0.071 |
| MUSCLE | 0.161 ± 0.012 | 0.138 ± 0.015 | 0.085 ± 0.010 |
| TUMOR | 0.776 ± 0.065 | 0.701 ± 0.029 | 0.699 ± 0.034 |
| THYROID | 0.852 ± 0.081 | 0.693 ± 0.169 | 0.762 ± 0.075 |
| STOMACH | 0.593 ± 0.103 | 0.491 ± 0.101 | 0.349 ± 0.007 |
| BONE | 0.619 ± 0.014 | 0.547 ± 0.094 | 0.359 ± 0.033 |
| TUMOR/ MUSCLE | 4.898 ± 0.599 | 5.143 ± 0.363 | 8.569 ± 1.359 |
| TUMOR/ BLOOD | 0.145 ± 0.014 | 0.200 ± 0.011 | 0.266 ± 0.014 |
| UTERUS/ BLOOD | 0.178 ± 0.010 | 0.275 ± 0.027 | 0.213 ± 0.026 |
| UTERUS/ MUSCLE | 5.951 ± 0.200 | 7.011 ± 0.391 | 6.592 ± 0.039 |
| BONE/ MUSCLE | 3.876 ± 0.213 | 4.076 ± 0.916 | 4.378 ± 0.747 |

Values shown represent the mean ± standard deviation of data from 3 animals.

c. Scintigraphic Imaging Studies

Figure 32:
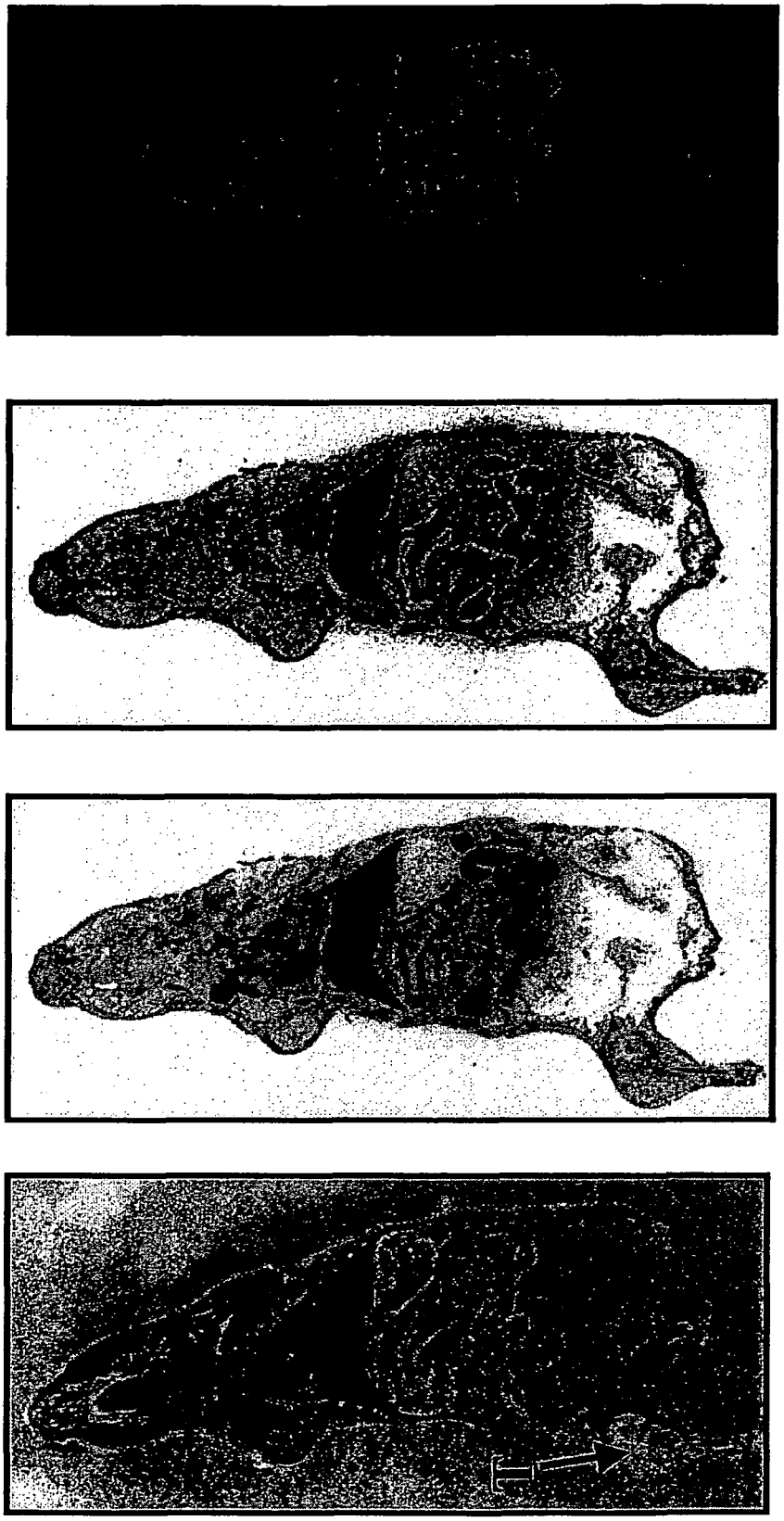
FIG. 32: Autoradiogram of $^{99m}$Tc-EC-Transferrin. Doxorubicin-sensitive uterine sarcoma-bearing nude mouse was injected with 100 µCi of $^{99m}$Tc-EC-transferrin and sacrificed 52 min post injection. Sections were cut at 100 µm and exposed for 16 hrs. Arrow designates tumor site.

Scintigraphic imaging studies was performed in breast tumor-bearing rats at 0.5-4 hrs (0.1 mCi/rat, n=3, iv). Control group was administered $^{99m}$Tc-EC. Planar images confirmed that the tumors could be visualized with $^{99m}$Tc-EC-penciclovir (FIG. 32).

Example 8

Targeting Transferrin Receptors with EC-Transferrin a. Radiosynthesis of $^{99m}$Tc-EC-Transferrin Transferrin receptors are a disease tissue receptor that can be targeted with EC-transferrin, a compound of the current invention. Transferrin (100 mg) was stirred with EC (15 mg, 0.056 mmol in 1.0 ml of 1N NaHCO$_3$), sulfo-NHS (11.6 mg, 0.056 mmol) and EDC (10.7 mg, 0.056 mmol). After dialysis (cut off at MW 10,000), 110 mg of EC-transferrin (96%) was obtained. 100 mCi of Na$^{99m}$TcO$_4$ was added into a vial containing 5 mg EC-C225 and 100 µg SnCl$_2$ and the product was purified with a G-25 column and eluted with PBS, yielded 80 mCi $^{99m}$Tc-EC-transferrin.

b. Scintigraphic Imaging and Autoradiogram Studies

Figure 33:
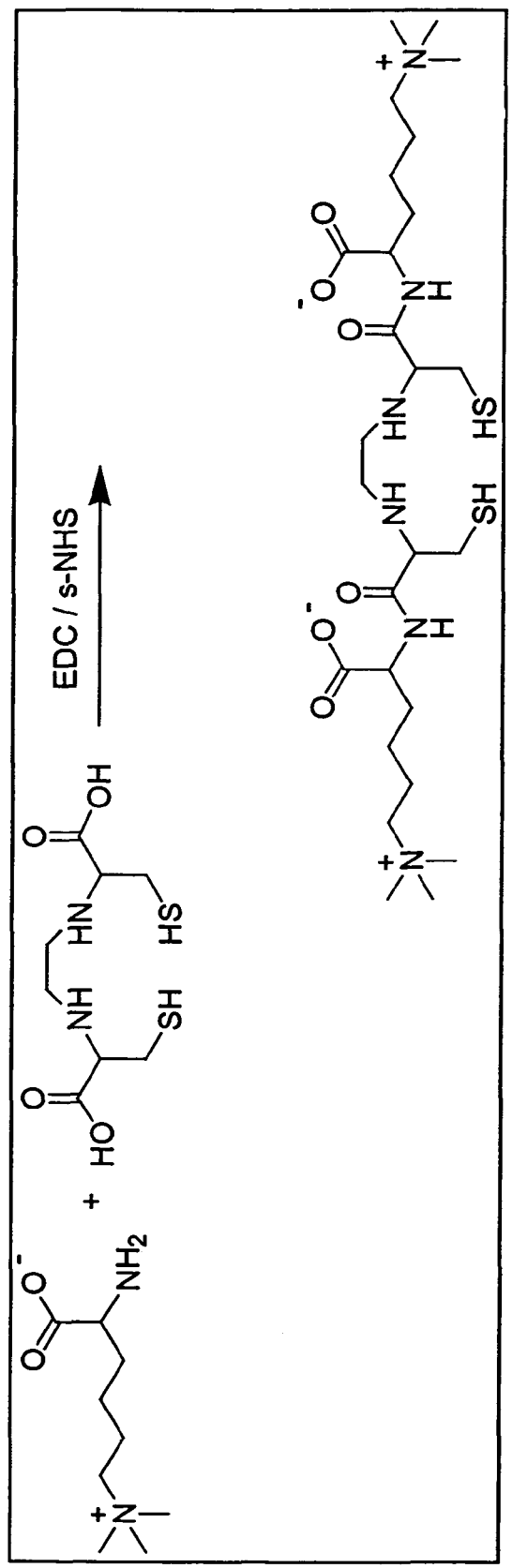
FIG. 33: Synthesis of EC-TML.

Scintigraphic imaging studies was performed in human uterine tumor-bearing mice at 0.5-4 hrs (0.1 mCi/rat, n=3, iv). Control group was administered $^{99m}$Tc-EC. Planar images confirmed that the tumors could be visualized with $^{99m}$Tc-EC-transferrin (FIG. 23). Whole-body autoradiogram was obtained by a quantitative image analyzer (Cyclone Storage Phosphor System, Packard, Meridian, Conn.). Following i.v. injection of 0.1 mCi of $^{99m}$Tc-EC-transferrin, animal was killed at 1 hr and the body was fixed in carboxymethyl cellulose (4%). The frozen body was mounted onto a cryostat (LKB 2250 cryomicrotome) and cut into 100 µm coronal sections. Each section was thawed and mounted on a slide. The slide was then placed in contact with multipurpose phosphor storage screen (MP, 7001480) and exposed for 15 hrs. Autoradiograms performed at 1 hr after injection of $^{99m}$Tc-EC-transferrin demonstrated the tumor activity (FIG. 33).

Figure 34:
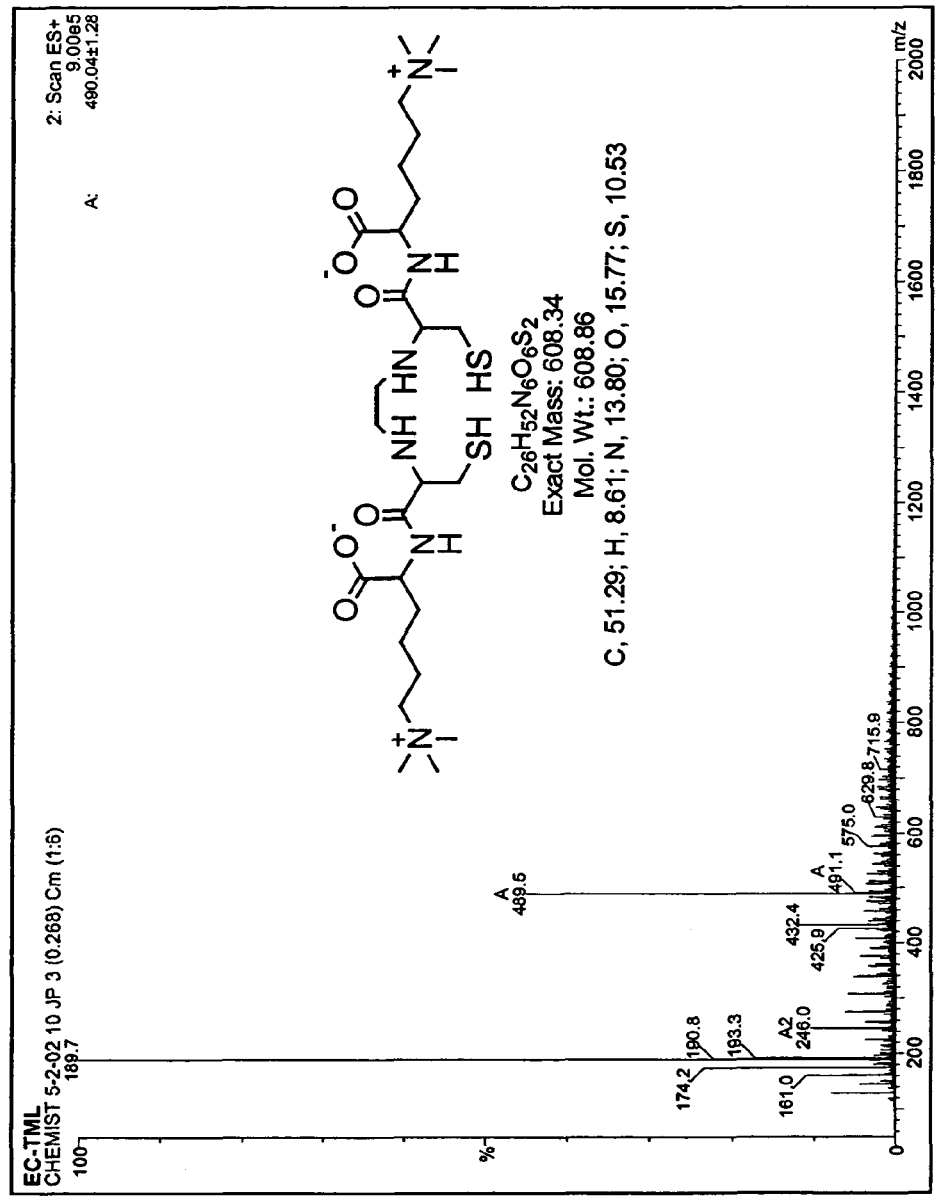
FIG. 34: Mass spectrum of EC-TML.

Other proteins and peptides can be applied using the EC technology, including EC-somatostatin, EC-caspase, EC-endorphin, EC-PSA, EC-p53, EC-octreotide (structure is shown in FIG. 34).

Example 9

Figure 35:
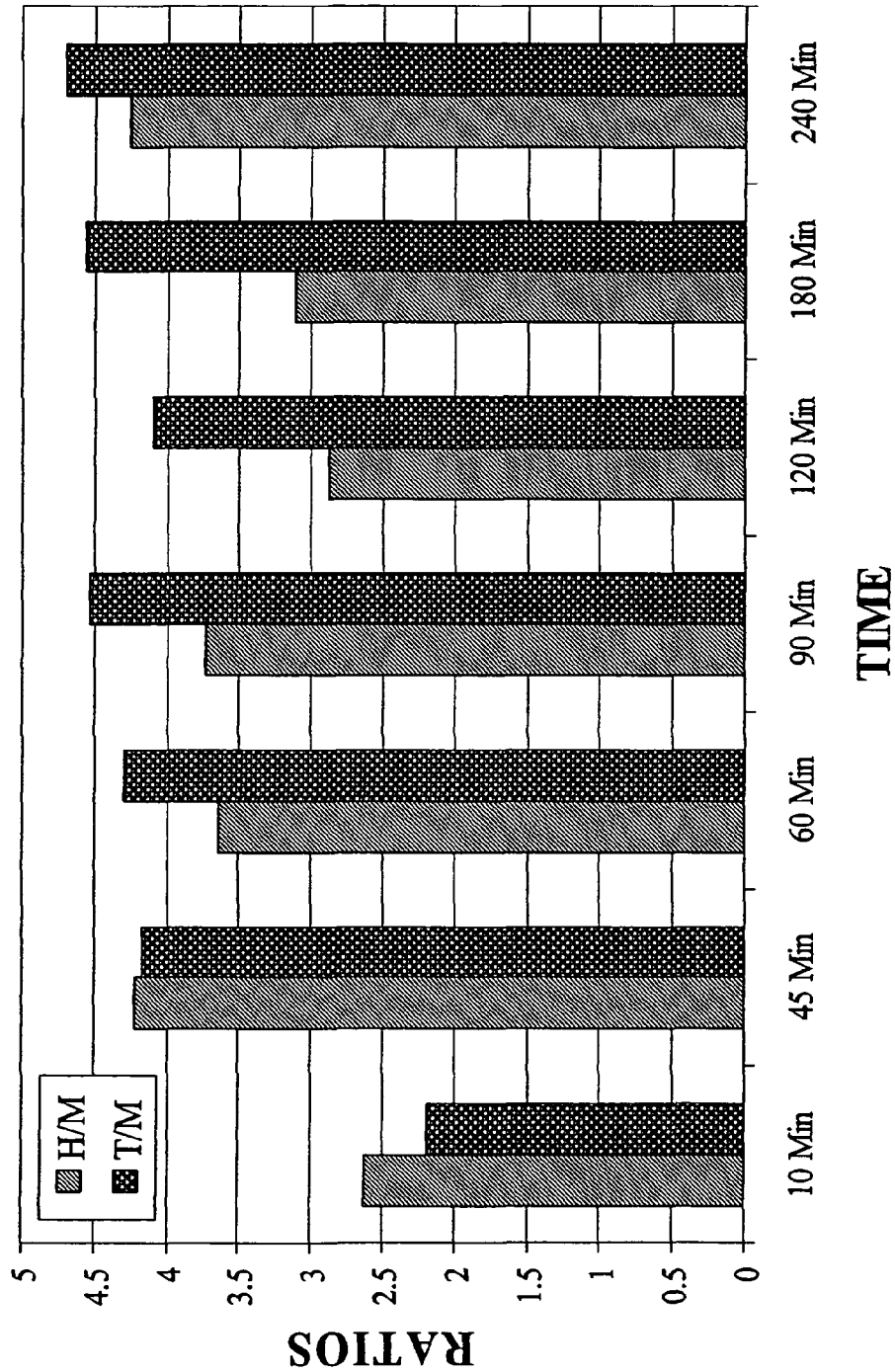
FIG. 35: Biodistribution of $^{99m}$Tc-EC-TML in breast tumor-bearing rats. In vivo biodistribution of $^{99m}$Tc-EC-TML showed high tumor/muscle and heart/muscle ratios.

Targeting Tumor Topoisomerase with EC-Doxorubicin a. Synthesis of EC-Doxorubicin The response of tissue to theraputic drugs can be targeted with the compounds of the current invention. Tumor topoisomerase is targeted with EC-doxorubicin, a compound of the current invention. To a stirred solution of EC (55.1 mg, 0.21 mmol) in NaHCO$_3$ (1N) (2 ml), sulfo-NHS (44.6 mg, 0.21 mmol) and EDC (39.4 mg, 0.21 mmol) were added. The starting material, doxorubicin (119.2 mg, 0.21 mmol) was then added. The mixture was stirred at room temperature for 24 hours. The mixture was dialyzed for 48 hours using Spectra/POR molecular porous membrane with molecule cut-off at 500 (Spectrum Medical Industries Inc., Houston, Tex.). After dialysis, the product was freeze dried. The product weighed 135 mg (yield 78%). Synthesis of EC-doxorubicin (EC-Doxo) is shown in FIG. 35.

b. In Vitro Cellular Uptake Assays

Figure 36:
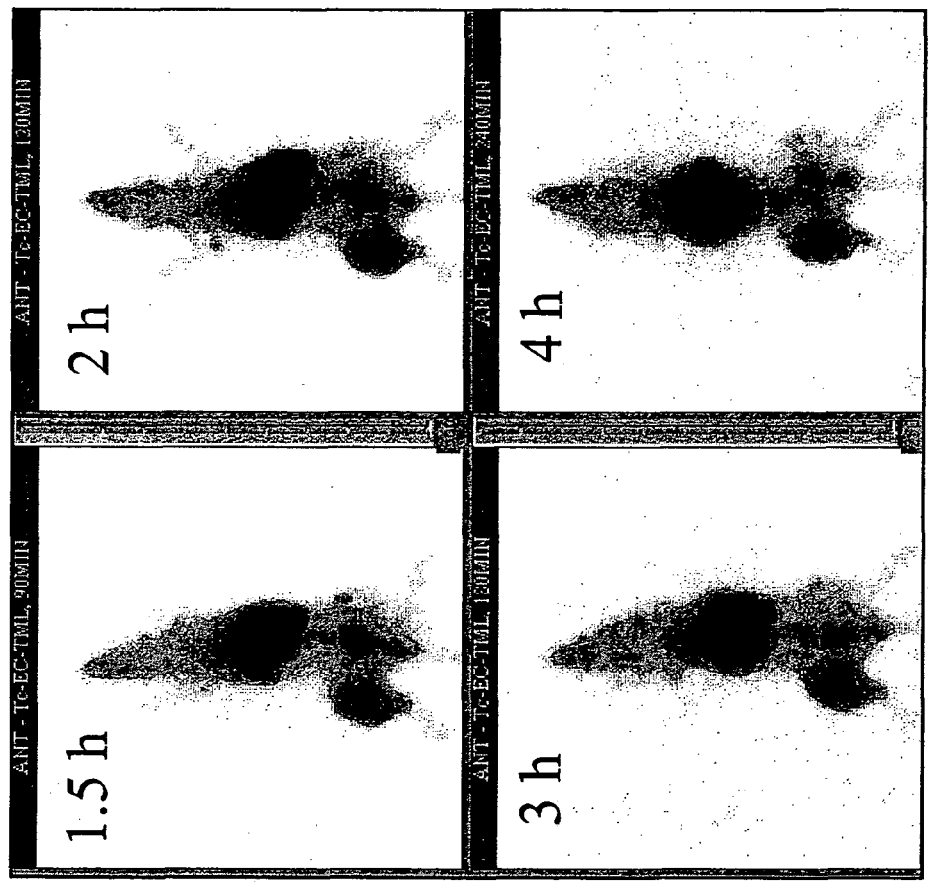
FIG. 36: Scintigraphic Images of $^{99m}$Tc-EC-TML. Planar imaging of $^{99m}$Tc-EC-TML showed tumor could be imaged from 10 min-4 hours.

An in vitro cell culture using tumor cells was incubated with $^{99m}$Tc-EC-doxorubicin (4-6 µCi/50,000 cells/well) at 0.5-2 hrs in human breast cancer cells sensitive (MDA 231, low HER2) and resistant to doxorubicin (MDA 453, high HER2). There was more uptake in doxorubicin-sensitive cells than doxorubicin-resisitant cells (FIG. 36).

Other small molecules that can be applied using EC technology under this example, including EC-paclitaxel, EC-topotecan, EC-flutamide, EC-antisense, EC-tamoxifen, EC-mitoxantrone, EC-mitomycin, EC-vancomycin, EC-bleomycin.

Example 10

Targeting Lipid Metabolism with EC-Carnitine a. Synthesis of EC-Carnitine (EC-TML)

Figure 37:
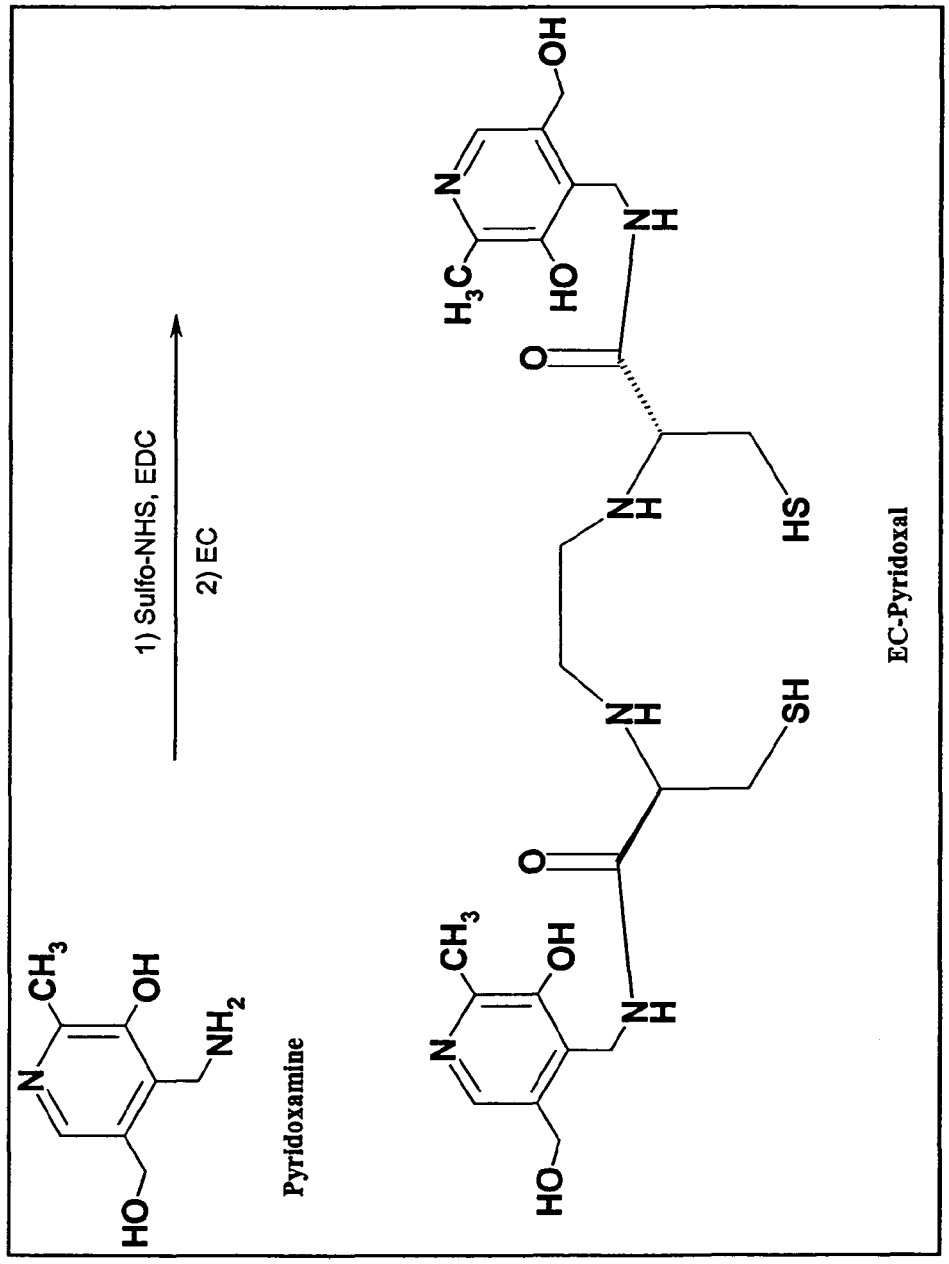
FIG. 37: Synthesis of EC-pyridoxal.
Figure 38:
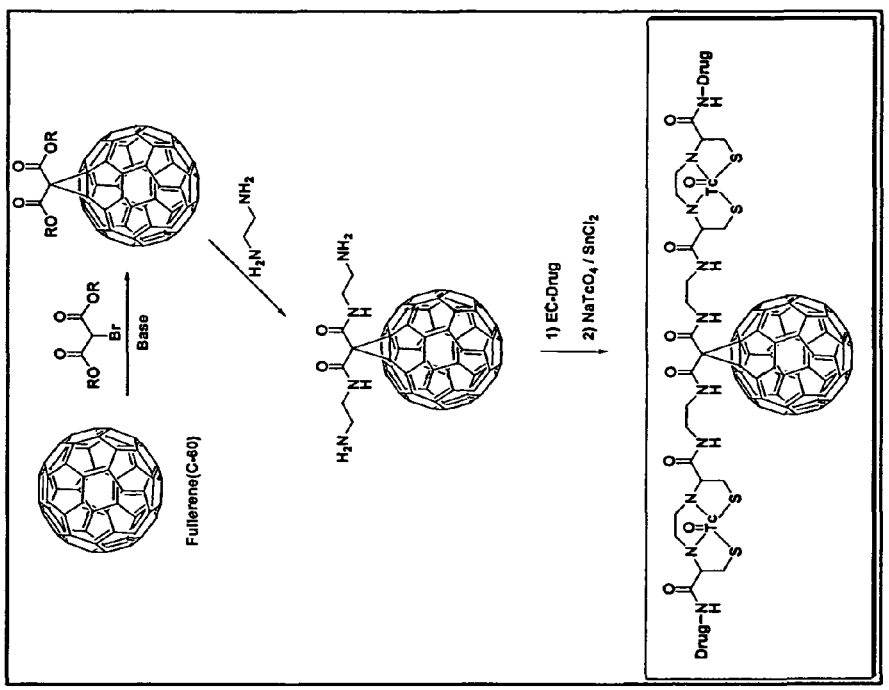
FIG. 38: Synthesis of $^{99m}$Tc-fullerene-EC-drug conjugates.

Carnitine, 2-hydroxy-3-trimethylammonium butyrate, is important for the oxidation of fatty acid and is an example of targeting disease signal transduction pathways. 6-Trimethylammonium lysine (TML) is an analogue of carnitine. EC was conjugated to amino group of TML. To a stirred solution of EC (34.9 mg, 0.13 mmol) in NaOH (1N) (0.5 ml), sulfo-NHS (62 mg, 0.29 mmol) and EDC (54.8 mg, 0.29 mmol) were added. The starting material, TML (50 mg, 0.13 mmol) was then added. The mixture was stirred at room temperature for 24 hours. The mixture was dialyzed for 48 hours using Spectra/POR molecular porous membrane with molecule cut-off at 500 (Spectrum Medical Industries Inc., Houston, Tex.). After dialysis, the product was freeze dried. The product weighed 74.2 mg (yield 93.8%). Synthesis of EC-carnitine (EC-TML) is shown in FIG. 37. Mass spectra of EC-TML is shown in FIG. 38.

b. In Vitro Cellular Uptake Assays

An in vitro cell culture using tumor cells was incubated with $^{99m}$Tc-EC-carnitine (4-6 µCi/50,000 cells/well) at 0.5-2 hrs in breast cancer cells. There was more uptake in $^{99m}$Tc-EC-carnitine than $^{99m}$Tc-EC (FIG. 16).

c. Scintigraphic Imaging Studies

Scintigraphic imaging studies was performed in breast tumor-bearing rats at 0.1-4 hrs (0.1 mCi/rat, n=3, iv). Control group was administered $^{99m}$Tc-EC. High count density ratios were observed with tumor/muscle and heart/muscle (FIG.

Figure 40:
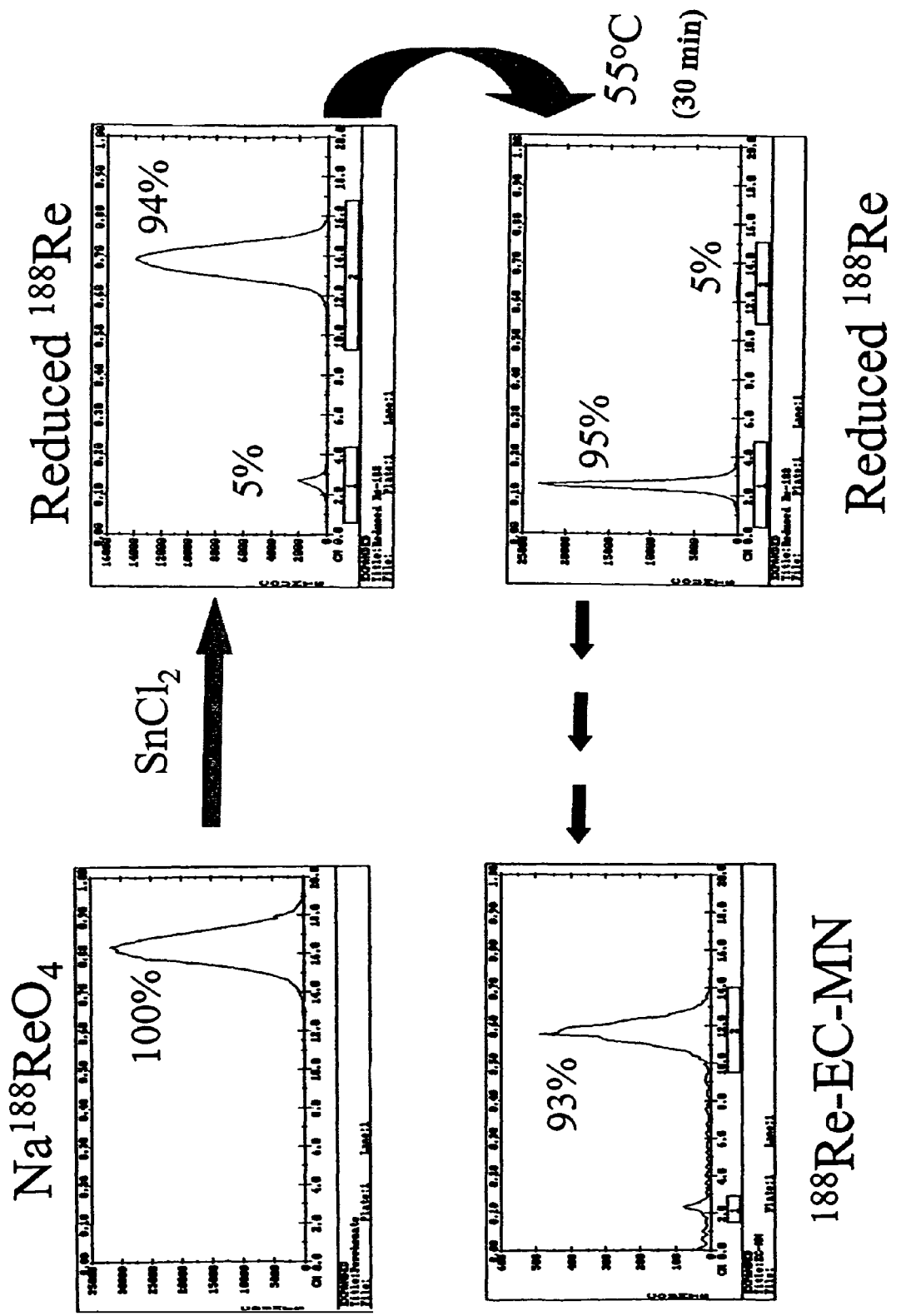
FIG. 40: Synthesis of $^{188}$Re-EC-metronidazole. Perrhenate was eluted from a 188W/188Re generator with 0.9% saline (20 mCi/ml). Eluant was reduced in the presence of Tin (II) Chloride and chelated to EC-MN; %=percent of total counts; mobile phase: saline.

39). Planar images confirmed that the tumors could be visualized with $^{99m}$Tc-EC-TML (FIG. 40).

Example 11

Targeting Glucosamine and Glucose Metabolism with EC-Deoxyglucose a. Synthesis of EC-deoxyglucose (EC-DG)

Figure 41:
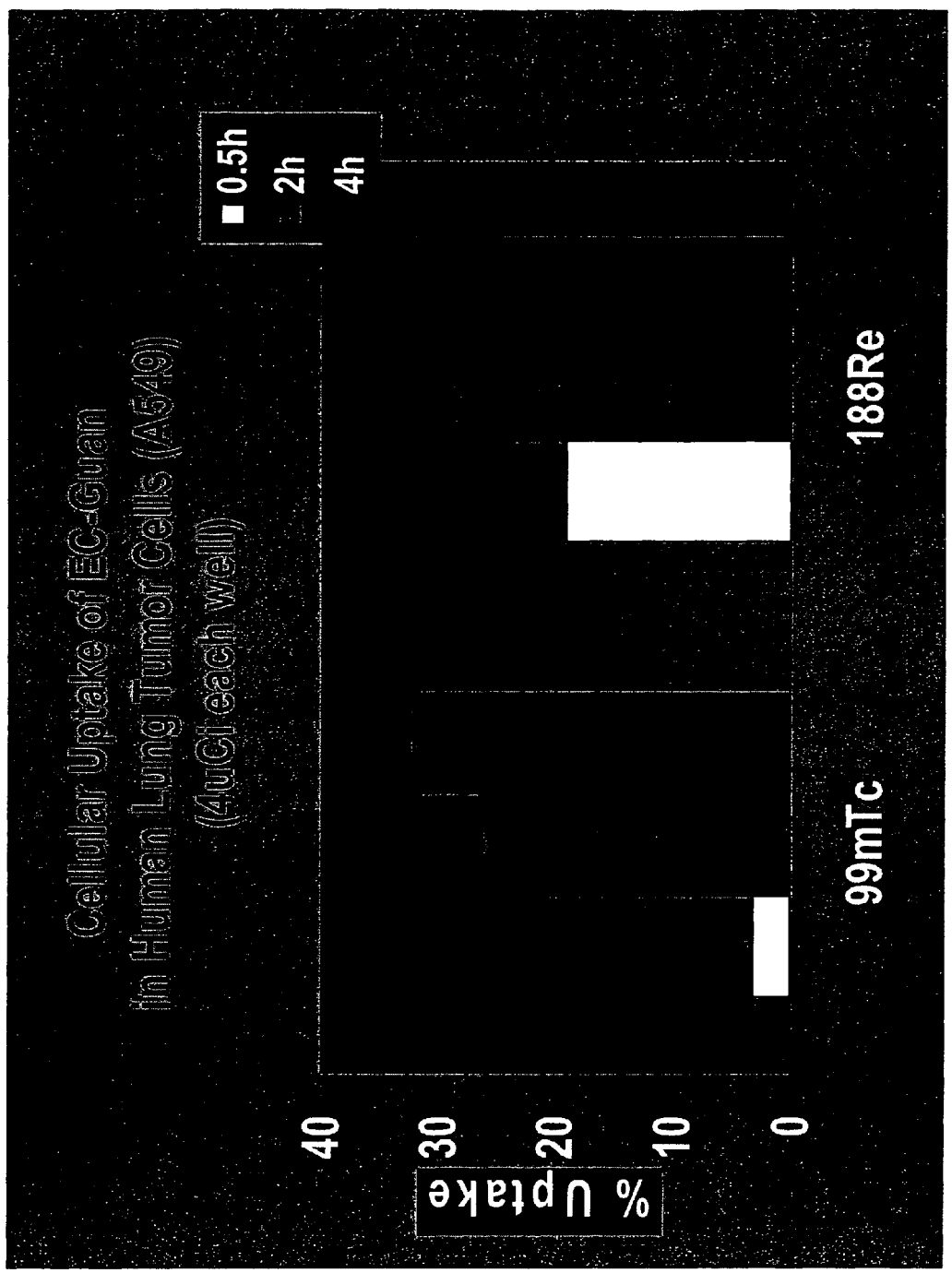
FIG. 41: In vitro cell culture of $^{188}$Re- and $^{99m}$Tc-labeled EC-penciclovir (EC-Guanine).

A signal transduction pathway, glucosamine metabolism was targeted with EC-deoxyglucose, a compound of the current invention. Sodium hydroxide (1N, 1 ml) was added to a stirred solution of EC (110 mg, 0.41 mmol) in water (5 ml). To this colorless solution, sulfo-NHS (241.6 mg, 1.12 mmol) and EDC (218.8 mg, 1.15 mmol) were added. D-Glucosamine hydrochloride salt (356.8 mg, 1.65 mmol) was then added. The mixture was stirred at room temperature for 24 hours and pH was adjusted to 6.4-7.0. The mixture was dialyzed for 48 hours using Spectra/POR molecular porous membrane with cut-off at 500 (Spectrum Medical Industries Inc., Houston, Tex.). After dialysis, the product was frozen dried using lyophilizer (Labconco, Kansas City, Mo.). The product weighed 291 mg (yield 60%). $^1$H-NMR (D$_2$O) δ 2.60-2.90 (m, 4H and —CH$_2$—SH of EC), 2.95 (t, 2H, glucosamine 5-CH—CH$_2$OH) 3.20 (d, 4H, glucosamine 6-CH$_2$OH), 3.30-3.95(m, 6H glucosamine1,3,4-CH and 4H CH$_2$—SH of EC) 3.30-3.66 (m, 4H, CH$_2$—CH$_2$— of EC), 4.15-4.30 (t, 2H, NH—CH—CO of EC), 4.60 (d, 2H, glucosamine 2-CH—NH$_2$). FAB MS m/z 591 (M+, 20). Structure is shown in FIG. 41.

b. Tissue Distribution Studies of $^{99m}$Tc-EC-DG

Female athymic nude mice (NCr-nu/nu, NCI, Bethasda, Md.) were inoculated with human lung cancer cells (A549 tumor cell line, 3×106 cells/mouse, intramuscular) by one author in the mid-dorsal region. After the tumor reached 6 mm, separate biodistribution studies using $^{99m}$Tc-EC-DG and 18F-FDG were conducted. Each received $^{99m}$Tc-EC-DG or 18F-FDG intravenously (n=3/time point). The injection activity was 1-3 μCi/mouse. The injected mass of $^{99m}$Tc-EC-DG was 0.2 mg/rodent. Following administration of the radiotracers, the rodents were sacrificed and the selected tissues were excised, weighed and counted for radioactivity. $^{99m}$Tc-EC-DG had higher tumor/muscle and tumor/brain ratios as a function of time, while 18F-FDG had higher tumor/blood ratios (Tables 4 and 5).

TABLE 5

Biodistribution of $^{18}$FDG in Lung Tumor-Bearing Mice
% of injected dose per gram of tissue weight

|  | 30 min | 2 h | 4 h |
| --- | --- | --- | --- |
| Blood | 0.793 ± 0.067 | 0.236 ± 0.009 | 0.203 ± 0.062 |
| Lung | 2.490 ± 0.209 | 2.222 ± 0.137 | 2.280 ± 0.182 |
| Liver | 1.051 ± 0.057 | 0.586 ± 0.040 | 0.785 ± 0.039 |
| Stomach | 5.046 ± 0.461 | 4.374 ± 0.864 | 2.278 ± 0.455 |
| Spleen | 1.824 ± 0.196 | 1.903 ± 0.144 | 1.591 ± 0.161 |
| Kidney | 1.137 ± 0.117 | 0.553 ± 0.104 | 0.568 ± 0.027 |
| Thyroid | 4.490 ± 0.526 | 4.617 ± 0.400 | 4.424 ± 0.442 |
| Muscle | 4.876 ± 0.621 | 5.409 ± 0.611 | 4.743 ± 0.610 |
| Intestine | 2.322 ± 0.542 | 2.764 ± 0.496 | 1.562 ± 0.342 |
| Tumor | 2.226 ± 0.150 | 1.699 ± 0.172 | 1.606 ± 0.182 |
| Brain | 6.557 ± 0.390 | 3.113 ± 0.132 | 2.065 ± 0.080 |
| Heart | 11.94 ± 2.571 | 20.33 ± 7.675 | 19.35 ± 8.286 |
| Tumor/Blood | 2.821 ± 0.144 | 7.261 ± 1.007 | 8.932 ± 1.973 |
| Tumor/Muscle | 0.463 ± 0.026 | 0.319 ± 0.031 | 0.346 ± 0.048 |
| Tumor/Lung | 0.912 ± 0.119 | 0.775 ± 0.113 | 0.717 ± 0.106 |

Values shown represent the mean ± standard deviation of data from 3 animals.

TABLE 6

Biodistribution of $^{99m}$Tc-EC-DG in Lung Tumor-Bearing Mice
% of injected dose per gram of tissue weight

|  | 30 min | 2 h | 4 h |
| --- | --- | --- | --- |
| Blood | 1.607 ± 0.389 | 0.977 ± 0.267 | 0.787 ± 0.152 |
| Lung | 1.048 ± 0.259 | 0.721 ± 0.210 | 0.606 ± 0.128 |
| Liver | 5.674 ± 2.089 | 5.807 ± 1.708 | 6.656 ± 1.786 |
| Stomach | 0.540 ± 0.113 | 0.439 ± 0.138 | 0.541 ± 0.119 |
| Spleen | 3.240 ± 1.709 | 4.205 ± 1.374 | 5.933 ± 3.194 |
| Kidney | 6.726 ± 1.842 | 5.687 ± 1.540 | 4.318 ± 0.890 |
| Thyroid | 0.929 ± 0.212 | 0.665 ± 0.207 | 0.692 ± 0.119 |
| Muscle | 0.264 ± 0.072 | 0.148 ± 0.039 | 0.147 ± 0.022 |
| Intestine | 0.510 ± 0.093 | 0.417 ± 0.110 | 0.374 ± 0.073 |
| Tumor | 0.787 ± 0.163 | 0.415 ± 0.123 | 0.414 ± 0.161 |
| Brain | 0.058 ± 0.008 | 0.042 ± 0.006 | 0.042 ± 0.006 |
| Heart | 0.611 ± 0.193 | 0.336 ± 0.080 | 0.318 ± 0.071 |
| Tumor/Blood | 0.499 ± 0.022 | 0.424 ± 0.022 | 0.502 ± 0.120 |
| Tumor/Muscle | 3.352 ± 0.749 | 2.754 ± 0.120 | 2.795 ± 0.982 |
| Tumor/Lung | 0.769 ± 0.047 | 0.587 ± 0.046 | 0.640 ± 0.120 |

Values shown represent the mean ± standard deviation of data from 3 animals.

c. Gamma Scintigraphic Imaging Studies

Figure 42:
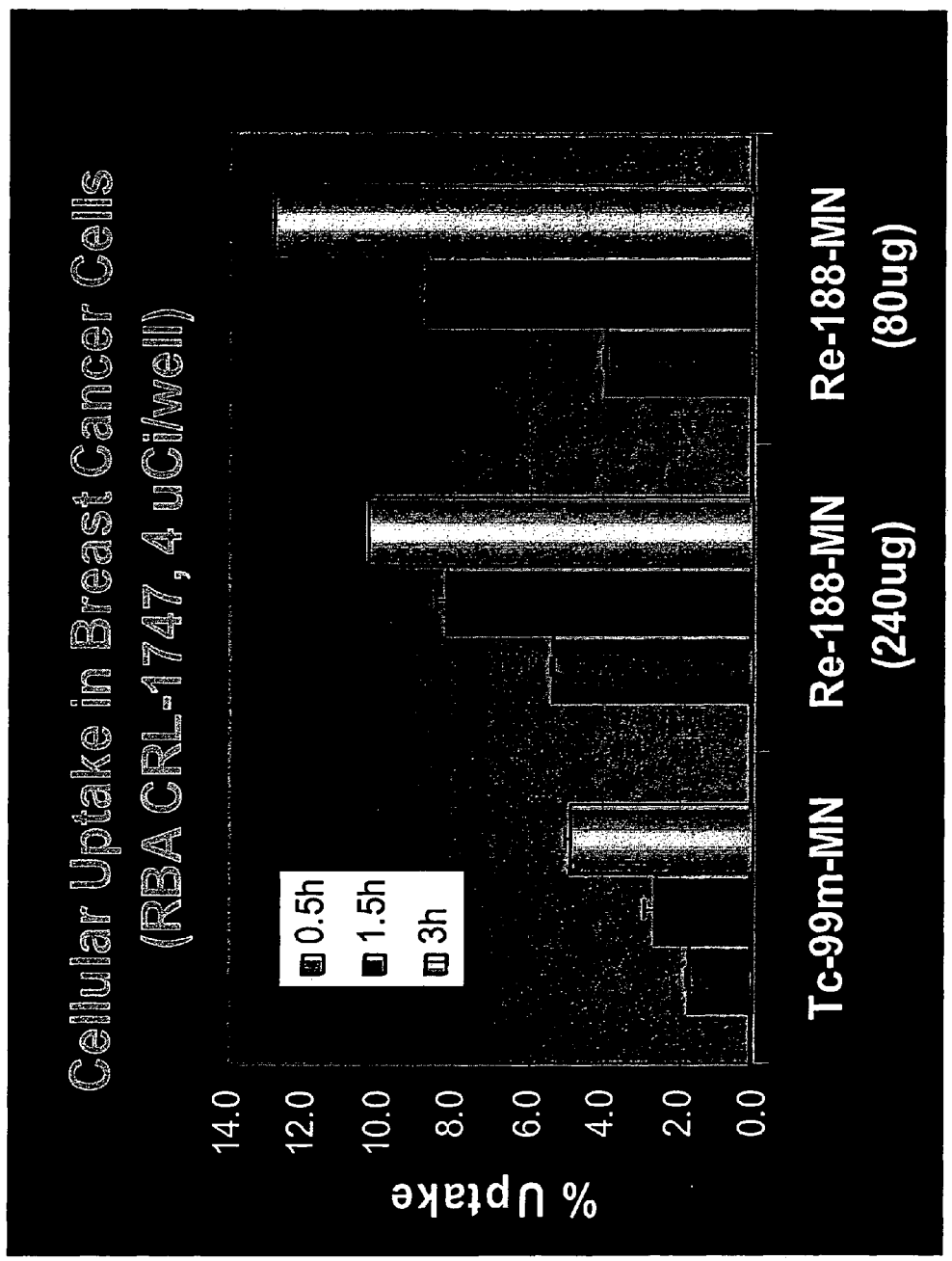
FIG. 42: In vitro cell culture of $^{188}$Re-EC-metronidazole.

Female Fischer 344 rats (250-275 g each) (Harlan, Inc., Indianapolis, Ind.) were inoculated with mammary tumor cells by one author from the 13762 tumor cell line (s.c. 106 cells/rat, a tumor cell line specific to Fischer rats). After 8-10 days, tumor volumes of 0.3-0.6 cm were measured. Scintigraphic images were obtained 0.5, 2 and 4 hours after i.v. injection of 300 μCi of $^{99m}$Tc-EC or $^{99m}$Tc-EC-DG (n=3/agent, total 6 rats). ROI between tumor tissue and muscle (at symmetric site) was used to determine tumor/non-tumor ratios. The smallest tumor volume that could be detected by $^{99m}$Tc-EC-DG was 3 mm. The medium-sized tumor (6 mm) showed higher uptake at each time point. Heart, kidneys, liver, and bladder were visualized (FIG. 42).

Other small molecules that can be applied using EC technology under this example, including EC-amifostine, EC-lactose, EC-pyridoxal (structure is shown in FIG. 43), EC-Fullerene (EC-carbon 60, structure is shown in FIG. 44).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

d. Synthesis and Formulation of $^{188}$Re-EC-DG

Figure 39:
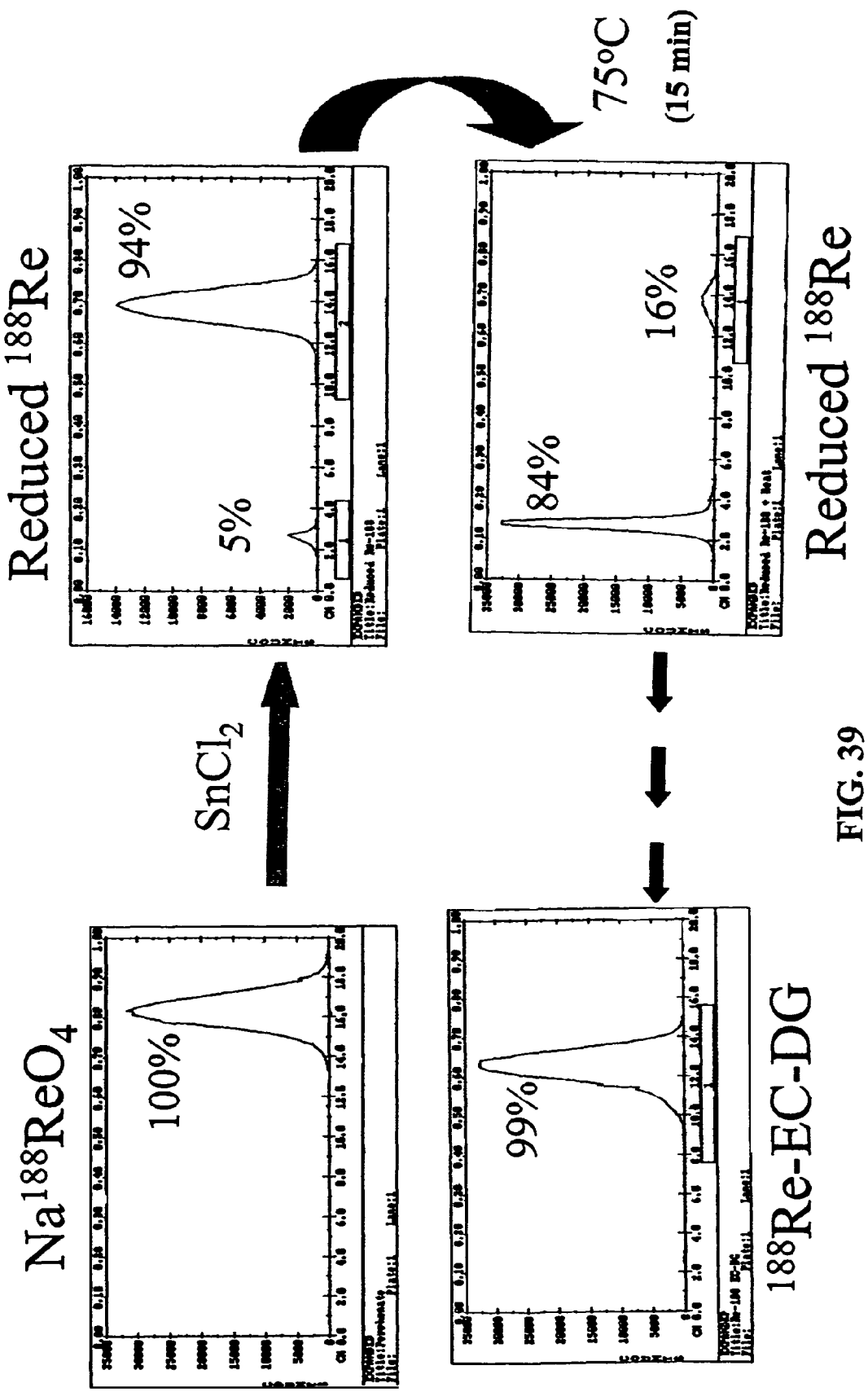
FIG. 39: Synthesis of $^{188}$Re-EC deoxyglucose. Perrhenate was eluted from a 188W/188Re generator with 0.9% saline (20 mCi/ml). Eluant was reduced in the presence of Tin (II) Chloride and chelated to EC-DG; %=percent of total counts; mobile phase: saline.

To develop EC-DG in a kit form, EC-DG (10 mg) dissolved in 0.2 ml of water was freeze dried with tin chloride (2 mg in 0.2 ml of water) and gluconate (3 mg) in a 10 ml medi-vial and stored at room temperature prior to labeling. During labeling, the freeze dried powder was reconstituted in saline (0.5 ml) and pertechnate (10 mCi) was added. The kit was heated at 55° C. for 30 min (or 75° C. for 15 min). Radiochemical purity of $^{99m}$Tc-EC-DG was greater than 95% as determined by radio-TLC (saline, Rf: 0.8) (FIG. 39). A similar method could be applied to other EC-agents such as EC-metronidazole (EC-MN)(FIG. 40) and EC-penciclovir (also known as EC-Guan). To demonstrate the similarity of chemistry between Re-188 and Tc-99m, cell culture of Re-188 and Tc-99m labeled EC-Guan and EC-metronidazole was performed. There was no marked difference between uptakes (FIG. 41 and FIG. 42).

Figure 43A:
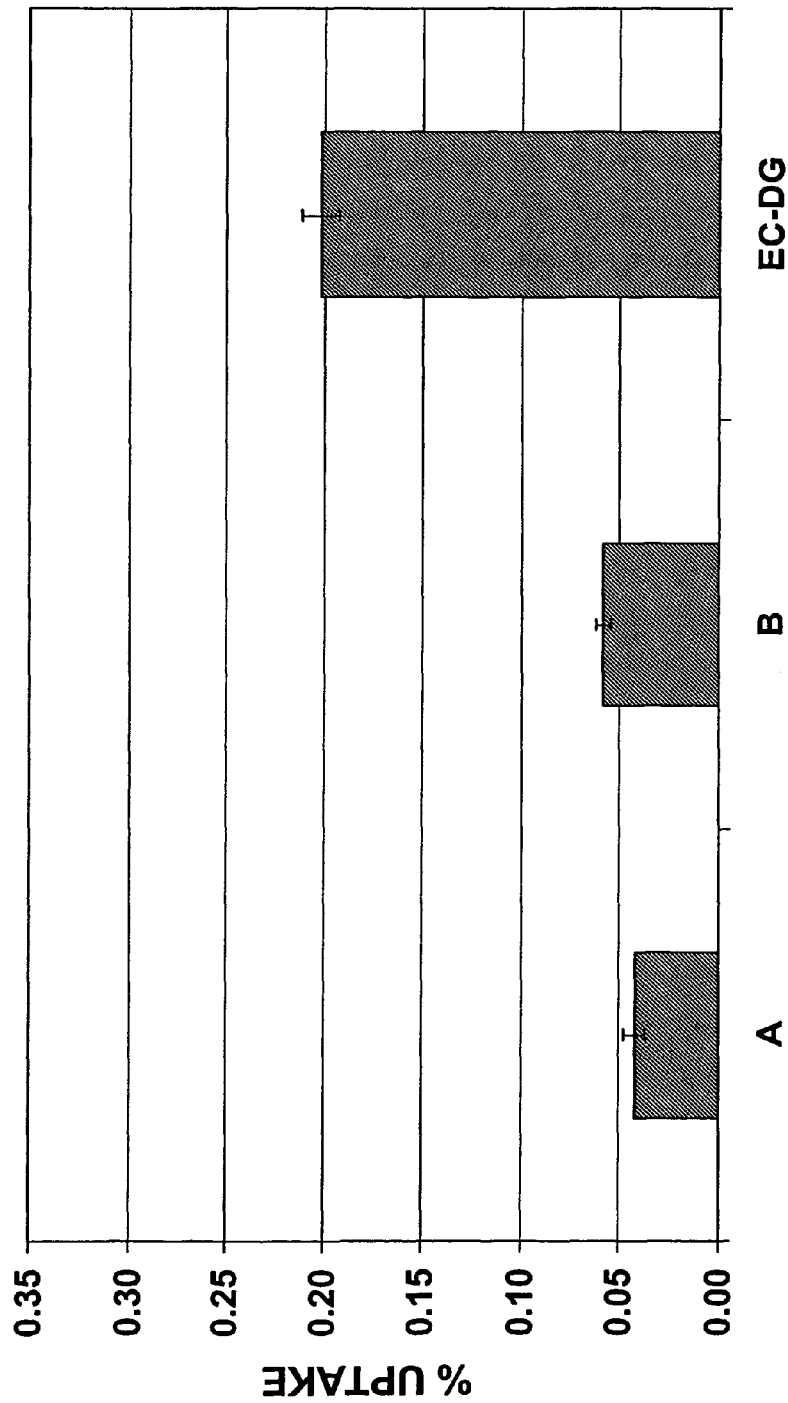
FIG. 43A, FIG. 43B, FIG. 43C: In vitro cell culture of $^{99m}$Tc-EC-deoxyglucose (kit formulation)
Figure 43B:
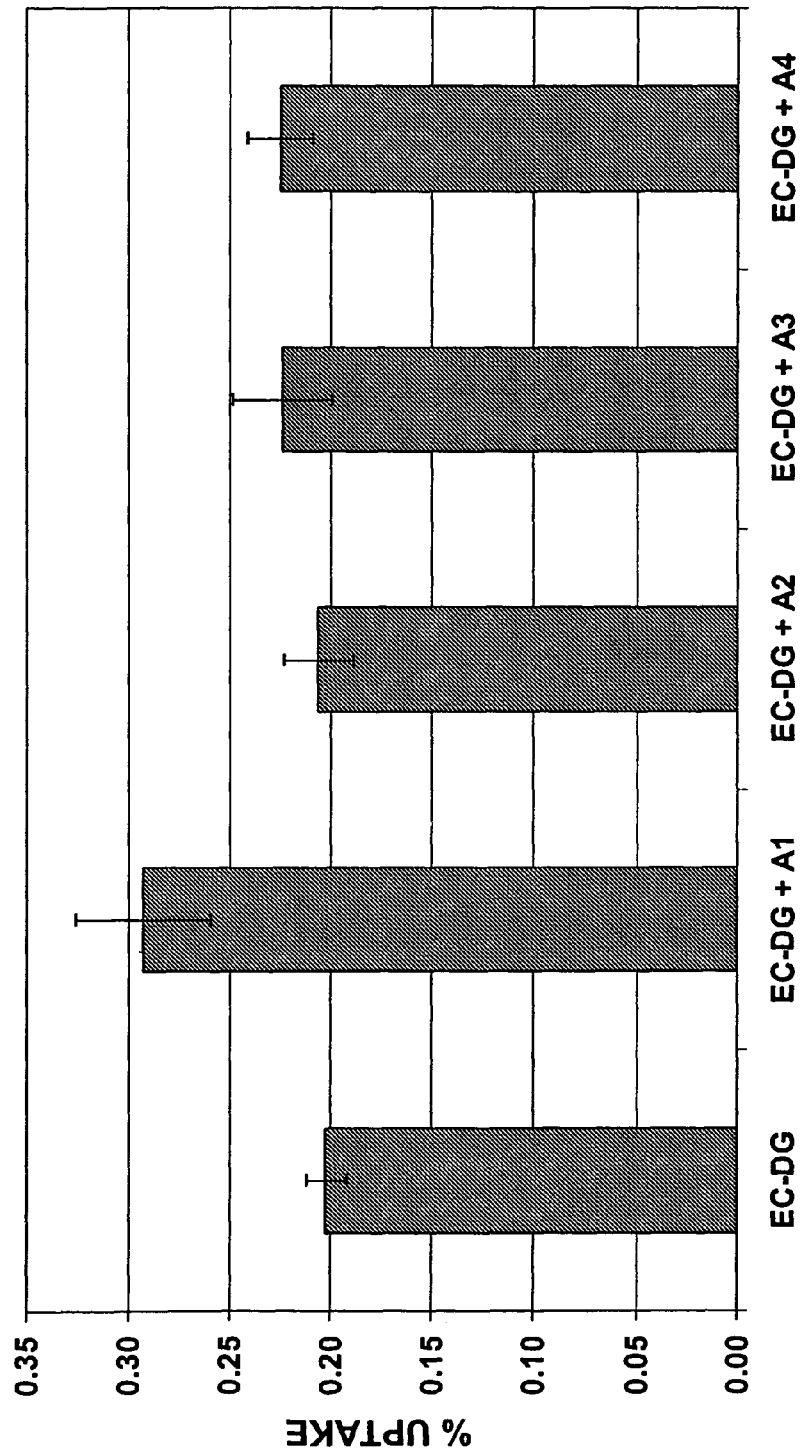
Figure 43C:
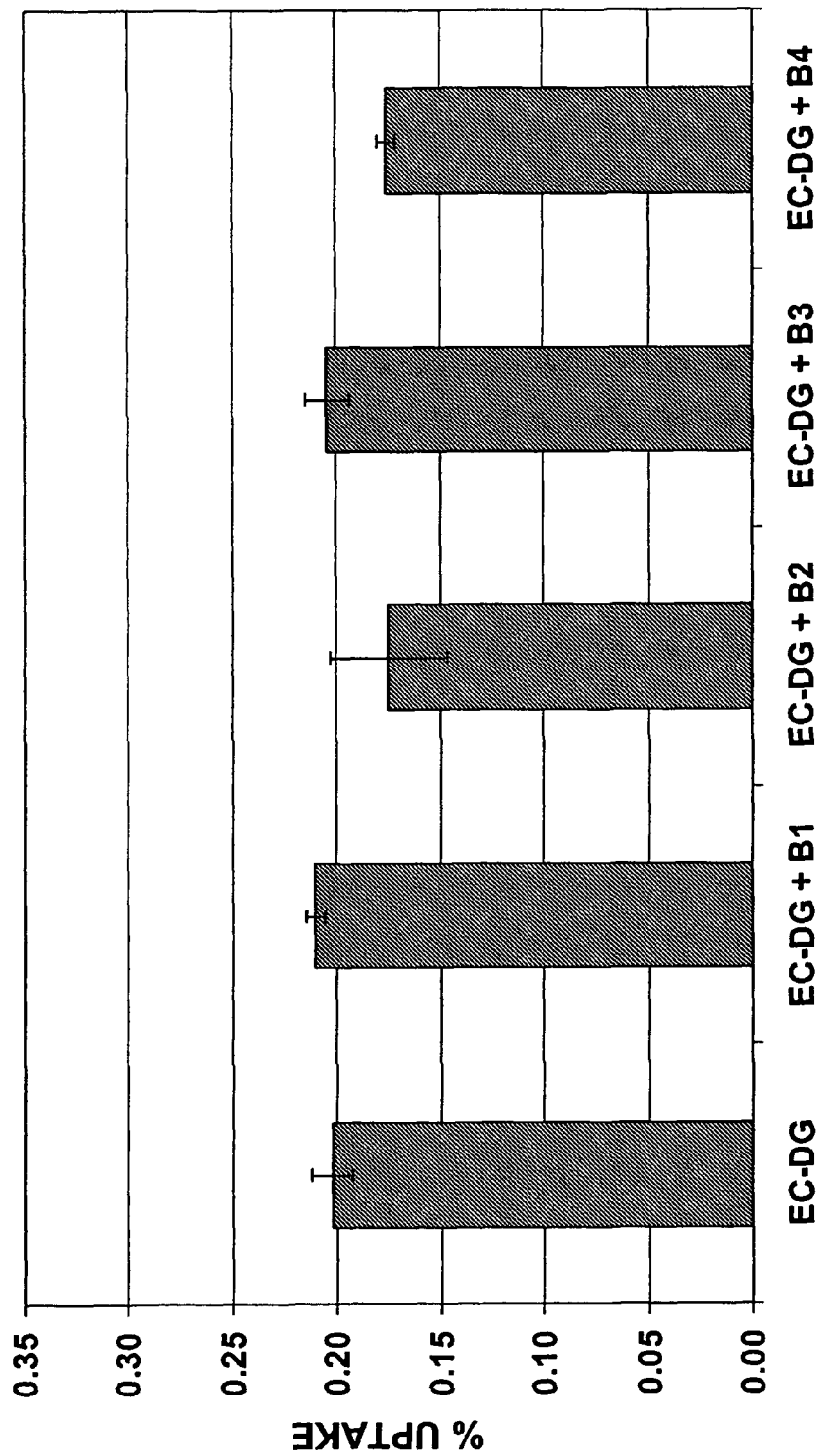

It may also be important to include an antioxidant and a transition chelator in the composition to prevent oxidation of the ethylenedicysteine. For example, the antioxidant may be vitamin C (ascorbic acid). However, other antioxidants known to those of ordinary skill in the art, such as tocopherol, pyridoxine, thiamine, or rutin, may also be used. Any transition chelator known to those of ordinary skill in the art may be used in conjunction with the present invention. Examples of transition chelators include glucoheptonate, gluconate, glucarate, citrate, and tartarate. In certain embodiments, the transition chelator is gluconate or glucarate, which do not interfere with the stability of ethylenedicysteine. In vitro cell culture of $^{99m}$Tc-EC-deoxyglucose (EC-DG) with or without transition chelators (gluconate and glucarate) does not interfere with the stability of $^{99m}$Tc-EC-DG (FIG. 43A-43C).

REFERENCES

The following references, to the extent that they provide exemplary procedural or other details supplementary to those set forth herein, are specifically incorporated herein by reference.
U.S. Pat. No. 5,268,163
U.S. Pat. No. 5,605,672
U.S. Pat. No. 5,817,776
U.S. Pat. No. 5,955,053
U.S. Pat. No. 5,986,074
U.S. Pat. No. 6,284,220
AU Patent 0175210A5
PCT Appln. WO 0175125A1
PCT Appln. WO 0180906A2
PCT Appln. WO 0191807A2
PCT Appln. WO 0232291
PCT Appln. WO 9116076A1
PCT Appln. WO 9428940A1
Alauddin et al., *Nucl. Med. Biol.*, 23:787-792, 1996.
Alauddin et al., *Nucl. Med. Biol.*, 26:371-376, 1999.
Alauddin et al., *J. Nucl. Med.*, 42(11):1682-1690, 2001.
Alauddin and Conti, *Nucl. Med. Biol.*, 25:175-180, 1998.
Banerjeei et al., *Anticancer Res.*, 20:2641-2645, 2000.
Bertolini et al., *Br. J. Haematol.*, 106:5045-09, 1999.
Blondeau et al., *Can. J. Chem.*, 45:49-52, 1967.
Bocci et al., *Cancer Chemother. Pharmacol.*, 43:205-212, 1999.
Burian et al., *Acta Otolaryngol.*, 119:289-292, 1999.
Canet et al., *Magn. Reson. Med.*, 43(3):403-409, 2000.
Cao, *Haematologica*, 84:643-650, 1999.
Dhanabal et al., *J. Biol. Chem.*, 274:11721-11726, 1999.
Duda et al., *Cancer Res.*, 60:1111-1116, 2000.
Frisch and Screaton, *Curr. Opin. Cell Biol.* 13:555-562, 2001.
Gambhir et al., *J. Nucl. Med.*, 39:2003-2011, 1998.
Gambhir et al., *Proc. Natl. Acad. Sci. USA*, 96:2333-2338, 1999.
Gambhir et al., *Proc. Natl. Acad. Sci. USA*, 97:2785-2790, 2000.
Gasparini, *Drugs*, 58:17-38, 1999.
Goethals et al., *J. Nucl. Med.*, 36:880-882, 1995.
Green and Evan, *Cancer Cell*, 1:19-30, 2002.
Guang-Wu, et al., *Laryngoscope*, 110:2066-2069, 2000.
Higashi et al., *J. Nucl. Med.*, 34:414-419, 1992.
Inoue et al., *Clin. Cancer Res.*, 6:4866-4873, 2000.
Iyer et al., *J. Nucl. Med.*, 42:96-105, 2001.
Jiang et al., *Am. J. Physiol. Cell Physiol.*, 280:1140-1150, 2001.
Jouan et al., *Blood*, 94:984-993, 1999.
Kao et al., *Cancer*, 83:64-68, 1998.
Laissy et al., *Magn. Reson. Imaging*, 12(3):413-419, 1994.
Lamszus et al., *Neurosurgery*, 46:938-948, 2000.
Li et al., *Inorg. Chem.*, 35(2):404-414, 1996.
Liao F et al., *Cancer Res.*, 60:6805-6810, 2000.
Logothetis et al., *Clin. Cancer Res.*, 7:1198-1203, 2001.
Lozonschi et al., *Cancer Res.*, 59:1252-1258, 1999.
Maekawa et al., *Cancer Res.*, 59:1231-1235, 1999.
Martiat et al., *J. Nuc. Med.*, 29:1633-1637, 1988.
McConathy et al., *Nucl. Med. Biol.*, 30:477-490, 2003.
Minn et al., *Cancer*, 61:1776-1781, 1988.
Moreira et al., *J. Neurooncol.*, 43:109-114, 1999.
Moulton et al., *Circulation*, 99:1726-1732, 1999.
Namavari et al., *Nuc. Med. Biol.*, 27:157-162, 2000.
Ohtsuki et al., *Eur. J. Nuc. Med.*, 26(10):1251-1258, 1999.
Okada et al., *J. Nucl. Med.*, 32:686-691, 1991.
Okada et al., *J. Nucl. Med.*, 33:325-329, 1992.
Pedram et al., *Endocrinology*, 142:1578-1586, 2001.
Petzelbauer et al., *Cytokine*, 7:267-272, 1995.
Ratner and Clarke, *J. AM Chem. Soc.*, 59:200-206, 1937.
Reed, *Cancer Cell*, 3:17-22, 2003.
Sakamoto et al., *Invest. Ophthalmol. Vis. Sci.*, 36:1076-1083, 1995.
Shields et al., *J. Nucl. Med.*, 31:337-342, 1990.
Sion-Vardy et al., *Pathol. Res. Pract.*, 197:1-5, 2001.
Slaton et al., *Am. J. Pathol.*, 158:735-743, 2001.
Smith et al., *J. Clin. Oncol.*, 18:2046-2052, 2000.
Smith et al., *Ann. Oncol.*, 10:707-713, 1999.
Taggart et al., *Human Mutation.*, 13(3):210-220, 1999.
Tjuvajev et al., *J. Nucl. Med.*, 43:1072-1083, 2002.
Tschopp et al., *Curr. Biol.* 9:R381-R384, 1999.
Ugurel et al., *J. Clin. Oncol.*, 19:577-583, 2001.
Van Nerom et al., *Eur. J. Nucl. Med.*, 20:738-746, 1993.
Vriens et al., *J. Thorac. Cardiovasc. Surg.*, 116:844-853, 1998.
Wu et al., *J. Diabetes Complications*, 17:297-300, 2003.
Xiangming et al., *Ann. Surg. Oncol.*, 5:585-589, 1998.
Yaghoubi et al., *J. Nucl. Med.*, 42:1225-1234, 2001.
Yeh et al., *Mol. Pharmacol.*, 59:1333-1342, 2001.

What is claimed is:

1. A compound that comprises an $N_2S_2$ chelate conjugated to a targeting ligand of formula:

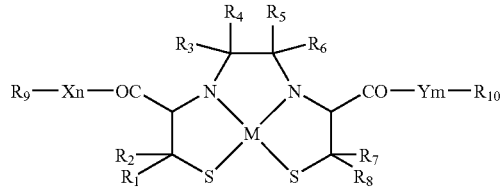

wherein $R_1$, $R_2$, $R_3$, $R_4$, $R_5$, $R_6$, $R_7$ and $R_8$ are independently H or $CH_3$;

$R_9$ and $R_{10}$ are independently H, $CH_3$, OH, or aminopenciclovir;

provided that at least one of $R_9$ and $R_{10}$ is aminopenciclovir;

n is 0 or 1;

m is 0 or 1;

X is a water soluble peptide, $C_1$-$C_{20}$ alkyl, glutamic acid, polyglutamic acid, aspartic acid, polyaspartic acid, bromoethylacetate, ethylenediamine or lysine when n is 1, or a bond when n is 0;

Y is a water soluble peptide, $C_1$-$C_{20}$ alkyl, glutamic acid, polyglutamic acid, aspartic acid, polyaspartic acid, bromoethylacetate, ethylenediamine or lysine when m is 1, or a bond when m is 0; and M is $^{99m}$Tc (oxotechnetium), $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu.

2. The compound of claim 1, wherein the $N_2S_2$ chelate is further defined as ethylenedicysteine.

3. The compound of claim 1, further comprising a radioactive nuclide.

4. The compound of claim 3, wherein the radioactive nuclide comprises $^{99m}$Tc, $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu.

5. The compound of claim 1, further comprising a water soluble peptide, $C_1$-$C_{20}$ alkyl, glutamic acid, polyglutamic acid, aspartic acid, polyaspartic acid, bromoethylacetate, ethylenediamine or lysine positioned between the targeting ligand and the chelate.

6. A method of synthesizing a radiolabeled $N_2S_2$ chelate conjugated to targeting ligand comprising the steps:
a) obtaining a compound in accordance with claim 1;
b) admixing said compound a radionuclide and a reducing agent to obtain a radionuclide labeled derivative, wherein the $N_2S_2$ chelate forms a chelate with the radionuclide.

7. The method of claim 6, wherein said reducing agent is a dithionite ion, a stannous ion or a ferrous ion.

8. The method of claim 6, wherein said radionuclide is $^{99m}$Tc, $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu.

9. A method of imaging a site within a mammalian body comprising the steps:
a) administering an effective diagnostic amount of a compound in accordance with claim 3 to said site; and
b) detecting a radioactive signal from said compound localized at a site.

10. The method of claim 9, wherein said site is a tumor.

11. The method of claim 9, wherein said site is an infection.

12. The method of claim 9 wherein said site is breast cancer, ovarian cancer, prostate cancer, endometrium, heart cancer, lung cancer, brain cancer, liver cancer, folate (+) cancer, ER (+) cancer, spleen cancer, pancreas cancer, or intestine cancer.

13. A kit for preparing a radiopharmaceutical preparation comprising:
a) a sealed container including a predetermined quantity of a compound that is a $N_2S_2$ chelate-targeting ligand conjugate in accordance with claim 1; and
b) a sufficient amount of a reducing agent.

14. The kit of claim 13, further comprising a radionuclide.

15. The kit of claim 14, wherein the radionuclide is $^{99m}$Tc, $^{188}$Re, $^{186}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu or $^{62}$Cu.

16. The kit of claim 13, further comprising an antioxidant.

17. The kit of claim 16, wherein the antioxidant is vitamin C, tocopherol, pyridoxine, thiamine, or rutin.

18. The kit of claim 17, wherein the antioxidant is vitamin C.

19. The kit of claim 13, further comprising a transition chelator.

20. The kit of claim 19, wherein the transition chelator is glucoheptonate, gluconate, glucarate, citrate, or tartarate.

21. The kit of claim 20, wherein the transition chelator is gluconate or glucarate.

22. The kit of claim 13, wherein the reducing agent is tin (II) chloride or triphenylphosphine.

* * * * *

UNITED STATES PATENT AND TRADEMARK OFFICE
CERTIFICATE OF CORRECTION

PATENT NO. : 9,050,378 B2  Page 1 of 1
APPLICATION NO. : 10/732919
DATED : June 9, 2015
INVENTOR(S) : David J. Yang et al.

It is certified that error appears in the above-identified patent and that said Letters Patent is hereby corrected as shown below:

On The Title Page,

Item (75) Inventors, delete "Jerry L. Bryant, Jr., Houston, TX (US)".

Item (60) Related U.S. Application Data, insert:

--Continuation of application No. 10/703,405, filed on Nov. 7, 2003, now abandoned.

Provisional application No. 60/424,493, filed on Nov. 7, 2002.--.

Signed and Sealed this
Twenty-third Day of February, 2016

Michelle K. Lee
*Director of the United States Patent and Trademark Office*